US007045498B2

(12) United States Patent
Kindsvogel et al.

(10) Patent No.: US 7,045,498 B2
(45) Date of Patent: May 16, 2006

(54) SOLUBLE ZCYTOR11 CYTOKINE RECEPTORS

(75) Inventors: Wayne R. Kindsvogel, Seattle, WA (US); Stavros Topouzis, Seattle, WA (US)

(73) Assignee: ZymoGenetics, Inc., Seattle, WA (US)

( * ) Notice: Subject to any disclaimer, the term of this patent is extended or adjusted under 35 U.S.C. 154(b) by 45 days.

(21) Appl. No.: 09/925,055

(22) Filed: Aug. 8, 2001

(65) Prior Publication Data

US 2003/0157096 A1 Aug. 21, 2003

Related U.S. Application Data

(60) Provisional application No. 60/250,876, filed on Dec. 1, 2000, provisional application No. 60/223,827, filed on Aug. 8, 2000.

(51) Int. Cl.
*A61K 38/19* (2006.01)
*A61K 45/00* (2006.01)
*C07K 14/47* (2006.01)

(52) U.S. Cl. .......................... 514/2; 530/351; 424/85.2

(58) Field of Classification Search .................... 514/2; 530/351; 424/85.2

See application file for complete search history.

(56) References Cited

U.S. PATENT DOCUMENTS 5,965,704 A * 10/1999 Lok et al. .................. 530/350

FOREIGN PATENT DOCUMENTS

| | | |
|---|---|---|
| WO | 99/07848 | 2/1999 |
| WO | 00/39161 | 6/2000 |
| WO | 01/16318 | 8/2001 |
| WO | 02/072607 | 9/2002 |

OTHER PUBLICATIONS

Xie, M-H et al., *J. Biol. Chem.* 275:31335-31339, 2000.
Kotenko, SV et al., *J. Immunol.* 166:7096-7013, 2001.
Kotenko, SV et al., *J. Biol. Chem.* 276:2725-2732, 2001.
Kotenko, SV et al., *Oncogene,* 19:2557-2565, 2000.
Zhang, et al., *J. Biol. Chem,* 272:9474-9480, 1997.
Blumberg, H. et al., *Cell 104:*9-19, 2001.
Xu. W. et al., *Proc. Nat. Acad. Sci.* 98:9511-9516, 2001 (pub. online Jul. 31, 2001).
Liu et al., *Journal of Immunology* 152:1821-1829, 1994.
Dumoutier, L. et al., *Journal of Immunology* 164: 1814-1819, 2000.
Dumoutier, L. et al., *Proc. Nat. Acad. Sci. 97:*10144-10149, 2000.
Dumoutier, L. et al., *J. Immunol. 166:*7090-7095, 2001.
Dumoutier, L. et al., *J. Immunol. 167:*3545-3549, 2001.
GenBank Accession No. T70439, 1995.
GenBank Accession No. T70354, 1995.
GenBank Accession No. AA132964, 1995.

* cited by examiner

*Primary Examiner*—Janet L. Andres
*Assistant Examiner*—Fozia Hamud
(74) *Attorney, Agent, or Firm*—Jennifer K. Johnson

(57) ABSTRACT

Novel polypeptide combinations, polynucleotides encoding the polypeptides, and related compositions and methods are disclosed for soluble zcytor11 receptors that may be used as novel cytokine antagonists, and within methods for detecting ligands that stimulate the proliferation and/or development of hematopoietic, lymphoid and myeloid cells in vitro and in vivo. Ligand-binding receptor polypeptides and antibodies can also be used to block TIF activity in vitro and in vivo, and may be used in conjunction with TIF and other cytokines to selectively stimulate the immune system. The present invention also includes methods for producing the protein, uses therefor and antibodies thereto.

9 Claims, No Drawings

SOLUBLE ZCYTOR11 CYTOKINE RECEPTORS

REFERENCE TO RELATED APPLICATIONS

This application is related to Provisional Application No. 60/223,827, filed on Aug. 8, 2000. This application is also related to Provisional Application No. 60/250,876, filed on Dec. 1, 2000. Under 35 U.S.C. § 119(e)(1), this application claims benefit of said Provisional Applications.

BACKGROUND OF THE INVENTION

Cytokines are soluble proteins that influence the growth and differentiation of many cell types. Their receptors are composed of one or more integral membrane proteins that bind the cytokine with high affinity and transduce this binding event to the cell through the cytoplasmic portions of the certain receptor subunits. Cytokine receptors have been grouped into several classes on the basis of similarities in their extracellular ligand binding domains. For example, the receptor chains responsible for binding and/or transducing the effect of interferons (IFNs) are members of the type II cytokine receptor family (CRF2), based upon a characteristic 200 residue extracellular domain. The demonstrated in vivo activities of these interferons illustrate the enormous clinical potential of, and need for, other cytokines, cytokine agonists, and cytokine antagonists.

DESCRIPTION OF THE INVENTION

The present invention fills this need by providing novel cytokine receptors and related compositions and methods. In particular, the present invention provides for an extracellular ligand-binding region of a mammalian Zcytor11 receptor, alternatively also containing either a transmembrane domain or both an intracellular domain and a transmembrane domain.

Moreover, the present invention fills this need by providing novel soluble cytokine receptors that can be used to antagonize the effects of T-cell inducible factor (IL-TIF) in certain human disease states. In particular, the present invention provides for an extracellular ligand-binding region of a mammalian Zcytor11 receptor, that is either homodimeric, heterodimeric, or multimeric.

Within one aspect, the present invention provides an isolated polynucleotide that encodes a soluble cytokine receptor polypeptide comprising a sequence of amino acid residues that is at least 90% identical to the amino acid sequence as shown in SEQ ID NO:3, and wherein the soluble cytokine receptor polypeptide encoded by the polynucleotide sequence binds or antagonizes IL-TIF (SEQ ID NO:8). In one embodiment, the polynucleotide is as disclosed above, wherein the soluble cytokine receptor polypeptide encoded by the polynucleotide forms a homodimeric receptor complex.

Within a second aspect, the present invention provides an isolated polynucleotide that encodes a soluble cytokine receptor polypeptide comprising a sequence of amino acid residues that is at least 90% identical to the amino acid sequence as shown in SEQ ID NO:3, wherein the soluble cytokine receptor polypeptide encoded by the polynucleotide forms a heterodimeric or multimeric receptor complex. In one embodiment, the polynucleotide is as disclosed above, wherein the soluble cytokine receptor polypeptide encoded by the polynucleotide forms a heterodimeric or multimeric receptor complex further comprising a soluble Class I or Class II cytokine receptor. In another embodiment, the polynucleotide is as disclosed above, wherein the soluble cytokine receptor polypeptide encoded by the polynucleotide forms a heterodimeric or multimeric receptor complex further comprising a soluble CRF2-4 receptor polypeptide (SEQ ID NO:33) or a soluble IL-10 receptor polypeptide (SEQ ID NO:34), or a soluble DIRS1 receptor polypeptide (SEQ ID NO:35). In another embodiment, the polynucleotide is as disclosed above, wherein the soluble cytokine receptor polypeptide encoded by the polynucleotide forms a heterodimeric or multimeric receptor complex further comprising a soluble CRF2-4 receptor polypeptide (SEQ ID NO:33) or a soluble IL-10 receptor polypeptide (SEQ ID NO:34), or a soluble DIRS1 receptor polypeptide (SEQ ID NO:35).

Within a third aspect, the present invention provides an isolated polynucleotide that encodes a soluble cytokine receptor polypeptide comprising a sequence of amino acid residues as shown in SEQ ID NO:3, wherein the soluble cytokine receptor polypeptide encoded by the polynucleotide forms a heterodimeric or multimeric receptor complex. In another embodiment, the polynucleotide is as disclosed above, wherein the soluble cytokine receptor polypeptide encoded by the polynucleotide further comprises a soluble Class I or Class II cytokine receptor. In another embodiment, the polynucleotide is as disclosed above, wherein the soluble cytokine receptor polypeptide encoded by the polynucleotide forms a heterodimeric or multimeric receptor complex further comprising a soluble CRF2-4 receptor polypeptide (SEQ ID NO:33) or a soluble IL-10 receptor polypeptide (SEQ ID NO:34), or a soluble DIRS1 receptor polypeptide (SEQ ID NO:35). In another embodiment, the polynucleotide is as disclosed above, wherein the soluble cytokine receptor polypeptide further encodes an intracellular domain. In another embodiment, the polynucleotide is as disclosed above, wherein the soluble cytokine receptor polypeptide further comprises an affinity tag.

Within another aspect, the present invention provides an expression vector comprising the following operably linked elements: (a) a transcription promoter; a first DNA segment encoding a soluble cytokine receptor polypeptide having an amino acid sequence as shown in SEQ ID NO:3; and a transcription terminator; and (b) a second transcription promoter; a second DNA segment encoding a soluble Class I or Class II cytokine receptor polypeptide; and a transcription terminator; and wherein the first and second DNA segments are contained within a single expression vector or are contained within independent expression vectors.

In one embodiment, the expression vector disclosed above, further comprises a secretory signal sequence operably linked to the first and second DNA segments. In another embodiment, the expression vector is as disclosed above, wherein the second DNA segment encodes a soluble CRF2-4 receptor polypeptide (SEQ ID NO:33) or a soluble L-10 receptor polypeptide (SEQ ID NO:34), or a soluble DIRS1 receptor polypeptide (SEQ ID NO:35).

Within another aspect, the present invention provides a cultured cell comprising an expression vector as disclosed above, wherein the cell expresses the polypeptides encoded by the DNA segments. In one embodiment, the cultured cell comprises an expression vector as disclosed above, wherein the first and second DNA segments are located on independent expression vectors and are co-transfected into the cell, and cell expresses the polypeptides encoded by the DNA segments. In another embodiment, the cultured cell comprises an expression vector as disclosed above, wherein the cell expresses a heterodimeric or multimeric soluble receptor polypeptide encoded by the DNA segments. In another embodiment, the cultured cell is as disclosed above, wherein the cell secretes a soluble cytokine receptor polypeptide heterodimer or multimeric complex. In another embodiment, the cultured cell is as disclosed above, wherein the cell secretes a soluble cytokine receptor polypeptide heterodimer or multimeric complex that binds IL-TIF or antagonizes IL-TIF activity.

Within another aspect, the present invention provides a DNA construct encoding a fusion protein comprising: a first DNA segment encoding a polypeptide having a sequence of amino acid residues as shown in SEQ ID NO:3; and at least one other DNA segment encoding a soluble Class I or Class II cytokine receptor polypeptide, wherein the first and other DNA segments are connected in-frame; and wherein the first and other DNA segments encode the fusion protein.

Within another aspect, the present invention provides a DNA construct encoding a fusion protein as disclosed above, wherein at least one other DNA segment encodes a soluble CRF2-4 receptor polypeptide (SEQ ID NO:33) or a soluble IL-10 receptor polypeptide (SEQ ID NO:34), or a soluble DIRS1 receptor polypeptide (SEQ ID NO:35).

Within another aspect, the present invention provides an expression vector comprising the following operably linked elements: a transcription promoter; a DNA construct encoding a fusion protein as disclosed above; and a transcription terminator, wherein the promoter is operably linked to the DNA construct, and the DNA construct is operably linked to the transcription terminator.

Within another aspect, the present invention provides a cultured cell comprising an expression vector as disclosed above, wherein the cell expresses a polypeptide encoded by the DNA construct.

Within another aspect, the present invention provides a method of producing a fusion protein comprising: culturing a cell as disclosed above; and isolating the polypeptide produced by the cell.

Within another aspect, the present invention provides an isolated soluble cytokine receptor polypeptide comprising a sequence of amino acid residues that is at least 90% identical to an amino acid sequence as shown in SEQ ID NO:3, and wherein the soluble cytokine receptor polypeptide binds IL-TIF or antagonizes IL-TIF activity. In one embodiment, the isolated polypeptide is as disclosed above, wherein the soluble cytokine receptor polypeptide forms a homodimeric receptor complex.

Within another aspect, the present invention provides an isolated polypeptide comprising a sequence of amino acid residues that is at least 90% identical to an amino acid sequence as shown in SEQ ID NO:3, wherein the soluble cytokine receptor polypeptide forms a heterodimeric or multimeric receptor complex. In one embodiment, the isolated polypeptide is as disclosed above, wherein the soluble cytokine receptor polypeptide forms a heterodimeric or multimeric receptor complex further comprising a soluble Class I or Class II cytokine receptor.

In another embodiment, the isolated polypeptide is as disclosed above, wherein the soluble cytokine receptor polypeptide forms a heterodimeric or multimeric receptor complex further comprising a soluble CRF2-4 receptor polypeptide (SEQ ID NO:33) or a soluble IL-10 receptor polypeptide (SEQ ID NO:34), or a soluble DIRS1 receptor polypeptide (SEQ ID NO:35). In another embodiment, the isolated polypeptide is as disclosed above, wherein the polypeptide forms a heterodimeric or multimeric receptor complex further comprising a soluble CRF2-4 receptor polypeptide (SEQ ID NO:33) or a soluble IL-10 receptor polypeptide (SEQ ID NO:34), or a soluble DIRS1 receptor polypeptide (SEQ ID NO:35).

Within another aspect, the present invention provides an isolated soluble cytokine receptor polypeptide comprising a sequence of amino acid residues as shown in SEQ ID NO:3, wherein the soluble cytokine receptor polypeptide forms a heterodimeric or multimeric receptor complex. In another embodiment, the isolated polypeptide is as disclosed above, wherein the soluble cytokine receptor polypeptide forms a heterodimeric or multimeric receptor complex further comprising a soluble Class I or Class II cytokine receptor. In another embodiment, the isolated polypeptide is as disclosed above, wherein the soluble cytokine receptor polypeptide forms a heterodimeric or multimeric receptor complex comprising a soluble CRF2-4 receptor polypeptide (SEQ ID NO:33) or a soluble IL-10 receptor polypeptide (SEQ ID NO:34), or a soluble DIRS1 receptor polypeptide (SEQ ID NO:35). In another embodiment, the isolated polypeptide is as disclosed above, wherein the soluble cytokine receptor polypeptide further comprises an affinity tag, chemical moiety, toxin, or label. Within another aspect, the present invention provides an isolated heterodimeric or multimeric soluble receptor complex comprising soluble receptor subunits, wherein at least one of soluble receptor subunits comprises a soluble cytokine receptor polypeptide comprising a sequence of amino acid residues as shown in SEQ ID NO:3. In one embodiment, the isolated heterodimeric or multimeric soluble receptor complex disclosed above, further comprises a soluble Class I or Class II cytokine receptor polypeptide. In one embodiment, the isolated heterodimeric or multimeric soluble receptor complex disclosed above, further comprises a soluble CRF2-4 receptor polypeptide (SEQ ID NO:33) or a soluble IL-10 receptor polypeptide (SEQ ID NO:34), or a soluble DIRS1 receptor polypeptide (SEQ ID NO:35).

Within another aspect, the present invention provides a method of producing a soluble cytokine receptor polypeptide that forms a heterodimeric or multimeric complex comprising: culturing a cell as disclosed above; and isolating the soluble receptor polypeptides produced by the cell.

Within another aspect, the present invention provides a method of producing an antibody to soluble cytokine receptor polypeptide comprising: inoculating an animal with a soluble cytokine receptor polypeptide selected from the group consisting of: (a) a polypeptide comprising a homodimeric soluble cytokine receptor complex; (b) a polypeptide comprising a soluble cytokine receptor heterodimeric or multimeric receptor complex comprising a soluble Class I or Class II cytokine receptor polypeptide; (c) a polypeptide comprising a soluble cytokine receptor heterodimeric or multimeric receptor complex comprising a soluble CRF2-4 receptor polypeptide (SEQ ID NO:33); (d) a polypeptide comprising a soluble cytokine receptor heterodimeric or multimeric receptor complex comprising a soluble IL-10 receptor polypeptide (SEQ ID NO:34); (e) a polypeptide comprising a soluble cytokine receptor heterodimeric or multimeric receptor complex comprising a soluble DIRS1 receptor polypeptide (SEQ ID NO:34); and wherein the polypeptide elicits an immune response in the animal to produce the antibody; and isolating the antibody from the animal.

Within another aspect, the present invention provides an antibody produced by the method as disclosed above, which specifically binds to a homodimeric, heterodimeric or multimeric receptor complex comprising a soluble cytokine receptor polypeptide. In one embodiment, the antibody disclosed above is a monoclonal antibody.

Within another aspect, the present invention provides an antibody which specifically binds to a homodimeric, heterodimeric or multimeric receptor complex as disclosed above.

Within another aspect, the present invention provides a method for inhibiting IL-TIF-induced proliferation of hematopoietic cells and hematopoietic cell progenitors comprising culturing bone marrow or peripheral blood cells with a composition comprising an amount of soluble cytokine receptor sufficient to reduce proliferation of the hematopoietic cells in the bone marrow or peripheral blood cells as compared to bone marrow or peripheral blood cells cultured in the absence of soluble cytokine receptor. In one embodiment, the method is as disclosed above, wherein the hematopoietic cells and hematopoietic progenitor cells are lymphoid cells. In one embodiment, the method is as disclosed above, wherein the lymphoid cells are macrophages or T cells.

Within another aspect, the present invention provides a method of reducing IL-TIF-induced or IL-9 induced inflammation comprising administering to a mammal with inflammation an amount of a composition of soluble cytokine receptor sufficient to reduce inflammation.

Within another aspect, the present invention provides a method of suppressing an immune response in a mammal exposed to an antigen or pathogen comprising: (1) determining a level of an antigen- or pathogen-specific antibody; (2) administering a composition comprising soluble cytokine receptor polypeptide in an acceptable pharmaceutical vehicle; (3) determining a post administration level of antigen- or pathogen-specific antibody; (4) comparing the level of antibody in step (1) to the level of antibody in step (3), wherein a lack of increase or a decrease in antibody level is indicative of suppressing an immune response.

These and other aspects of the invention will become evident upon reference to the following detailed description and the attached drawing.

The term "allelic variant" is used herein to denote any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

"Corresponding to", when used in reference to a nucleotide or amino acid sequence, indicates the position in a second sequence that aligns with the reference position when two sequences are optimally aligned.

The term "expression vector" is used to denote a DNA molecule, linear or circular, that comprises a segment encoding a polypeptide of interest operably linked to additional segments that provide for its transcription. Such additional segments include promoter and terminator sequences, and may also include one or more origins of replication, one or more selectable markers, an enhancer, a polyadenylation signal, etc. Expression vectors are generally derived from plasmid or viral DNA, or may contain elements of both.

The term "isolated", when applied to a polynucleotide, denotes that the polynucleotide has been removed from its natural genetic milieu and is thus free of other extraneous or unwanted coding sequences, and is in a form suitable for use within genetically engineered protein production systems.

"Operably linked", when referring to DNA segments, indicates that the segments are arranged so that they function in concert for their intended purposes, e.g. transcription initiates in the promoter and proceeds through the coding segment to the terminator.

A "polynucleotide" is a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules.

The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes.

The term "receptor" is used herein to denote a cell-associated protein, or a polypeptide subunit of such a protein, that binds to a bioactive molecule (the "ligand") and mediates the effect of the ligand on the cell. Binding of ligand to receptor results in a conformational change in the receptor (and, in some cases, receptor multimerization, i.e., association of identical or different receptor subunits) that causes interactions between the effector domain(s) and other molecule(s) in the cell. These interactions in turn lead to alterations in the metabolism of the cell. Metabolic events that are linked to receptor-ligand interactions include gene transcription, phosphorylation, dephosphorylation, cell proliferation, increases in cyclic AMP production, mobilization of cellular calcium, mobilization of membrane lipids, cell adhesion, hydrolysis of inositol lipids and hydrolysis of phospholipids. The term "receptor polypeptide" is used to denote complete receptor polypeptide chains and portions thereof, including isolated functional domains (e.g., ligand-binding domains).

A "secretory signal sequence" is a DNA sequence that encodes a polypeptide (a "secretory peptide") that, as a component of a larger polypeptide, directs the larger polypeptide through a secretory pathway of a cell in which it is synthesized.

The larger polypeptide is commonly cleaved to remove the secretory peptide during transit through the secretory pathway.

A "soluble receptor" is a receptor polypeptide that is not bound to a cell membrane. Soluble receptors are most commonly ligand-binding receptor polypeptides that lack transmembrane and cytoplasmic domains. Soluble receptors can comprise additional amino acid residues, such as affinity tags that provide for purification of the polypeptide or provide sites for attachment of the polypeptide to a substrate, or immunoglobulin constant region sequences. Many cell-surface receptors have naturally occurring, soluble counterparts that are produced by proteolysis or translated from alternatively spliced mRNAs. Receptor polypeptides are said to be substantially free of transmembrane and intracellular polypeptide segments when they lack sufficient portions of these segments to provide membrane anchoring or signal transduction, respectively.

The term "splice variant" is used herein to denote alternative forms of RNA transcribed from a gene. Splice variation arises naturally through use of alternative splicing sites within a transcribed RNA molecule, or less commonly between separately transcribed RNA molecules, and may result in several mRNAs transcribed from the same gene. Splice variants may encode polypeptides having altered amino acid sequence. The term splice variant is also used herein to denote a protein encoded by a splice variant of an mRNA transcribed from a gene.

Molecular weights and lengths of polymers determined by imprecise analytical methods (e.g., gel electrophoresis) will be understood to be approximate values. When such a value is expressed as "about" X or "approximately" X, the stated value of X will be understood to be accurate to ±10%.

Cytokine receptors subunits are characterized by a multi-domain structure comprising a ligand-binding domain and an effector domain that is typically involved in signal transduction. Multimeric cytokine receptors include homodimers (e.g., PDGF receptor αα and ββ isoforms, erythropoietin receptor, MPL (thrombopoietin receptor), and G-CSF receptor), heterodimers whose subunits each have ligand-binding and effector domains (e.g., PDGF receptor αβ isoform), and multimers having component subunits with disparate functions (e.g., IL-2, IL-3, IL-4, IL-5, IL-6, IL-7, and GM-CSF receptors). Some receptor subunits are common to a plurality of receptors. For example, the AIC2B subunit, which cannot bind ligand on its own but includes an intracellular signal transduction domain, is a component of IL-3 and GM-CSF receptors. Many cytokine receptors can be placed into one of four related families on the basis of their structures and functions. Class I hematopoietic receptors, for example, are characterized by the presence of a domain containing conserved cysteine residues and the WSXWS motif. Additional domains, including protein kinase domains; fibronectin type III domains; and immunoglobulin domains, which are characterized by disulfide-bonded loops, are present in certain hematopoietic receptors. Cytokine receptor structure has been reviewed by Urdal, *Ann. Reports Med. Chem.* 26:221–228, 1991 and Cosman, *Cytokine* 5:95–106, 1993. It is generally believed that under selective pressure for organisms to acquire new biological functions, new receptor family members arose from duplication of existing receptor genes leading to the existence of multi-gene families. Family members thus contain vestiges of the ancestral gene, and these characteristic features can be exploited in the isolation and identification of additional family members.

Cell-surface cytokine receptors are further characterized by the presence of additional domains. These receptors are anchored in the cell membrane by a transmembrane domain characterized by a sequence of hydrophobic amino acid residues (typically about 21–25 residues), which is commonly flanked by positively charged residues (Lys or Arg). On the opposite end of the protein from the extracellular domain and separated from it by the transmembrane domain is an intracellular domain.

The Zcytor11 receptor is a class II cytokine receptor. These receptors usually bind to four-helix-bundle cytokines. Interleukin-10 and the interferons have receptors in this class (e.g., interferon-gamma alpha and beta chains and the interferon-alpha/beta receptor alpha and beta chains). Class II cytokine receptors are characterized by the presence of one or more cytokine receptor modules (CRM) in their extracellular domains. The CRMs of class II cytokine receptors are somewhat different than the better known CRMs of class I cytokine receptors. While the class II CRMs contain two type-III fibronectin-like domains, they differ in organization.

Zcytor11, like all known class II receptors except interferon-alpha/beta receptor alpha chain, has only a single class II CRM in its extracellular domain. Zcytor11 is a receptor for a helical cytokine of the interferon/IL-10 class. As was stated above, Zcytor11 is similar to the interferon α receptor α chain. Uze et al. *Cell* 60 255–264 (1996) Analysis of a human cDNA clone encoding Zcytor11 (SEQ ID NO:1) revealed an open reading frame encoding 574 amino acids (SEQ ID NO:2) comprising an extracellular ligand-binding domain of approximately 211 amino acid residues (residues 18–228 of SEQ ID NO:2; SEQ ID NO:3), a transmembrane domain of approximately 23 amino acid residues (residues 229–251 of SEQ ID NO:2), and an intracellular domain of approximately 313 amino acid residues (residues 252 to 574 of SEQ ID NO:2). Those skilled in the art will recognize that these domain boundaries are approximate and are based on alignments with known proteins and predictions of protein folding. Deletion of residues from the ends of the domains is possible.

Moreover, the zcytor11 receptor has been shown to bind a ligand called T-cell inducible Factor (TIF, or IL-TIF) (See, WIPO publication WO 00/24758; Dumontier et al., *J. Immunol.* 164:1814–1819, 2000; and Xie et al., *J. Biol. Chem. manuscript in press M*005304200). The human IL-TIF nucleotide sequence is represented in SEQ ID NO:7 and corresponding polypeptide sequence is shown in SEQ ID NO:8. Within preferred embodiments, the soluble receptor form of zcytor11, residues 18–228 of SEQ ID NO:2, (SEQ ID NO:3) is a homodimer, heterodimer, or multimer that antagonizes the effects of IL-TIF in vivo. Antibodies to such homodimer, heterodimer, or multimers also serve as antagonists of IL-TIF activity.

IL-TIF has been shown to be induced in the presence of IL-9, and is suspected to be involved in promoting Th1-type immune responses. IL-9 stimulates proliferation, activation, differentiation and/or induction of immune function in a variety of ways and is implicated in asthma, lung mastocytosis, and other diseases, as well as activate STAT pathways. Antagonists of IL-TIF or IL-9 function can have beneficial use against such human diseases. The present invention provides such novel antagonists of IL-TIF.

The present invention is based in part upon the discovery of a novel heterodimeric soluble receptor protein having the structure of a class II cytokine receptor, and antibodies thereto. The heterodimeric soluble receptor includes at least one zcytor11 soluble receptor subunit, disclosed in the commonly owned U.S. Pat. No. 5,965,704. A second soluble receptor polypeptide included in the heterodimeric soluble receptor belongs to the receptor subfamily that includes Interleukin-10 (Liu Y et al, *J. Immunol.* 152; 1821–1829, 1994 (IL-10R cDNA) (SEQ ID NO:34)), the interferons (e.g., interferon-gamma alpha and beta chains and the interferon-alpha/beta receptor alpha and beta chains), CRF2-4 (Genbank Accession No. Z17227; SEQ ID NO:33), and DIRS1 (WIPO Publication WO99/46379, Schering Corporation, 1999; SEQ ID NO:35). The zcytor11 receptor in conjunction with CRF2-4 and IL-10 Receptor was shown to signal JAK-STAT pathway in response to the natural ligand for the zcytor11 receptor, IL-TIF (Xie et al., supra.). According to the present invention, a heterodimeric soluble zcytor11 receptor, as exemplified by a preferred embodiment of a soluble zcytor11 receptor+soluble CRF2-4 receptor heterodimer (zcytor11/CRF2-4), can act as a potent antagonist of the IL-TIF. Other embodiments include soluble heterodimer zcytor11/IL-10R, zcytor11/IL-9R, and other class II receptor subunits, as well as multimeric receptors including but not limited to zcytor11/CRF2-4/IL-10R, and zcytor11/CRF2-4/IL-9R.

Analysis of the tissue distribution of the mRNA corresponding zcytor11 cDNA showed that mRNA level was highest in pancreas, followed by a much lower levels in thymus, colon, liver, skin, lung, kidney and small intestine. Thus, particular embodiments of the present invention are directed toward use of soluble zcytor11 heterodimers as antagonists in inflammatory and immune diseases or conditions such as pancreatitis, type I diabetes (IDDM), pancreatic cancer, pancreatitis, Graves Disease, inflammatory bowel disease (IBD), Crohn's Disease, colon and intestinal cancer, diverticulosis, autoimmune disease, sepsis, asthma, end-stage renal diseases, psoriasis, organ or bone marrow transplant; and where inhibition of inflammation, immune suppression, reduction of proliferation of hematopoietic, immune, inflammatory or lymphoid cells, macrophages, T-cells (including Th1 and Th2 cells), suppression of immune response to a pathogen or antigen, or inhibition of IL-TIF or IL-9 cytokine production is desired.

Moreover, antibodies recognizing zcytoR11, soluble zcytoR11/CRF2-4 heterodimers, and multimers described herein and/or soluble zcytoR11/CRF2-4 heterodimers, and multimers themselves are useful to:

1) Antagonize or block signaling via the IL-TIF receptors in the treatment of autoimmune diseases such as IDDM, multiple sclerosis (MS), systemic Lupus erythematosus (SLE), myasthenia gravis, rheumatoid arthritis, and IBD to prevent or inhibit signaling in immune cells (e.g. lymphocytes, monocytes, leukocytes) via zcytoR11 (Hughes C et al., *J. Immunol* 153: 3319–3325, 1994). Alternatively anti-soluble zcytor11, anti-soluble zcytoR11/CRF2-4 heterodimer or mulitmer monoclonal antibody (Mab) can be used as an antagonist to deplete unwanted immune cells to treat autoimmune disease. Asthma, allergy and other atopic disease may be treated with an MAb against soluble zcytor11 soluble zcytoR11/CRF2-4 heterodimers to inhibit the immune response or to deplete offending cells. Blocking or inhibiting signaling via zcytoR11, using the polypeptides and antibodies of the present invention, may also benefit diseases of the pancreas, kidney, pituitary and neuronal cells. IDDM, NIDDM, pancreatitis, and pancreatic carcinoma may benefit. ZcytoR11 may serve as a target for MAb therapy of cancer where an antagonizing MAb inhibits cancer growth and targets immune-mediated killing. (Holliger P, and Hoogenboom, H: *Nature Biotech.* 16: 1015–1016, 1998). Mabs to soluble zcytoR11, and soluble zcytoR11/CRF2-4 heterodimers and multimers may also be useful to treat nephropathies such as glomerulosclerosis, membranous neuropathy, amyloidosis (which also affects the kidney among other tissues), renal arteriosclerosis, glomerulonephritis of various origins, fibroproliferative diseases of the kidney, as well as kidney dysfunction associated with SLE, IDDM, type II diabetes (NIDDM), renal tumors and other diseases.

2) Agonize or initiate signaling via the IL-TIF receptors in the treatment of autoimmune diseases such as IDDM, MS, SLE, myasthenia gravis, rheumatoid arthritis, and IBD. Anti-soluble zcytor11, anti-soluble zcytoR11/CRF2-4 heterodimers and multimer monoclonal antibodies may signal lymphocytes or other immune cells to differentiate, alter proliferation, or change production of cytokines or cell surface proteins that ameliorate autoimmunity. Specifically, modulation of a T-helper cell response to an alternate pattern of cytokine secretion may deviate an autoimmune response to ameliorate disease (Smith JA et al., *J. Immunol.* 160: 4841–4849, 1998). Similarly, agonistic Anti-soluble zcytor11, anti-solublezcytoR11/CRF2-4 heterodimers and multimer monoclonal antibodies may be used to signal, deplete and deviate immune cells involved in asthma, allergy and atopoic disease. Signaling via zcytoR11 may also benefit diseases of the pancreas, kidney, pituitary and neuronal cells. IDDM, NIDDM, pancreatitis, and pancreatic carcinoma may benefit. ZcytoR11 may serve as a target for MAb therapy of pancreatic cancer where a signaling MAb inhibits cancer growth and targets immune-mediated killing (Tutt, A L et al., *J Immunol.* 161: 3175–3185, 1998). Similarly renal cell carcinoma may be treated with monoclonal antibodies to zcytor11-comprising soluble receptors of the present invention.

Soluble zcytor11, soluble zcytoR11/CRF2-4 heterodimers and multimers described herein can be used to neutralize/block IL-TIF activity in the treatment of autoimmune disease, atopic disease, NIDDM, pancreatitis and kidney dysfunction as described above. A soluble form of zcytoR11 may be used to promote an antibody response mediated by Th cells and/or to promote the production of IL-4 or other cytokines by lymphocytes or other immune cells.

The soluble receptors of the present invention are useful as antagonists of the IL-TIF cytokine. Such antagonistic effects can be achieved by direct neutralization or binding of the IL-TIF. In addition to antagonistic uses, the soluble receptors of the present invention can bind IL-TIF and act as carrier proteins for the IL-TIF cytokine, in order to transport the Ligand to different tissues, organs, and cells within the body. As such, the soluble receptors of the present invention can be fused or coupled to molecules, polypeptides or chemical moieties that direct the soluble-receptor-Ligand complex to a specific site, such as a tissue, specific immune cell, or tumor. Thus, the soluble receptors of the present invention can be used to specifically direct the action of the IL-TIF. See, Cosman, D. *Cytokine* 5: 95–106, 1993; and Fernandez-Botran, R. *Exp. Opin. Invest. Drugs* 9:497–513, 2000.

Moreover, the soluble receptors of the present invention can be used to stabilize the IL-TIF, to increase the bioavailability, therapeutic longevity, and/or efficacy of the Ligand by stabilizing the Ligand from degradation or clearance, or by targeting the ligand to a site of action within the body. For example the naturally occurring IL-6/soluble IL-6R complex stabilizes IL-6 and can signal through the gp130 receptor. See, Cosman, D. supra., and Femandez-Botran, R. supra.

Within preferred embodiments of the invention the isolated polynucleotides will hybridize to similar sized regions of nucleotides SEQ ID NO:1 corresponding to SEQ ID NO:3 or a sequence complementary thereto, under stringent conditions. In general, stringent conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Typical stringent conditions are those in which the salt concentration is at least about 0.02 M at pH 7 and the temperature is at least about 60° C. As previously noted, the isolated polynucleotides of the present invention include DNA and RNA. Methods for isolating DNA and RNA are well known in the art. It is generally preferred to isolate RNA from pancreas or prostate tissues although cDNA can also be prepared using RNA from other tissues or isolated as genomic DNA. Total RNA can be prepared using guanidine HCl extraction followed by isolation by centrifugation in a CsCl gradient (Chirgwin et al., *Biochemistry* 18:52–94, (1979)). Poly $(A)^+$ RNA is prepared from total RNA using the method of Aviv and Leder *Proc. Natl. Acad. Sci. USA* 69:1408–1412, (1972). Complementary DNA (cDNA) is prepared from poly$(A)^+$ RNA using known methods. Polynucleotides encoding Zcytor11 polypeptides are then identified and isolated by, for example, hybridization or PCR.

Those skilled in the art will recognize that the sequences disclosed in SEQ ID NO:3 and the corresponding nucleotides of SEQ ID NO:1 and represent single alleles of the human Zcytor11 receptor. Allelic variants of these sequences can be cloned by probing cDNA or genomic libraries from different individuals according to standard procedures.

The present invention further provides counterpart receptors and polynucleotides from other species ("species orthologs"). Of particular interest are Zcytor11 receptors from other mammalian species, including murine, porcine, ovine, bovine, canine, feline, equine, and non-human primates. Species orthologs of the human Zcytor11 receptor can be cloned using information and compositions provided by the present invention in combination with conventional cloning techniques. For example, a cDNA can be cloned using mRNA obtained from a tissue or cell type that expresses the receptor. Suitable sources of mRNA can be identified by probing Northern blots with probes designed from the sequences disclosed herein. A library is then prepared from mRNA of a positive tissue or cell line. A receptor-encoding cDNA can then be isolated by a variety of methods, such as by probing with a complete or partial cDNA of human and other primates or with one or more sets of degenerate probes based on the disclosed sequences. A cDNA can also be cloned using the polymerase chain reaction, or PCR (Mullis, U.S. Pat. No. 4,683,202), using primers designed from the sequences disclosed herein. Within an additional method, the cDNA library can be used to transform or transfect host cells, and expression of the cDNA of interest can be detected with an antibody to the receptor. Similar techniques can also be applied to the isolation of genomic clones.

The present invention also provides isolated soluble monomeric, homodimeric, heterodimeric and multimeric receptor polypeptides that comprise at least one zcytor11 receptor subunit that is substantially homologous to the receptor polypeptide of SEQ ID NO:3. By "isolated" is meant a protein or polypeptide that is found in a condition other than its native environment, such as apart from blood and animal tissue. In a preferred form, the isolated polypeptide is substantially free of other polypeptides, particularly other polypeptides of animal origin. It is preferred to provide the polypeptides in a highly purified form, i.e. greater than 95% pure, more preferably greater than 99% pure. The term "substantially homologous" is used herein to denote polypeptides having 50%, preferably 60%, more preferably at least 80%, sequence identity to the sequences shown in SEQ ID NO:3. Such polypeptides will more preferably be at least 90% identical, and most preferably 95% or more identical to SEQ ID NO:3. Percent sequence identity is determined by conventional methods. See, for example, Altschul et al., *Bull. Math. Bio.* 48: 603–616, (1986) and Henikoff and Henikoff, *Proc. Natl. Acad. Sci. USA* 89:10915–10919, (1992). Briefly, two amino acid sequences are aligned to optimize the alignment scores using a gap opening penalty of 10, a gap extension penalty of 1, and the "blossom 62" scoring matrix of Henikoff and Henikoff (id.) as shown in Table 2 (amino acids are indicated by the standard one-letter codes). The percent identity is then calculated as:

$$\frac{\text{Total number of identical matches}}{\left[\begin{array}{c}\text{length of the longer sequence plus the}\\ \text{number of gaps introduced into the longer}\\ \text{sequence in order to align the two sequences}\end{array}\right]}\times 100$$

TABLE 2

| | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | −1 | 5 | | | | | | | | | | | | | | | | | | |
| N | −2 | 0 | 6 | | | | | | | | | | | | | | | | | |
| D | −2 | −2 | 1 | 6 | | | | | | | | | | | | | | | | |
| C | 0 | −3 | −3 | −3 | 9 | | | | | | | | | | | | | | | |
| Q | −1 | 1 | 0 | 0 | −3 | 5 | | | | | | | | | | | | | | |
| E | −1 | 0 | 0 | 2 | −4 | 2 | 5 | | | | | | | | | | | | | |
| G | 0 | −2 | 0 | −1 | −3 | −2 | −2 | 6 | | | | | | | | | | | | |
| H | −2 | 0 | 1 | −1 | −3 | 0 | 0 | −2 | 8 | | | | | | | | | | | |
| I | −1 | −3 | −3 | −3 | −1 | −3 | −3 | −4 | −3 | 4 | | | | | | | | | | |
| L | −1 | −2 | −3 | −4 | −1 | −2 | −3 | −4 | −3 | 2 | 4 | | | | | | | | | |
| K | −1 | 2 | 0 | −1 | −3 | 1 | 1 | −2 | −1 | −3 | −2 | 5 | | | | | | | | |
| M | −1 | −1 | −2 | −3 | −1 | 0 | −2 | −3 | −2 | 1 | 2 | −1 | 5 | | | | | | | |
| F | −2 | −3 | −3 | −3 | −2 | −3 | −3 | −3 | −1 | 0 | 0 | −3 | 0 | 6 | | | | | | |
| P | −1 | −2 | −2 | −1 | −3 | −1 | −1 | −2 | −2 | −3 | −3 | −1 | −2 | −4 | 7 | | | | | |
| S | 1 | −1 | 1 | 0 | −1 | 0 | 0 | 0 | −1 | −2 | −2 | 0 | −1 | −2 | −1 | 4 | | | | |
| T | 0 | −1 | 0 | −1 | −1 | −1 | −1 | −2 | −2 | −1 | −1 | −1 | −1 | −2 | −1 | 1 | 5 | | | |
| W | −3 | −3 | −4 | −4 | −2 | −2 | −3 | −2 | −2 | −3 | −2 | −3 | −1 | 1 | −4 | −3 | −2 | 11 | | |
| Y | −2 | −2 | −2 | −3 | −2 | −1 | −2 | −3 | 2 | −1 | −1 | −2 | −1 | 3 | −3 | −2 | −2 | 2 | 7 | |
| V | 0 | −3 | −3 | −3 | −1 | −2 | −2 | −3 | −3 | 3 | 1 | −2 | 1 | −1 | −2 | −2 | 0 | −3 | −1 | 4 |

Sequence identity of polynucleotide molecules is determined by similar methods using a ratio as disclosed above.

Those skilled in the art appreciate that there are many established algorithms available to align two amino acid sequences. The "FASTA" similarity search algorithm of Pearson and Lipman is a suitable protein alignment method for examining the level of identity shared by an amino acid sequence disclosed herein and the amino acid sequence of a putative variant ztryp1. The FASTA algorithm is described by Pearson and Lipman, *Proc. Nat'l Acad. Sci. USA* 85:2444 (1988), and by Pearson, *Meth. Enzymol.* 183:63 (1990).

Briefly, FASTA first characterizes sequence similarity by identifying regions shared by the query sequence (e.g., SEQ ID NO:3) and a test sequence that have either the highest density of identities (if the ktup variable is 1) or pairs of identities (if ktup=2), without considering conservative amino acid substitutions, insertions, or deletions. The ten regions with the highest density of identities are then rescored by comparing the similarity of all paired amino acids using an amino acid substitution matrix, and the ends of the regions are "trimmed" to include only those residues that contribute to the highest score. If there are several regions with scores greater than the "cutoff" value (calculated by a predetermined formula based upon the length of the sequence and the ktup value), then the trimmed initial regions are examined to determine whether the regions can be joined to form an approximate alignment with gaps. Finally, the highest scoring regions of the two amino acid sequences are aligned using a modification of the Needleman-Wunsch-Sellers algorithm (Needleman and Wunsch, *J. Mol. Biol.* 48:444 (1970); Sellers, *SIAM J. Appl. Math.* 26:787 (1974)), which allows for amino acid insertions and deletions. Preferred parameters for FASTA analysis are: ktup=1, gap opening penalty=10, gap extension penalty=1, and substitution matrix=BLOSUM62. These parameters can be introduced into a FASTA program by modifying the scoring matrix file ("SMATRIX"), as explained in Appendix 2 of Pearson, *Meth. Enzymol.*, supra.

FASTA can also be used to determine the sequence identity of nucleic acid molecules using a ratio as disclosed above. For nucleotide sequence comparisons, the ktup value can range between one to six, preferably from three to six, most preferably three, with other FASTA program parameters set as default.

The BLOSUM62 table (Table 2) is an amino acid substitution matrix derived from about 2,000 local multiple alignments of protein sequence segments, representing highly conserved regions of more than 500 groups of related proteins (Henikoff and Henikoff, *Proc. Nat'l Acad. Sci. USA* 89:10915 (1992)). Accordingly, the BLOSUM62 substitution frequencies can be used to define conservative amino acid substitutions that may be introduced into the amino acid sequences of the present invention. Although it is possible to design amino acid substitutions based solely upon chemical properties (as discussed below), the language "conservative amino acid substitution" preferably refers to a substitution represented by a BLOSUM62 value of greater than −1. For example, an amino acid substitution is conservative if the substitution is characterized by a BLOSUM62 value of 0, 1, 2, or 3. According to this system, preferred conservative amino acid substitutions are characterized by a BLOSUM62 value of at least 1 (e.g., 1, 2 or 3), while more preferred conservative amino acid substitutions are characterized by a BLOSUM62 value of at least 2 (e.g., 2 or 3).

Substantially homologous proteins and polypeptides are characterized as having one or more amino acid substitutions, deletions or additions. These changes are preferably of aminor nature, that is conservative amino acid substitutions (see Table 3) and other substitutions that do not significantly affect the folding or activity of the protein or polypeptide; small deletions, typically of one to about 30 amino acids; and small amino- or carboxyl-terminal extensions, such as an amino-terminal methionine residue, a small linker peptide of up to about 20–25 residues, or a small extension that facilitates purification (an affinity tag), such as a polyhistidine tract, protein A (Nilsson et al., *EMBO J.* 4:1075, (1985); Nilsson et al., *Methods Enzymol.* 198:3, (1991)), glutathione S transferase (Smith and Johnson, *Gene* 67:31, 1988), or other antigenic epitope or binding domain. See, in general Ford et al., *Protein Expression and Purification* 2: 95–107, (1991. DNAs encoding affinity tags are available from commercial suppliers (e.g., Pharmacia Biotech, Piscataway, N.J.).

TABLE 3

| Conservative amino acid substitutions | |
|---|---|
| Basic: | arginine<br>lysine<br>histidine |
| Acidic: | glutamic acid<br>aspartic acid |
| Polar: | glutamine<br>asparagine |
| Hydrophobic: | leucine<br>isoleucine<br>valine |
| Aromatic: | phenylalanine<br>tryptophan<br>tyrosine |
| Small: | glycine<br>alanine<br>serine<br>threonine<br>methionine |

Essential amino acids in the receptor polypeptides of the present invention can be identified according to procedures known in the art, such as site-directed mutagenesis or alanine-scanning mutagenesis (Cunningham and Wells, *Science* 244, 1081–1085, (1989); Bass et al., *Proc. Natl. Acad. Sci. USA* 88:4498–4502, (1991)). In the latter technique, single alanine mutations are introduced at every residue in the molecule, and the resultant mutant molecules are tested for biological activity (e.g., ligand binding and signal transduction) to identify amino acid residues that are critical to the activity of the molecule. Sites of ligand-receptor interaction can also be determined by analysis of crystal structure as determined by such techniques as nuclear magnetic resonance, crystallography or photoaffinity labeling. See, for example, de Vos et al., *Science* 255:306–312, (1992); Smith et al., *J. Mol. Biol.* 224:899–904, (1992); Wlodaver et al., *FEBS Lett.* 309:59–64, (1992). The identities of essential amino acids can also be inferred from analysis of homologies with related receptors.

Multiple amino acid substitutions can be made and tested using known methods of mutagenesis and screening, such as those disclosed by Reidhaar-Olson and Sauer *Science* 241: 53–57, (1988) or Bowie and Sauer *Proc. Natl. Acad. Sci. USA* 86:2152–2156, (1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display e.g., Lowman et al., *Biochem.* 30:10832–10837, (1991); Ladner et al., U.S. Pat. No. 5,223,409; Huse, WIPO Publication WO 92/06204) and region-directed mutagenesis (Derbyshire et al., *Gene* 46:145, (1986); Ner et al., *DNA* 7:127, (1988)).

Mutagenesis methods as disclosed above can be combined with high-throughput screening methods to detect activity of cloned, mutagenized receptors in host cells. Preferred assays in this regard include cell proliferation assays and biosensor-based ligand-binding assays, which are described below. Mutagenized DNA molecules that encode active receptors or portions thereof (e.g., ligand-binding fragments) can be recovered from the host cells and rapidly sequenced using modern equipment. These methods allow the rapid determination of the importance of individual amino acid residues in a polypeptide of interest, and can be applied to polypeptides of unknown structure.

Using the methods discussed above, one of ordinary skill in the art can prepare a variety of polypeptides that comprise a soluble receptor subunit that is substantially homologous to SEQ ID NO:3 or allelic variants thereof and retain the ligand-binding properties of the wild-type receptor. Such polypeptides may include additional amino acids from an extracellular ligand-binding domain of a Zcytor11 receptor as well as part or all of the transmembrane and intracellular domains. Such polypeptides may also include additional polypeptide segments as generally disclosed above.

The receptor polypeptides of the present invention, including soluble homodimeric, heterodimeric and multimeric receptors, full-length receptors, receptor fragments (e.g. ligand-binding fragments), and fusion polypeptides can be produced in genetically engineered host cells according to conventional techniques. Suitable host cells are those cell types that can be transformed or transfected with exogenous DNA and grown in culture, and include bacteria, fungal cells, and cultured higher eukaryotic cells. Eukaryotic cells, particularly cultured cells of multicellular organisms, are preferred. Techniques for manipulating cloned DNA molecules and introducing exogenous DNA into a variety of host cells are disclosed by Sambrook et al., *Molecular Cloning: A Laboratory Manual,* 2nd ed., Cold Spring Harbor Laboratory Press, Cold Spring Harbor, N.Y., (1989), and Ausubel et al., ibid., which are incorporated herein by reference.

In general, a DNA sequence encoding a Zcytor11 soluble receptor polypeptide, or a DNA sequence encoding an additional subunit of a heterodimeric or multimeric Zcytor11 soluble receptor, e.g., CRF2-4 or IL10R, polypeptide is operably linked to other genetic elements required for its expression, generally including a transcription promoter and terminator, within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers. Multiple components of a soluble receptor complex can be co-transfected on individual expression vectors or be contained in a single expression vector. Such techniques of expressing multiple components of protein complexes are well known in the art.

To direct a homodimeric, heterodimeric and multimeric Zcytor11 receptor polypeptide into the secretory pathway of a host cell, a secretory signal sequence (also known as a leader sequence, prepro sequence or pre sequence) is provided in the expression vector. The secretory signal sequence may be that of the receptor, or may be derived from another secreted protein (e.g., t-PA) or synthesized de novo. The secretory signal sequence is joined to the Zcytor11 DNA sequence in the correct reading frame. Secretory signal sequences are commonly positioned 5' to the DNA sequence encoding the polypeptide of interest, although certain signal sequences may be positioned elsewhere in the DNA sequence of interest (see, e.g., Welch et al., U.S. Pat. No. 5,037,743; Holland et al., U.S. Pat. No. 5,143,830).

Cultured mammalian cells are preferred hosts within the present invention. Methods for introducing exogenous DNA into mammalian host cells include calcium phosphate-mediated transfection (Wigler et al., *Cell* 14:725, (1978); Corsaro and Pearson, *Somatic Cell Genetics* 7:603, (1981): Graham and Van der Eb, *Virology* 52:456, (1973)), electroporation (Neumann et al., *EMBO J.* 1:841–845, (1982)), DEAE-dextran mediated transfection (Ausubel et al., eds., *Current Protocols in Molecular Biology*, (John Wiley and Sons, Inc., NY, 1987), and liposome-mediated transfection (Hawley-Nelson et al., *Focus* 15:73, (1993); Ciccarone et al., *Focus* 15:80, (1993)), which are incorporated herein by reference. The production of recombinant polypeptides in cultured mammalian cells is disclosed, for example, by Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134. Suitable cultured mammalian cells include the COS-1 (ATCC No. CRL 1650), COS-7 (ATCC No. CRL 1651), BHK (ATCC No. CRL 1632), BHK 570 (ATCC No. CRL 10314), 293 (ATCC No. CRL 1573; Graham et al., *J. Gen. Virol.* 36:59–72, 1977) and Chinese hamster ovary (e.g. CHO-K1; ATCC No. CCL 61) cell lines. Additional suitable cell lines are known in the art and available from public depositories such as the American Type Culture Collection, Rockville, Md. In general, strong transcription promoters are preferred, such as promoters from SV-40 or cytomegalovirus. See, e.g., U.S. Pat. No. 4,956,288. Other suitable promoters include those from metallothionein genes (U.S. Pat. Nos. 4,579,821 and 4,601,978) and the adenovirus major late promoter.

Drug selection is generally used to select for cultured mammalian cells into which foreign DNA has been inserted. Such cells are commonly referred to as "transfectants". Cells that have been cultured in the presence of the selective agent and are able to pass the gene of interest to their progeny are referred to as "stable transfectants." A preferred selectable marker is a gene encoding resistance to the antibiotic neomycin. Selection is carried out in the presence of a neomycin-type drug, such as G-418 or the like. Selection systems may also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. A preferred amplifiable selectable marker is dihydrofolate reductase, which confers resistance to methotrexate. Other drug resistance genes (e.g. hygromycin resistance, multi-drug resistance, puromycin acetyltransferase) can also be used.

Other higher eukaryotic cells can also be used as hosts, including insect cells, plant cells and avian cells. Transformation of insect cells and production of foreign polypeptides therein is disclosed by Guarino et al., U.S. Pat. No. 5,162,222; Bang et al., U.S. Pat. No. 4,775,624; and WIPO publication WO 94/06463, which are incorporated herein by reference. The use of *Agrobacterium rhizogenes* as a vector for expressing genes in plant cells has been reviewed by Sinkar et al., *J. Biosci*. (*Bangalore*) 11:47–58, (1987).

Fungal cells, including yeast cells, and particularly cells of the genus *Saccharomyces*, can also be used within the present invention, such as for producing receptor fragments or polypeptide fusions. Methods for transforming yeast cells with exogenous DNA and producing recombinant polypeptides therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075. Transformed cells are selected by phenotype determined by the selectable marker, commonly drug resistance or the ability to grow in the absence of a particular nutrient (e.g., leucine). A preferred vector system for use in yeast is the POT1 vector system disclosed by Kawasaki et al. (U.S. Pat. No. 4,931,373), which allows transformed cells to be selected by growth in glucose-containing media. Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977,092) and alcohol dehydrogenase genes. See also U.S. Pat. Nos. 4,990,446; 5,063,154; 5,139,936 and 4,661,454. Transformation systems for other yeasts, including *Hansenula polymorpha, Schizosaccharomyces pombe, Kluyveromyces lactis, Kluyveromyces fragilis, Ustilago maydis, Pichia pastoris, Pichia methanolica, Pichia guillermondii* and *Candida maltosa* are known in the art. See, for example, Gleeson et al., *J. Gen. Microbiol.* 132:3459–3465, (1986) and Cregg, U.S. Pat. No. 4,882,279. *Aspergillus* cells may be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming Neurospora are disclosed by Lambowitz, U.S. Pat. No. 4,486,533.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell.

Within one aspect of the present invention, a novel soluble receptor of the present invention is produced by a cultured cell, and the cell is used to screen for ligands for the receptor, including the natural ligand, IL-TIF, as well as agonists and antagonists of the natural ligand. To summarize this approach, a cDNA or gene encoding the receptor is combined with other genetic elements required for its expression (e.g., a transcription promoter), and the resulting expression vector is inserted into a host cell. Cells that express the DNA and produce functional receptor are selected and used within a variety of screening systems. Each component of the homodimeric, heterodimeric and multimeric receptor complex can be expressed in the same cell.

Mammalian cells suitable for use in expressing Zcytor11 receptors and transducing a receptor-mediated signal include cells that express other receptor subunits which may form a functional complex with Zcytor11. These subunits may include those of the interferon receptor family or of other class II or class I cytokine receptors, e.g., CRF2-4, IL-10R, and IL-9R. It is also preferred to use a cell from the same species as the receptor to be expressed. Within a preferred embodiment, the cell is dependent upon an exogenously supplied hematopoietic growth factor for its proliferation. Preferred cell lines of this type are the human TF-1 cell line (ATCC number CRL-2003) and the AML-193 cell line (ATCC number CRL-9589), which are GM-CSF-dependent human leukemic cell lines and BaF3 (Palacios and Steinmetz, *Cell* 41: 727–734, (1985)) which is an IL-3 dependent murine pre-B cell line. Other cell lines include BHK, COS-1 and CHO cells.

Suitable host cells can be engineered to produce the necessary receptor subunits or other cellular component needed for the desired cellular response. This approach is advantageous because cell lines can be engineered to express receptor subunits from any species, thereby overcoming potential limitations arising from species specificity. Species orthologs of the human receptor cDNA can be cloned and used within cell lines from the same species, such as a mouse cDNA in the BaF3 cell line. Cell lines that are dependent upon one hematopoietic growth factor, such as GM-CSF or IL-3, can thus be engineered to become dependent upon IL-TIF.

Cells expressing functional receptor are used within screening assays. A variety of suitable assays are known in the art. These assays are based on the detection of a biological response in a target cell. One such assay is a cell proliferation assay. Cells are cultured in the presence or absence of a test compound, and cell proliferation is detected by, for example, measuring incorporation of tritiated thymidine or by colorimetric assay based on the metabolic breakdown of 3-(4,5-dimethylthiazol-2-yl)-2,5-diphenyl tetrazolium bromide (MTT) (Mosman, *J. Immunol. Meth.* 65: 55–63, (1983)). An alternative assay format uses cells that are further engineered to express a reporter gene. The reporter gene is linked to a promoter element that is responsive to the receptor-linked pathway, and the assay detects activation of transcription of the reporter gene. A preferred promoter element in this regard is a serum response element, or SRE. See, e.g., Shaw et al., *Cell* 56:563–572, (1989). A preferred such reporter gene is a luciferase gene (de Wet et al., *Mol. Cell. Biol.* 7:725, (1987)). Expression of the luciferase gene is detected by luminescence using methods known in the art (e.g., Baumgartner et al., *J. Biol. Chem.* 269:29094–29101, (1994); Schenborn and Goiffin, *Promega_Notes* 41:11, 1993). Luciferase activity assay kits are commercially available from, for example, Promega Corp., Madison, Wis. Target cell lines of this type can be used to screen libraries of chemicals, cell-conditioned culture media, fungal broths, soil samples, water samples, and the like. For example, a bank of cell-conditioned media samples can be assayed on a target cell to identify cells that produce ligand. Positive cells are then used to produce a cDNA library in a mammalian expression vector, which is divided into pools, transfected into host cells, and expressed. Media samples from the transfected cells are then assayed, with subsequent division of pools, re-transfection, subculturing, and re-assay of positive cells to isolate a cloned cDNA encoding the ligand.

A natural ligand for the Zcytor11 receptor can also be identified by mutagenizing a cell line expressing the full-length receptor and culturing it under conditions that select for autocrine growth. See WIPO publication WO 95/21930. Within a typical procedure, IL-3 dependent BaF3 cells expressing Zcytor11 and the necessary additional subunits are mutagenized, such as with 2-ethylmethanesulfonate (EMS). The cells are then allowed to recover in the presence of IL-3, then transferred to a culture medium lacking IL-3 and IL-4. Surviving cells are screened for the production of a IL-TIF, such as by adding soluble receptor to the culture medium or by assaying conditioned media on wild-type BaF3 cells and BaF3 cells expressing the receptor. Using this method, cells and tissues expressing IL-TIF can be identified.

An additional screening approach provided by the present invention includes the use of hybrid receptor polypeptides. These hybrid polypeptides fall into two general classes. Within the first class, the intracellular domain of Zcytor11, comprising approximately residues 252 to 574 of SEQ ID NO:2, is joined to the ligand-binding domain of a second receptor. It is preferred that the second receptor be a hematopoietic cytokine receptor, such as mpl receptor (Souyri et al., *Cell* 63: 1137–1147, (1990). The hybrid receptor will further comprise a transmembrane domain, which may be derived from either receptor. A DNA construct encoding the hybrid receptor is then inserted into a host cell. Cells expressing the hybrid receptor are cultured in the presence of a ligand for the binding domain and assayed for a response. This system provides a means for analyzing signal transduction mediated by Zcytor11 while using readily available ligands. This system can also be used to determine if particular cell lines are capable of responding to signals transduced by Zcytor11 heterodimers and multimers of the present invention. A second class of hybrid receptor polypeptides comprise the extracellular (ligand-binding) domain of Zcytor11 (approximately residues 18 to 228 of SEQ ID NO:2; SEQ ID NO:3) with an intracellular domain of a second receptor, preferably a hematopoietic cytokine receptor, and a transmembrane domain. Hybrid zacytor11 heterodimers and multimers of the present invention receptors of this second class are expressed in cells known to be capable of responding to signals transduced by the second receptor. Together, these two classes of hybrid receptors enable the identification of a responsive cell type for the development of an assay for detecting a IL-TIF. Moreover, such cells can be used in the presence of IL-TIF to assay the soluble receptor antagonists of the present invention in a competition-type assay. In such assay, a decrease in the proliferation or signal transduction activity of IL-TIF in the presence of a soluble receptor of the present invention demonstrates antagonistic activity. Moreover IL-TIF-soluble receptor binding assays can be used to assess whether a soluble receptor antagonizes IL-TIF activity.

Cells found to express the ligand are then used to prepare a cDNA library from which the ligand-encoding cDNA can be isolated as disclosed above. The present invention thus provides, in addition to novel receptor polypeptides, methods for cloning polypeptide ligands for the receptors.

The tissue specificity of Zcytor11 expression suggests a role in the development of the pancreas, small intestine, colon and the thymus. In view of the tissue specificity observed for this receptor, agonists (including the natural ligand) and antagonists have enormous potential in both in vitro and in vivo applications. Compounds identified as receptor agonists are useful for stimulating proliferation and development of target cells in vitro and in vivo. For example, agonist compounds are useful as components of defined cell culture media, and may be used alone or in combination with other cytokines and hormones to replace serum that is commonly used in cell culture. Agonists or antagonist may be useful in specifically regulating the growth and/or development of pancreatic, gasto-intestinal or thymic-derived cells in culture. These compounds are useful as research reagents for characterizing sites of ligand-receptor interaction. In vivo, receptor agonists or antagonists may find application in the treatment pancreatic, gastro-intestinal or thymic diseases.

Agonists or antagonists to Zcytor11 may include small families of peptides. These peptides may be identified employing affinity selection conditions that are known in the art, from a population of candidates present in a peptide library. Peptide libraries include combinatory libraries chemically synthesized and presented on solid support (Lam et al., *Nature* 354: 82–84 (1991)) or are in solution (Houghten et al., *BioTechniques* 13: 412–421, (1992)), expressed then linked to plasmid DNA (Cull et al., *Proc. Natl. Acad. Sci. USA* 89: 1865–1869 (1992)) or expressed and subsequently displayed on the surfaces of viruses or cells (Boder and Wittrup, *Nature Biotechnology* 15: 553–557(1997); Cwirla et al. *Science* 276: 1696–1699 (1997)).

Zcytor11 homodimeric, heterodimeric and multimeric may also be used within diagnostic systems for the detection of circulating levels of IL-TIF ligand. Within a related embodiment, antibodies or other agents that specifically bind to Zcytor11 soluble receptors of the present invention can be used to detect circulating receptor polypeptides. Elevated or depressed levels of ligand or receptor polypeptides may be indicative of pathological conditions, including cancer.

Zcytor11 homodimeric, heterodimeric and multimeric receptor polypeptides can be prepared by expressing a truncated DNA encoding the extracellular domain, for example, a polypeptide which contains SEQ ID NO:3 or the corresponding region of a non-human receptor. It is preferred that the extracellular domain polypeptides be prepared in a form substantially free of transmembrane and intracellular polypeptide segments. For example, the C-terminus of the receptor polypeptide may be at residue 228 of SEQ ID NO:2 or the corresponding region of an allelic variant or a non-human receptor. To direct the export of the receptor domain from the host cell, the receptor DNA is linked to a second DNA segment encoding a secretory peptide, such as a t-PA secretory peptide. To facilitate purification of the secreted receptor domain, a C-terminal extension, such as a poly-histidine tag, substance P, Flag™ peptide {Hopp et al., *Biotechnology* 6:1204–1210, (1988); available from Eastman Kodak Co., New Haven, Conn.) or another polypeptide or protein for which an antibody or other specific binding agent is available, can be fused to the receptor polypeptide. Moreover, heterodimeric and multimeric non-zcytor11 subunit extracellular cytokine binding domains are a also prepared as above.

In an alternative approach, a receptor extracellular domain of zcytor11 or other class I or II cytokine receptor component can be expressed as a fusion with immunoglobulin heavy chain constant regions, typically an $F_c$ fragment, which contains two constant region domains and a hinge region but lacks the variable region (See, Sledziewski, A Z et al., U.S. Pat. Nos. 6,018,026 and 5,750,375). The soluble zcytor11, soluble zcytor11/CRF2-4 heterodimers and multimers of the present invention include such fusions. Such fusions are typically secreted as multimeric molecules wherein the Fc portions are disulfide bonded to each other and two receptor polypeptides are arrayed in closed proximity to each other. Fusions of this type can be used to affinity purify the cognate ligand from solution, as an in vitro assay tool, to block signals in vitro by specifically titrating out ligand, and as antagonists in vivo by administering them parenterally to bind circulating ligand and clear it from the circulation. To purify ligand, a Zcytor11-Ig chimera is added to a sample containing the ligand (e.g., cell-conditioned culture media or tissue extracts) under conditions that facilitate receptor-ligand binding (typically near-physiological temperature, pH, and ionic strength). The chimera-ligand complex is then separated by the mixture using protein A, which is immobilized on a solid support (e.g., insoluble resin beads). The ligand is then eluted using conventional chemical techniques, such as with a salt or pH gradient. In the alternative, the chimera itself can be bound to a solid support, with binding and elution carried out as above. The chimeras may be used in vivo to regulate gastrointestinal, pancreatic or thymic functions. Chimeras with high binding affinity are administered parenterally (e.g., by intramuscular, subcutaneous or intravenous injection). Circulating molecules bind ligand and are cleared from circulation by normal physiological processes. For use in assays, the chimeras are bound to a support via the $F_c$ region and used in an ELISA format.

The present invention further provides a variety of other polypeptide fusions and related multimeric proteins comprising one or more polypeptide fusions. For example, a soluble zcytor11 receptor or soluble zcytor11 heterodimeric polypeptide, such as soluble zcytor11/CRF2-4 can be prepared as a fusion to a dimerizing protein as disclosed in U.S. Pat. Nos. 5,155,027 and 5,567,584. Preferred dimerizing proteins in this regard include immunoglobulin constant region domains, e.g., IgGγ1, and the human κ light chain. Immunoglobulin-soluble zcytor11 receptor or immunoglobulin-soluble zcytor11 heterodimeric polypeptide, such as immunoglobulin-soluble zcytor11/CRF2-4 fusions can be expressed in genetically engineered cells to produce a variety of multimeric zcytor11 receptor analogs. Auxiliary domains can be fused to soluble zcytor11 receptor or soluble zcytor11 heterodimeric polypeptide, such as soluble zcytor11/CRF2-4 to target them to specific cells, tissues, or macromolecules (e.g., collagen, or cells expressing the IL-TIF). A zcytor11 polypeptide can be fused to two or more moieties, such as an affinity tag for purification and a targeting domain. Polypeptide fusions can also comprise one or more cleavage sites, particularly between domains. See, Tuan et al., *Connective Tissue Research* 34:1–9, 1996.

A preferred assay system employing a ligand-binding receptor fragment uses a commercially available biosensor instrument (BIAcore™, Pharmacia Biosensor, Piscataway, N.J.), wherein the receptor fragment is immobilized onto the surface of a receptor chip. Use of this instrument is disclosed by Karlsson, *J. Immunol. Methods* 145:229–240, (1991) and Cunningham and Wells, *J. Mol. Biol.* 234:554–563, (1993). A receptor fragment is covalently attached, using amine or sulfhydryl chemistry, to dextran fibers that are attached to gold film within the flow cell. A test sample is passed through the cell. If ligand is present in the sample, it will bind to the immobilized receptor polypeptide, causing a change in the refractive index of the medium, which is detected as a change in surface plasmon resonance of the gold film. This system allows the determination of on- and off-rates, from which binding affinity can be calculated, and assessment of stoichiometry of binding.

Ligand-binding receptor polypeptides can also be used within other assay systems known in the art. Such systems include Scatchard analysis for determination of binding affinity. See, Scatchard, *Ann. NY Acad. Sci.* 51: 660–672, (1949) and calorimetric assays (Cunningham et al., *Science* 253:545–548, (1991); Cunningham et al., *Science* 254: 821–825, (1991)).

A receptor ligand-binding polypeptide can also be used for purification of 1L-TIF ligand. The receptor polypeptide is immobilized on a solid support, such as beads of agarose, cross-linked agarose, glass, cellulosic resins, silica-based resins, polystyrene, cross-linked polyacrylamide, or like materials that are stable under the conditions of use. Methods for linking polypeptides to solid supports are known in the art, and include amine chemistry, cyanogen bromide activation, N-hydroxysuccinimide activation, epoxide activation, sulfhydryl activation, and hydrazide activation. The resulting media will generally be configured in the form of a column, and fluids containing ligand are passed through the column one or more times to allow ligand to bind to the receptor polypeptide. The ligand is then eluted using changes in salt concentration or pH to disrupt ligand-receptor binding.

Moreover, soluble zcytor11 receptor or soluble zcytor11 heterodimeric receptor polypeptides, such as soluble zcytor11/CRF2-4, can be used as a "ligand sink," i.e., antagonist, to bind ligand in vivo or in vitro in therapeutic or other applications where the presence of the ligand is not desired. For example, in cancers that are expressing large amounts of bioactive IL-TIF, soluble zcytor11 receptor or soluble zcytor11 heterodimeric and multimeric receptor polypeptides, such as soluble zcytor11/CRF2-4 can be used as a direct antagonist of the ligand in vivo, and may aid in reducing progression and symptoms associated with the disease, and can be used in conjunction with other therapies (e.g., chemotherapy) to enhance the effect of the therapy in reducing progression and symptoms, and preventing relapse. Moreover, soluble zcytor11 receptor or soluble zcytor11 heterodimeric receptor polypeptides, such as soluble zcytor11/CRF2-4 can be used to slow the progression of cancers that over-express zcytor11 receptors, by binding ligand in vivo that would otherwise enhance proliferation of those cancers.

Moreover, soluble zcytor11 receptor or soluble zcytor11 heterodimeric receptor polypeptides, such as soluble zcytor11/CRF2-4 can be used in vivo or in diagnostic applications to detect IL-TF-expressing cancers in vivo or in tissue samples. For example, the soluble zcytor11 receptor or soluble zcytor11 heterodimeric receptor polypeptides, such as soluble zcytor11/CRF2-4 can be conjugated to a radiolabel or fluorescent label as described herein, and used to detect the presence of the IL-TIF in a tissue sample using an in vitro ligand-receptor type binding assay, or fluorescent imaging assay. Moreover, a radiolabeled soluble zcytor11 receptor or soluble zcytor11 heterodimeric receptor polypeptides, such as soluble zcytor11/CRF2-4 could be administered in vivo to detect Ligand-expressing solid tumors through a radio-imaging method known in the art.

Soluble zcytor11 receptor or soluble zcytor11 heterodimeric polypeptide, such as soluble zcytor11/CRF2-4 polypeptides can also be used to prepare antibodies that bind to epitopes, peptides, or polypeptides contained within the antigen. The zcytor11 polypeptide or a fragment thereof serves as an antigen (immunogen) to inoculate an animal and elicit an immune response. One of skill in the art would recognize that antigens or immunogenic epitopes can consist of stretches of amino acids within a longer polypeptide, from about 10 amino acids and up to about the entire length of the polypeptide or longer depending on the polypeptide. Suitable antigens include the zcytor11 polypeptide encoded by SEQ ID NO:3 or a contiguous 9 to 211 AA amino acid fragment thereof. Preferred peptides to use as antigens are the cytokine binding domain, disclosed herein, and zcytor11 hydrophilic peptides such as those predicted by one of skill in the art from a hydrophobicity plot, determined for example, from a Hopp/Woods hydrophilicity profile based on a sliding six-residue window, with buried G, S, and T residues and exposed H, Y, and W residues ignored, or from a Jameson-Wolf plot of SEQ ID NO:3 using a DNA*STAR program. In addition, conserved motifs, and variable regions between conserved motifs of zcytor11 soluble receptor are suitable antigens. Suitable antigens also include the zcytor11 polypeptides disclosed above in combination with another class I or II cytokine extracellular domain, such as those that form soluble zcytor11 heterodimeric polypeptides, such as soluble zcytor11/CRF2-4. Moreover, corresponding regions of the mouse soluble zcytor11 receptor polypeptide (SEQ ID NO:3) can be used to generate antibodies against the soluble mouse zcytor11 receptor. In addition Antibodies generated from this immune response can be isolated and purified as described herein. Methods for preparing and isolating polyclonal and monoclonal antibodies are well known in the art. See, for example, *Current Protocols in Immunology*, Cooligan, et al. (eds.), National Institutes of Health, John Wiley and Sons, Inc., 1995; Sambrook et al., *Molecular Cloning: A Laboratory Manual, Second Edition*, Cold Spring Harbor, N.Y., 1989; and Hurrell, J. G. R., Ed., *Monoclonal Hybridoma Antibodies: Techniques and Applications*, CRC Press, Inc., Boca Raton, Fla., 1982.

As would be evident to one of ordinary skill in the art, polyclonal antibodies can be generated from inoculating a variety of warm-blooded animals such as horses, cows, goats, sheep, dogs, chickens, rabbits, mice, and rats with a soluble zcytor11 receptor or soluble zcytor11 heterodimeric polypeptide, such as soluble zcytor11/CRF2-4 polypeptide or a fragment thereof. The immunogenicity of a zcytor11 polypeptide may be increased through the use of an adjuvant, such as alum (aluminum hydroxide) or Freund's complete or incomplete adjuvant. Polypeptides useful for immunization also include fusion polypeptides, such as fusions of zcytor11 or a portion thereof with an immunoglobulin polypeptide or with maltose binding protein. The polypeptide immunogen may be a full-length molecule or a portion thereof. If the polypeptide portion is "hapten-like", such portion may be advantageously joined or linked to a macromolecular carrier (such as keyhole limpet hemocyanin (KLH), bovine serum albumin (BSA) or tetanus toxoid) for immunization.

As used herein, the term "antibodies" includes polyclonal antibodies, affinity-purified polyclonal antibodies, monoclonal antibodies, and antigen-binding fragments, such as $F(ab')_2$ and Fab proteolytic fragments. Genetically engineered intact antibodies or fragments, such as chimeric antibodies, Fv fragments, single chain antibodies and the like, as well as synthetic antigen-binding peptides and polypeptides, are also included. Non-human antibodies may be humanized by grafting non-human CDRs onto human framework and constant regions, or by incorporating the entire non-human variable domains (optionally "cloaking" them with a human-like surface by replacement of exposed residues, wherein the result is a "veneered" antibody). In some instances, humanized antibodies may retain non-human residues within the human variable region framework domains to enhance proper binding characteristics. Through humanizing antibodies, biological half-life may be increased, and the potential for adverse immune reactions upon administration to humans is reduced.

Antibodies are considered to be specifically binding if: 1) they exhibit a threshold level of binding activity, and 2) they do not significantly cross-react with related polypeptide molecules. A threshold level of binding is determined if anti-soluble zcytor11 receptor or anti-soluble zcytor11 heterodimeric polypeptide, such as anti-soluble zcytor11/CRF2-4 antibodies herein bind to a soluble zcytor11 receptor or soluble zcytor11 heterodimeric polypeptide, such as soluble zcytor11/CRF2-4 polypeptide, peptide or epitope with an affinity at least 10-fold greater than the binding affinity to control (non-soluble zcytor11 receptor or soluble zcytor11 heterodimeric polypeptide, such as soluble zcytor11/CRF2-4) polypeptide. It is preferred that the antibodies exhibit a binding affinity ($K_a$) of $10^6$ $M^{-1}$ or greater, preferably $10^7$ $M^{-1}$ or greater, more preferably $10^8$ $M^{-1}$ or greater, and most preferably $10^9$ $M^{-1}$ or greater. The binding affinity of an antibody can be readily determined by one of ordinary skill in the art, for example, by Scatchard analysis (Scatchard, G., *Ann. NY Acad. Sci.* 51: 660–672, 1949).

Whether anti-soluble zcytor11 receptor or anti-soluble zcytor11 heterodimeric polypeptide, such as anti-soluble zcytor11/CRF2-4 antibodies do not significantly cross-react with related polypeptide molecules is shown, for example, by the antibody detecting soluble zcytor11 receptor or soluble zcytor11 heterodimeric polypeptide, such as soluble zcytor11/CRF2-4 polypeptide but not known related polypeptides using a standard Western blot analysis (Ausubel et al., ibid.). Examples of known related polypeptides are those disclosed in the prior art, such as known orthologs, and paralogs, and similar known members of a protein family. Screening can also be done using non-human soluble zcytor11 receptor or soluble zcytor11 heterodimeric polypeptide, such as soluble zcytor11/CRF2-4, and soluble zcytor11 receptor or soluble zcytor11 heterodimeric polypeptide, such as soluble zcytor11/CRF2-4 mutant polypeptides. Moreover, antibodies can be "screened against" known related polypeptides, to isolate a population that specifically binds to the soluble zcytor11 receptor or soluble zcytor11 heterodimeric polypeptide, such as soluble zcytor11/CRF2-4 polypeptides. For example, antibodies raised to soluble zcytor11 receptor or soluble zcytor11 heterodimeric polypeptide, such as soluble zcytor11/CRF2-4 are adsorbed to related polypeptides adhered to insoluble matrix; antibodies specific to soluble zcytor11 receptor or soluble zcytor11 heterodimeric polypeptide, such as soluble zcytor11/CRF2-4 will flow through the matrix under the proper buffer conditions. Screening allows isolation of polyclonal and monoclonal antibodies non-crossreactive to known closely related polypeptides (*Antibodies: A Laboratory Manual*, Harlow and Lane (eds.), Cold Spring Harbor Laboratory Press, 1988; *Current Protocols in Immunology*, Cooligan, et al. (eds.), National Institutes of Health, John Wiley and Sons, Inc., 1995). Screening and isolation of specific antibodies is well known in the art. See, *Fundamental Immunology*, Paul (eds.), Raven Press, 1993; Getzoff et al., *Adv. in Immunol.* 43: 1–98, 1988; *Monoclonal Antibodies: Principles and Practice*, Goding, J. W. (eds.), Academic Press Ltd., 1996; Benjamin et al., *Ann. Rev. Immunol.* 2: 67–101, 1984. Specifically binding anti-soluble zcytor11 receptor or anti-soluble zcytor11 heterodimeric polypeptide, such as anti-soluble zcytor11/CRF2-4 antibodies can be detected by a number of methods in the art, and disclosed below.

A variety of assays known to those skilled in the art can be utilized to detect antibodies that bind to soluble zcytor11 receptor or soluble zcytor11 heterodimeric polypeptide, such as soluble zcytor11/CRF2-4 proteins or polypeptides. Exemplary assays are described in detail in *Antibodies: A Laboratory Manual*, Harlow and Lane (Eds.), Cold Spring Harbor Laboratory Press, 1988. Representative examples of such assays include: concurrent immunoelectrophoresis, radioimmunoassay, radioimmuno-precipitation, enzyme-linked immunosorbent assay (ELISA), dot blot or Western blot assay, inhibition or competition assay, and sandwich assay. In addition, antibodies can be screened for binding to wild-type versus mutant soluble zcytor11 receptor or soluble zcytor11 heterodimeric polypeptide, such as soluble zcytor11/CRF2-4 protein or polypeptide.

Alternative techniques for generating or selecting antibodies useful herein include in vitro exposure of lymphocytes to soluble zcytor11 receptor or soluble zcytor11 heterodimeric polypeptide, such as soluble zcytor11/CRF2-4 protein or peptide, and selection of antibody display libraries in phage or similar vectors (for instance, through use of immobilized or labeled soluble zcytor11 receptor or soluble zcytor11 heterodimeric polypeptide, such as soluble zcytor11/CRF2-4 protein or peptide). Genes encoding polypeptides having potential binding domains for soluble zcytor11 receptor or soluble zcytor11 heterodimeric polypeptide, such as soluble zcytor11/CRF2-4 polypeptide, can be obtained by screening random peptide libraries displayed on phage (phage display) or on bacteria, such as *E. coli*. Nucleotide sequences encoding the polypeptides can be obtained in a number of ways, such as through random mutagenesis and random polynucleotide synthesis. These random peptide display libraries can be used to screen for peptides which interact with a known target which can be a protein or polypeptide, such as a ligand or receptor, a biological or synthetic macromolecule, or organic or inorganic substances. Techniques for creating and screening such random peptide display libraries are known in the art (Ladner et al., U.S. Pat. No. 5,223,409; Ladner et al., U.S. Pat. No. 4,946,778; Ladner et al., U.S. Pat. No. 5,403,484 and Ladner et al., U.S. Pat. No. 5,571,698) and random peptide display libraries and kits for screening such libraries are available commercially, for instance from Clontech (Palo Alto, Calif.), Invitrogen Inc. (San Diego, Calif.), New England Biolabs, Inc. (Beverly, Mass.) and Pharmacia LKB Biotechnology Inc. (Piscataway, N.J.). Random peptide display libraries can be screened using the soluble zcytor11 receptor or soluble zcytor11 heterodimeric polypeptide, such as soluble zcytor11/CRF2-4 sequences disclosed herein to identify proteins which bind to soluble zcytor11 receptor or soluble zcytor11 heterodimeric polypeptide, such as soluble zcytor11/CRF2-4. These "binding polypeptides" which interact with soluble zcytor11 receptor or soluble zcytor11 heterodimeric polypeptide, such as soluble zcytor11/CRF2-4 polypeptides can be used for tagging cells; for isolating homolog polypeptides by affinity purification; they can be directly or indirectly conjugated to drugs, toxins, radionuclides and the like. These binding polypeptides can also be used in analytical methods such as for screening expression libraries and neutralizing activity, e.g., for blocking interaction between IL-TIF ligand and receptor, or viral binding to a receptor. The binding polypeptides can also be used for diagnostic assays for determining circulating levels of soluble zcytor11 receptor or soluble zcytor11 heterodimeric polypeptide, such as soluble zcytor11/CRF2-4 polypeptides; for detecting or quantitating soluble zcytor11 receptor or soluble zcytor11 heterodimeric polypeptide, such as soluble zcytor11/CRF2-4 polypeptides as marker of underlying pathology or disease. These binding polypeptides can also act as zcytor11 receptor or zcytor11 heterodimeric polypeptide, such as zcytor11/CRF2-4 "antagonists" to block zcytor11 receptor or zcytor11 heterodimeric polypeptide, such as zcytor11/CRF2-4 binding and signal transduction in vitro and in vivo. Again, these anti-soluble zcytor11 receptor or anti-soluble zcytor11 heterodimeric polypeptide, such as anti-soluble zcytor11/CRF2-4 binding polypeptides would be useful for inhibiting IL-TIF activity, as well as receptor activity or protein-binding. Antibodies raised to the heterodimer or multimeric combinations of the present invention are preferred embodiments, as they may act more specifically against the IL-TIF, or more potently than antibodies raised to only one subunit. Moreover, the antagonistic and binding activity of the antibodies of the present invention can be assayed in the IL-TIF proliferation and other biological assays described herein.

Antibodies to soluble zcytor11 receptor or soluble zcytor11 heterodimeric polypeptide, such as soluble zcytor11/CRF2-4 may be used for tagging cells that express zcytor11 receptor or zcytor11 heterodimeric polypeptides, such as zcytor11/CRF2-4; for isolating soluble zcytor11 receptor or soluble zcytor11 heterodimeric polypeptide, such as soluble zcytor11/CRF2-4 polypeptide by affinity purification; for diagnostic assays for determining circulating levels of soluble zcytor11 receptor or soluble zcytor11 heterodimeric polypeptide, such as soluble zcytor11/CRF2-4 polypeptides; for detecting or quantitating soluble zcytor11 receptor or soluble zcytor11 heterodimeric polypeptide, such as soluble zcytor11/CRF2-4 as marker of underlying pathology or disease; in analytical methods employing FACS; for screening expression libraries; for generating anti-idiotypic antibodies; and as neutralizing antibodies or as antagonists to block zcytor11 receptor or zcytor11 heterodimeric polypeptide, such as zcytor11/CRF2-4, or IL-TIF activity in vitro and in vivo. Suitable direct tags or labels include radionuclides, enzymes, substrates, cofactors, inhibitors, fluorescent markers, chemiluminescent markers, magnetic particles and the like; indirect tags or labels may feature use of biotin-avidin or other complement/anti-complement pairs as intermediates. Antibodies herein may also be directly or indirectly conjugated to drugs, toxins, radionuclides and the like, and these conjugates used for in vivo diagnostic or therapeutic applications. Moreover, antibodies to soluble zcytor11 receptor or soluble zcytor11 heterodimeric polypeptide, such as soluble zcytor11/CRF2-4 or fragments thereof may be used in vitro to detect denatured or non-denatured soluble zcytor11 receptor or soluble zcytor11 heterodimeric polypeptide, such as soluble zcytor11/CRF2-4 or fragments thereof in assays, for example, Western Blots or other assays known in the art.

Antibodies to soluble zcytor11 receptor or soluble zcytor11 heterodimeric polypeptide, such as soluble zcytor11/CRF2-4 are useful for tagging cells that express the corresponding receptors and assaying their expression levels, for affinity purification, within diagnostic assays for determining circulating levels of soluble receptor polypeptides, analytical methods employing fluorescence-activated cell sorting. Moreover, divalent antibodies, and anti-idiotypic antibodies may be used as agonists to mimic the effect of the IL-TIF.

Antibodies herein can also be directly or indirectly conjugated to drugs, toxins, radionuclides and the like, and these conjugates used for in vivo diagnostic or therapeutic applications. For instance, antibodies or binding polypeptides which recognize soluble zcytor11 receptor or soluble zcytor11 heterodimeric polypeptide, such as soluble zcytor11/CRF2-4 polypeptides of the present invention can be used to identify or treat tissues or organs that express a corresponding anti-complementary molecule (i.e., a zcytor11 receptor, or zcytor11 heterodimeric receptor, such as zcytor11/CRF2-4). More specifically, anti- soluble zcytor11 receptor or anti-soluble zcytor11 heterodimeric polypeptide, such as anti-soluble zcytor11/CRF2-4 antibodies, or bioactive fragments or portions thereof, can be coupled to detectable or cytotoxic molecules and delivered to a mammal having cells, tissues or organs that express the zcytor11 receptor or a zcytor11 heterodimeric receptor, such as zcytor11/CRF2-4 receptor molecules.

Suitable detectable molecules may be directly or indirectly attached to polypeptides that bind soluble zcytor11 receptor or soluble zcytor11 heterodimeric polypeptide, such as soluble zcytor11/CRF2-4 ("binding polypeptides," including binding peptides disclosed above), antibodies, or bioactive fragments or portions thereof. Suitable detectable molecules include radionuclides, enzymes, substrates, cofactors, inhibitors, fluorescent markers, chemiluminescent markers, magnetic particles and the like. Suitable cytotoxic molecules may be directly or indirectly attached to the polypeptide or antibody, and include bacterial or plant toxins (for instance, diphtheria toxin, *Pseudomonas* exotoxin, ricin, abrin and the like), as well as therapeutic radionuclides, such as iodine-131, rhenium-188 or yttrium-90 (either directly attached to the polypeptide or antibody, or indirectly attached through means of a chelating moiety, for instance). Binding polypeptides or antibodies may also be conjugated to cytotoxic drugs, such as adriamycin. For indirect attachment of a detectable or cytotoxic molecule, the detectable or cytotoxic molecule can be conjugated with a member of a complementary/anticomplementary pair, where the other member is bound to the binding polypeptide or antibody portion. For these purposes, biotin/streptavidin is an exemplary complementary/anticomplementary pair.

In another embodiment, binding polypeptide-toxin fusion proteins or antibody-toxin fusion proteins can be used for targeted cell or tissue inhibition or ablation (for instance, to treat cancer cells or tissues). Alternatively, if the binding polypeptide has multiple functional domains (i.e., an activation domain or a ligand binding domain, plus a targeting domain), a fusion protein including only the targeting domain may be suitable for directing a detectable molecule, a cytotoxic molecule or a complementary molecule to a cell or tissue type of interest. In instances where the fusion protein including only a single domain includes a complementary molecule, the anti-complementary molecule can be conjugated to a detectable or cytotoxic molecule. Such domain-complementary molecule fusion proteins thus represent a generic targeting vehicle for cell/tissue-specific delivery of generic anti-complementary-detectable/cytotoxic molecule conjugates.

In another embodiment, soluble zcytor11 receptor or soluble zcytor11 heterodimeric polypeptide, such as soluble zcytor11/CRF2-4 binding polypeptide-cytokine or antibody-cytokine fusion proteins can be used for enhancing in vivo killing of target tissues (for example, pancreatic, blood, lymphoid, colon, and bone marrow cancers), if the binding polypeptide-cytokine or anti-soluble zcytor11 receptor or anti-soluble zcytor11 heterodimeric polypeptide, such as anti-soluble zcytor11/CRF2-4 antibody targets the hyperproliferative cell (See, generally, Hornick et al., *Blood* 89:4437–47, 1997). The described fusion proteins enable targeting of a cytokine to a desired site of action, thereby providing an elevated local concentration of cytokine. Suitable anti-zcytor11 homodimer and heterodimer antibodies target an undesirable cell or tissue (i.e., a tumor or a leukemia), and the fused cytokine mediates improved target cell lysis by effector cells. Suitable cytokines for this purpose include interleukin 2 and granulocyte-macrophage colony-stimulating factor (GM-CSF), for instance.

Alternatively, soluble zcytor11 receptor or soluble zcytor11 heterodimeric polypeptide, such as soluble zcytor11/CRF2-4 binding polypeptide or antibody fusion proteins described herein can be used for enhancing in vivo killing of target tissues by directly stimulating a zcytor11 receptor-modulated apoptotic pathway, resulting in cell death of hyperproliferative cells expressing zcytor11 receptor or a zcytor11 heterodimeric receptor, such as soluble zcytor11/CRF2-4 receptor.

The invention is further illustrated by the following non-limiting examples.

EXAMPLE 1

Construction of Mammalian Expression Vectors That Express zcytor11 Soluble

Receptors: zcytor11CEE, zcytor11CFLG, zcytor11CHIS and zcytor11-Fc4

A. Construction of zcytor11 Mammalian Expression Vector Containing zcytor11CEE, zcytor11CFLG and zcytor11CHIS An expression vector is prepared for the expression of the soluble, extracellular domain of the zcytor11 polypeptide (SEQ ID NO:3), pC4zcytor11CEE, wherein the construct is designed to express a zcytor11 polypeptide comprised of the predicted initiating methionine and truncated adjacent to the predicted transmembrane domain, and with a C-terminal Glu-Glu tag (SEQ ID NO:4).

A zcytor11 DNA fragment comprising the zcytor11 extracellular cytokine binding domain (SEQ ID NO:3) is created using PCR, and purified. The excised DNA is subcloned into a plasmid expression vector that has a signal peptide, e.g., the native zcytor11 signal peptide, and attaches a Glu-Glu tag (SEQ ID NO:4) to the C-terminus of the zcytor11 polypeptide-encoding polynucleotide sequence. Such an expression vector mammalian expression vector contains an expression cassette having a mammalian promoter, multiple restriction sites for insertion of coding sequences, a stop codon and a mammalian terminator. The plasmid can also have an *E. coli* origin of replication, a mammalian selectable marker expression unit having an SV40 promoter, enhancer and origin of replication, a DHFR gene and the SV40 terminator.

Restriction digested zcytor11 insert and previously digested vector are ligated using standard molecular biological techniques, and electroporated into competent cells such as DH10B competent cells (GIBCO BRL, Gaithersburg, Md.) according to manufacturer's direction and plated onto LB plates containing 50 mg/ml ampicillin, and incubated overnight. Colonies are screened by restriction analysis of DNA prepared from individual colonies. The insert sequence of positive clones is verified by sequence analysis. A large scale plasmid preparation is done using a QIAGEN® Maxi prep kit (Qiagen) according to manufacturer's instructions.

The same process is used to prepare the zcytor11 soluble homodimeric, heterodimeric or multimeric receptors (including non-zcytor 1 soluble receptor subunits, such as, soluble CRF2-4 or IL-10R) with a C-terminal his tag, composed of 6 His residues in a row; and a C-terminal flag (SEQ ID NO:5) tag, zcytor11CFLAG. To construct these constructs, the aforementioned vector has either the HIS or the FLAG® tag in place of the glu-glu tag (SEQ ID NO:4).

B. Mammalian Expression Construction of Soluble zcytor11 Receptor zcytor11-Fc4

An expression plasmid containing all or part of a polynucleotide encoding zcytor11 is constructed via homologous recombination. A fragment of zcytor11 cDNA was isolated using PCR that includes the polynucleotide sequence from extracellular domain of the zcytor11 receptor. Primers used in PCR for the production of the zcytor11 fragment are from 5' to 3' end: (1) about 40 bp of the vector flanking sequence (5' of the insert) and about17 bp corresponding to the 5' end of the zcytor11 extracellular domain; and (2) about 40 bp of the 5' end of the Fc4 polynucleotide sequence (SEQ ID NO:6) and about 17 bp corresponding to the 3' end of the zcytor11 extracellular domain. The fragment of Fc4 for fusion with the zcytor11 is generated by PCR in a similar fashion. The two primers used in the production of the Fc4 fragment include: (1) a 5' primer consisting of about 40 bp of sequence from the 3' end of zcytor11 extracellular domain and about 17 bp of the 5' end of Fc4 (SEQ ID NO:6); and (2) a 3' primer consisting of about 40 bp of vector sequence (3' of the insert) and about 17 bp of the 3' end of Fc4 (SEQ ID NO:6). PCR amplification of the each of the reactions described above is then performed using conditions standard in the art.

An exemplary expression vector is derived from the plasmid pCZR199 (deposited at the American Type Culture Collection, 10801 University Boulevard, Manassas, Va. 20110-2209, designated No. 98668), that is cut with SmaI (BRL). The expression vector was derived from the plasmid pCZR199, and is a mammalian expression vector containing an expression cassette having the CMV immediate early promoter, a consensus intron from the variable region of mouse immunoglobulin heavy chain locus, multiple restriction sites for insertion of coding sequences, a stop codon and a human growth hormone terminator. The expression vector also has an *E. coli* origin of replication, a mammalian selectable marker expression unit having an SV40 promoter, enhancer and origin of replication, a DHFR gene and the SV40 terminator. The expression vector used was constructed from pCZR199 by the replacement of the metallothionein promoter with the CMV immediate early promoter.

Competent yeast cells (*S. cerevisiae*) are combined with approximately 1 μg each of the zcytor11 and Fc4 inserts, and 100 ng of SmaI (BRL) digested expression vector and electroporated. The yeast/DNA mixtures are electropulsed at, for example, 0.75 kV (5 kV/cm), "infinite" ohms, 25 μF. To each cuvette is added 600 μl of 1.2 M sorbitol and the yeast was plated in aliquots onto URA-D plates and incubated at 30° C.

After about 48 hours, the Ura+ yeast transformants from a single plate are picked, DNA isolated, and transformed into electrocompetent *E. coli* cells (e.g., DH10B, Gibco-BRL), and plated using standard procedures. Individual clones harboring the correct expression construct for zcytor11-Fc4 are identified by restriction digest to verify the presence of the zcytor11-Fc4 insert and to confirm that the various DNA sequences have been joined correctly to one another. The insert of positive clones is subjected to sequence analysis. Larger scale plasmid DNA is isolated using the Qiagen Maxi kit (Qiagen) according to manufacturer's instructions.

Similar methods are used to prepare non-zcytor11 subunits of heterodimeric and multimeric receptors, such as CRF2-4 and IL-10R tagged with Fc4.

EXAMPLE 2

Transfection and Expression of Soluble Receptor Polypeptides

BHK 570 cells (ATCC No. CRL-10314), DG-44 CHO, or other mammalian cells are plated at about $1.2\times10^6$ cells/well (6-well plate) in 800 μl of appropriate serum free (SF) media (e.g., DMEM, Gibco/BRL High Glucose) (Gibco BRL, Gaithersburg, Md.). The cells are transfected with expression plasmids containing zcytor11CEE, zcytor11CFLG, zcytor11CHIS or zcytor11-Fc4 (Example 1), or non-zcytor11 subunits of heterodimeric and multimeric receptors, such as -CEE, -CFLG, -CHIS, or -Fc4 tagged CRF2-4 and IL-10R, using Lipofectin™ (Gibco BRL), in serum free (SF) media according to manufacturer's instruction. Single clones expressing the soluble receptors are isolated, screened and grown up in cell culture media, and purified using standard techniques.

EXAMPLE 3

Expression of zcytor11 Soluble Receptor in *E. coli*

A. Construction of Expression Vector pCZR225 that Expresses huzcytor11/MBP-6H Fusion Polypeptide An expression plasmid containing a polynucleotide encoding a zcytor11 soluble receptor fused C-terminally to maltose binding protein (MBP) is constructed via homologous recombination. The fusion polypeptide contains an N-terminal approximately 388 amino acid MBP portion fused to the zcytor11 soluble receptor (SEQ ID NO:3). A fragment of zcytor11 cDNA (SEQ ID NO:1) is isolated using PCR as described herein. Two primers are used in the production of the zcytor11 fragment in a standard PCR reaction: (1) one containing about 40 bp of the vector flanking sequence and about 25 bp corresponding to the amino terminus of the zcytor11, and (2) another containing about 40 bp of the 3' end corresponding to the flanking vector sequence and about 25 bp corresponding to the carboxyl terminus of the zcytor11. Two μl of the 100 μl PCR reaction is run on a 1.0% agarose gel with 1×TBE buffer for analysis, and the expected approximately fragment is seen. The remaining PCR reaction is combined with the second PCR tube and precipitated with 400 μl of absolute ethanol. The precipitated DNA used for recombining into the Sma1 cut recipient vector pTAP98 to produce the construct encoding the MBP-zcytor11 fusion, as described below.

Plasmid pTAP98 is derived from the plasmids pRS316 and pMAL-c2. The plasmid pRS316 is a *Saccharomyces cerevisiae* shuttle vector (Hieter P. and Sikorski, R., *Genetics* 122:19–27, 1989). pMAL-C2 (NEB) is an *E. coli* expression plasmid. It carries the tac promoter driving MalE (gene encoding MBP) followed by a His tag, a thrombin cleavage site, a cloning site, and the rrnB terminator. The vector pTAP98 is constructed using yeast homologous recombination. 100 ng of EcoR1 cut pMAL-c2 is recombined with 1 μg Pvu1 cut pRS316, 1 μg linker, and 1 μg Sca1/EcoR1 cut pRS316 are combined in a PCR reaction. PCR products are concentrated via 100% ethanol precipitation.

Competent yeast cells (*S. cerevisiae*) are combined with about 10 μl of a mixture containing approximately 1 μg of the zcytor11 receptor PCR product above, and 100 ng of SmaI digested pTAP98 vector, and electroporated using standard methods and plated onto URA-D plates and incubated at 30° C.

After about 48 hours, the Ura+ yeast transformants from a single plate are picked, DNA isolated, and transformed into electrocompetent *E. coli* cells (e.g., MC1061, Casadaban et. al. *J. Mol. Biol.* 138, 179–207), and plated on MM/CA +AMP 100 mg/L plates (Pryor and Leiting, *Protein Expression and Pruification* 10:309–319, 1997).using standard procedures. Cells are grown in MM/CA with 100 μg/ml Ampicillin for two hours, shaking, at 37° C. 1 ml of the culture is induced with 1 mM IPTG. 2–4 hours later the 250 μl of each culture is mixed with 250 μl acid washed glass beads and 250 μl Thomer buffer with 5% βME and dye (8M urea, 100 mM Tris pH7.0, 10% glycerol, 2 mM EDTA, 5% SDS). Samples are vortexed for one minute and heated to 65° C. for 10 minutes. 20 μl are loaded per lane on a 4%–12% PAGE gel (NOVEX). Gels are run in 1×MES buffer. The positive clones are designated pCZR225 and subjected to sequence analysis.

One microliter of sequencing DNA is used to transform strain BL21. The cells are electropulsed at 2.0 kV, 25 μF and 400 ohms. Following electroporation, 0.6 ml MM/CA with 100 mg/L Ampicillin. Cells are grown in MM/CA and induced with ITPG as described above., The positive clones are used to grow up for protein purification of the huzcytor11/MBP-6H fusion protein using standard techniques.

EXAMPLE 4

Zcytor11 Soluble Receptor Polyclonal Antibodies

Polyclonal antibodies are prepared by immunizing female New Zealand white rabbits with the purified huzcytor11/MBP-6H polypeptide (Example 3), or the purified recombinant zcytor11CEE soluble receptor (Example 1). The rabbits are each given an initial intraperitoneal (IP) injection of 200 mg of purified protein in Complete Freund's Adjuvant (Pierce, Rockford, Ill.) followed by booster IP injections of 100 mg purified protein in Incomplete Freund's Adjuvant every three weeks. Seven to ten days after the administration of the third booster injection, the animals are bled and the serum is collected. The rabbits are then boosted and bled every three weeks.

The zcytor11-specific polyclonal antibodies are affinity purified from the rabbit serum using an CNBr-SEPHAROSE 4B protein column (Pharmacia LKB) that is prepared using about 10 mg of the purified huzcytor11/MBP-6H polypeptide per gram CNBr-SEPHAROSE, followed by 20× dialysis in PBS overnight. Zcytor11-specific antibodies are characterized by an ELISA titer check using 1 mg/ml of the appropriate protein antigen as an antibody target. The lower limit of detection (LLD) of the rabbit anti-zcytor11 affinity purified antibodies is determined using standard methods.

EXAMPLE 5

Zcytor11 Receptor Monoclonal Antibodies

Zcytor11 soluble receptor Monoclonal antibodies are prepared by immunizing male BalbC mice (Harlan Sprague Dawley, Indianapolis, Ind.) with the purified recombinant soluble zcytor11 proteins described herein. The mice are each given an initial intraperitoneal (IP) injection of 20 mg of purified protein in Complete Freund's Adjuvant (Pierce, Rockford, Ill.) followed by booster IP injections of 10 mg purified protein in Incomplete Freund's Adjuvant every two weeks. Seven to ten days after the administration of the third booster injection, the animals are bled and the serum is collected, and antibody titer assessed.

Splenocytes are harvested from high-titer mice and fused to murine SP2/0 myeloma cells using PEG 1500 (Boerhinger Mannheim, UK) in two separate fusion procedures using a 4:1 fusion ratio of splenocytes to myeloma cells (*Antibodies: A Laboratory Manual*, E. Harlow and D. Lane, Cold Spring Harbor Press). Following 10 days growth post-fusion, specific antibody-producing hybridomas are identified by ELISA using purified recombinant zcytor11 soluble receptor protein (Example 6C) as an antibody target and by FACS using Baf3 cells expressing the zcytor11 sequence (Example 8) as an antibody target. The resulting hybridomas positive by both methods are cloned three times by limiting dilution.

EXAMPLE 6

Assessing Zcytor11 Receptor Heterodimerization Using ORIGEN Assay

Soluble zcytor11 receptor zcytor11CFLAG (Example 1), or gp130 (Hibi, M. et al., *Cell* 63:1149–1157, 1990) are biotinylated by reaction with a five-fold molar excess of sulfo-NHS-LC-Biotin (Pierce, Inc., Rockford, Ill.) according to the manufacturer's protocol. Soluble zcytor11 receptor and another soluble receptor subunit, for example, soluble IL-10R (sIL-10R) or CRF2-4 receptor (CRF2-4) (R&D Systems, Minneapolis, Minn.), or soluble zcytor11 receptor (U.S. Pat. No. 5,965,704) are labeled with a five fold molar excess of Ru-BPY-NHS (Igen, Inc., Gaithersburg, Md.) according to manufacturer's protocol. The biotinylated and Ru-BPY-NHS-labeled forms of the soluble zcytor11 receptor can be respectively designated Bio-zcytor11 receptor and Ru-zcytor11; the biotinylated and Ru-BPY-NHS-labeled forms of the other soluble receptor subunit can be similarly designated. Assays can be carried out using conditioned media from cells expressing a ligand, such as IL-TIF, that binds zcytor11 heterodimeric receptors, or using purified IL-TIF.

For initial receptor binding characterization a panel of cytokines or conditioned medium are tested to determine whether they can mediate homodimerization of zcytor11 receptor and if they can mediate the heterodimerization of zcytor11 receptor with the soluble receptor subunits described above. To do this, 50 □l of conditioned media or TBS-B containing purified cytokine, is combined with 50 □l of TBS-B (20 mM Tris, 150 mM NaCl, 1 mg/ml BSA, pH 7.2) containing e.g., 400 ng/ml of Ru-zcytor11 receptor and Bio-zcytor11, or 400 ng/ml of Ru-zcytor11 receptor and e.g., Bio-gp130, or 400 ng/ml of e.g., Ru-CRF2-4 and Bio-zcytor11. Following incubation for one hour at room temperature, 30 µg of streptavidin coated, 2.8 mm magnetic beads (Dynal, Inc., Oslo, Norway) are added and the reaction incubated an additional hour at room temperature. 200 µl ORIGEN assay buffer (Igen, Inc., Gaithersburg, Md.) is then added and the extent of receptor association measured using an M8 ORIGEN analyzer (Igen, Inc.).

EXAMPLE 7

Construct for Generating a zcytor11 Receptor Heterodimer

A vector expressing a secreted human zcytor11 heterodimer was constructed. In this construct, the extracellular cytokine-binding domain of zcytor11 was fused to the heavy chain of IgG gamma 1 (IgGγ1) with a Glu-Glu tag (SEQ ID NO:4) at the C-terminus, while the extracellular portion of the heteromeric cytokine receptor subunit (e.g., an CRF2-4, IL-9, IL-10 IL-4 receptor component) was fused to the heavy chain of IgG gamma 1 (IgGγ1) with a His tag at the C-terminus.

A. Construction of IgG Gamma 16-His and IgG Gamma 1 Glu-Glu Fusion Vectors

The heavy chain of IgGγ1 with a 6-His c-terminal tag (SEQ ID NO:13) was cloned into the pZP-9 mammalian expression vector (ATCC Deposit No. 98668) such that any desired cytokine receptor extracellular domain having a 5' EcoRI and 3' BamHI site can be cloned in, resulting in an N-terminal extracellular domain-C-terminal IgGγ1 fusion. The IgGγ1 fragment used in this construct was made by using PCR to isolate the IgGγ1 uaing oligonucleotide primers ZC29,239 (SEQ ID NO:14) and ZC29,232 (SEQ ID NO:15). PCR products were purified using methods described herein and digested with XhoI and BamHI (Boerhinger-Mannheim) and subsequently gel purified. The extracellular portion of CRF2-4 (SEQ ID NO:18) was amplified using PCR, using oligonucleotide primers ZC39,319 (SEQ ID NO:16) and ZC39,325 (SEQ ID NO:17). PCR products were purified using methods described herein and digested with EcoRI and BamHI (Boerhinger-Mannheim) and subsequently gel purified. The BamHI/XhoI IgGγ1 fragment and EcoRI/BamHI CRF2-4 fragment derived above were then ligated together into pZP-9 previously digested with EcoRI and XhoI to derive a construct that had the extracellular portion of CRF2-4 extracellular cytokine binding domain fused to IgGγ1 with a 6-HIS tag at the c-terminus. This construct was subsequently modified to introduce a thrombin cleavage site 3' of CRF2-4 and 5' of the 6-HIS tag. This was done by using the above construct as template in PCR with oligonucleotide primers ZC38,981 (SEQ ID NO:20) and ZC39,042 (SEQ ID NO:21). PCR products were purfied using methods described herein and digested with SacII and XhoI. This SacII/XhoI fragment was ligated into the construction described above that had been previously digested with SacII and XhoI. The polynucleotide sequence of the CRF2-4 extracellular cytokine binding domain fused to IgGγ1 with a 6-HIS tag is shown in SEQ ID NO:22 and the corresponding polypeptide sequence is shown in SEQ ID NO:23.

The heavy chain of IgGγ1 with a Glu-Glu c-terminal tag (SEQ ID NO:4) was cloned into the Zem228R mammalian expression vector (ATCC deposit No. 69446) such that any desired cytokine receptor extracellular domain having a 5' EcoRI site and a 3' BamHI site can be cloned in resulting in a N-terminal cytokine extracellular domain-C-terminal IgGγ1 fusion. The IgGγ1 fragment used in this construct was made by using PCR to isolate the IgGγ1 sequence using oligonucleotide primers ZC29238 (SEQ ID NO:24) and ZC29231 (SEQ ID NO:25). PCR products were purified using methods described herein and digested with XhoI and EcoRI (Boerhinger-Mannheim) and subsequently gel purified. The extracellular portion of hzcytor11 (SEQ ID NO:1) was amplified using PCR using oligonucleotides ZC39335 (SEQ ID NO:26) and ZC28981 (SEQ ID NO:27). PCR products were purified using methods described herein and digested with EcoRI and BamHI (Boerhinger-Mannheim) and subsequently gel purified. The BamHI/XhoI IgGγ1 fragment and EcoRI/BamHI hzcytor11 fragments derived above were then ligated together into Zem228R previously digested with EcoRI and XhoI to derive a construct that had the extracellular domain of hzcytor11 fused to IgGγ1 with a Glu-Glu epitope tag at the C-terminus. This construct was subsequently modified to introduce a thrombin cleavage site 3' of CRF2-4 and 5' of the 6-HIS tag. This was done by using the above construct as template in PCR with oligonucleotide primers ZC38981 (SEQ ID NO:27) and ZC39043 (SEQ ID NO:28). PCR products were purfied using methods described herein and digested with SacIII and XhoI. This SacII/XhoI fragment was ligated into the construction described above that had been previously digested with SacII and XhoI. The polynucleotide sequence of the hzcytor11 extracellular cytokine binding domain fused to IgGγ1 with a Glu-Glu tag is shown in SEQ ID NO:29 and the corresponding polypeptide sequence is shown in SEQ ID NO:30.

B. Co-expression of the zcytor11 and Heterodimeric Cytokine Receptor Subunit Extracellular Domain 16 μg of each of vectors above, were co-transfected into mammalian cells, e.g., BHK-570 cells (ATCC No. CRL-10314) using LipofectaminePlus™ reagent (Gibco/BRL), as per manufacturer's instructions. The transfected cells were selected for 10 days in DMEM+5% FBS (Gibco/BRL) containing 1 μM of methotrexate (MTX) (Sigma, St. Louis, Mo.) and 0.5 mg/ml G418 (Gibco/BRL) for 10 days. The resulting pool of transfectants was selected again in 10 μm of MTX and 0.5 mg/ml G418 for 10 days.

The resulting pool of doubly selected cells was used to generate zcytor11/CRF2-4 soluble receptor protein. Three Factories (Nunc, Denmark) of this pool were used to generate 10 L of serum free conditioned medium. This conditioned media was passed over a nickel column followed by a Glu-Glu column to purify heterodimers away from homodimers.

EXAMPLE 8

Determination of Receptor Subunits that Heterodimerize or Multimerize with zcytor11 Receptor Using standard methods described herein, The BaF3/MPL-zcytor11 chimera cells are transfected with an additional heterodimeric cytokine receptor subunit serve as a bioassay cell line to measure signal transduction response of heterodimeric zcytor11 receptor complexes to the luciferase reporter in the presence of TPO. In the presence of TPO, the BaF3/MPL-zcytor11 cells do not signal, suggesting that zcytor11 receptor must heterodimerize to signal. Transfection of the BaF3/MPL-zcytor11 cell line with and additional MPL-class I cytokine receptor fusion that signals in the presence of the TPO ligand, determines which heterodimeric cytokine receptor subunits are required for zcytor11 receptor signaling. Use of MPL-receptor fusions for this purpose alleviates the requirement for the presence of a natural ligand for the zcytor11 receptor.

MPL-class I cytokine receptor fusions are made as per Example 5 using the extracellular domain and transmembrane domains of the MPL receptor and the intracellular signaling domain of the desired class I cytokine receptor. The BaF3/MPL-zcytor11 bioassay cell line co-transfected with an individual MPL-class I cytokine receptor fusions as per Example 6 to form a BaF3/MPL-zcytor11/MPL-class I cytokine receptor cell line. Receptor complexes include but are not limited to zcytor11 receptor in combination with an MPL-cytokine receptor fusion comprising one or more of e.g., a CRF2-4, IL-9, IL-10 IL-4 receptor component. Each independent receptor complex cell line is then assayed in the presence of TPO and proliferation measured using routine methods (e.g., Alamar Blue assay). The BaF3/MPL-zcytor11 bioassay cell line serves as a control for the background luciferase activity, and is thus used as a baseline to compare signaling by the various receptor complex combinations. In addition, a BaF3/MPL-class I cytokine receptor cell line can be constructed to control for MPL-class I cytokine receptor homodimerization effects for those class I cytokine receptors known to signal upon homodimerization. The TPO in the presence of the correct receptor complex, is expected to increase proliferation of the BaF3/MPL-zcytor 11/MPL-class I cytokine receptor cell line approximately 5 fold over background or greater in the presence of TPO.

Similar proliferation assays use full-length zcytor11 (SEQ ID NO:2) to screen for additional non-zcytor11 subunits that signal heterodimeric and multimeric complexes. Cells expressing full-length zcytor11 (SEQ ID NO:2) are transfected with a non-zcytor11 subunit and assayed for proliferation in the presence of IL-TIF ligand. Cells expressing the components of zcytor11 heterodimeric and multimeric receptors should proliferate in the presence of IL-TIF.

EXAMPLE 9

Reconstitution of zcytor11 Receptor in vitro

To identify components involved in the zcytor11-signaling complex, receptor reconstitution studies are performed as follows. BHK 570 cells (ATCC No. CRL-10314) transfected, using standard methods described herein, with a luciferase reporter mammalian expression vector plasmid serve as a bioassay cell line to measure signal transduction response from a transfected zcytor11 receptor complex to the luciferase reporter in the presence of IL-TIF. BHK cells do not endogenously express the zcytor11 receptor. An exemplary luciferase reporter mammalian expression vector is the KZ134 plasmid which was constructed with complementary oligonucleotides that contain STAT transcription factor binding elements from 4 genes. A modified c-fos Sis inducible element (m67SIE, or hSIE) (Sadowski, H. et al., *Science* 261:1739–1744, 1993), the p21 SIE1 from the p21 WAF1 gene (Chin, Y. et al., *Science* 272:719–722, 1996), the mammary gland response element of the β-casein gene (Schmitt-Ney, M. et al., *Mol. Cell. Biol.* 11:3745–3755, 1991), and a STAT inducible element of the Fcg RI gene, (Seidel, H. et al., *Proc. Natl. Acad. Sci.* 92:3041–3045, 1995). These oligonucleotides contain Asp718-XhoI compatible ends and were ligated, using standard methods, into a recipient firefly luciferase reporter vector with a c-fos promoter (Poulsen, L. K. et al., *J. Biol. Chem.* 273:6229–6232, 1998) digested with the same enzymes and containing a neomycin selectable marker. The KZ134 plasmid is used to stably transfect BHK, or BaF3 cells, using standard transfection and selection methods, to make a BHK/KZ134 or BaF3/KZ134 cell line respectively.

The bioassay cell line is transfected with zcytor11 receptor alone, or co-transfected with zcytor11 receptor along with one of a variety of other known receptor subunits. Receptor complexes include but are not limited to zcytor11 receptor only, various combinations of zcytor11 receptor with one or more of the CRF2-4, IL-9, IL-10 IL-4 receptor components, class II cytokine receptor subunits, or the IL-2 receptor components (IL-2Rα, IL-2Rβ, IL-2Rγ), zcytor11 receptor with one or more of the IL-4/IL-13 receptor family receptor components (IL-4Rα, IL-13Rα, IL-13Rα'), as well as other Interleukin receptors (e.g., IL-15 Rα, IL-7Rα, IL-9Rα, IL-21R (zcytor11)). Each independent receptor complex cell line is then assayed in the presence of cytokine-conditioned media or purified cytokines and luciferase activity measured using routine methods. The untransfected bioassay cell line serves as a control for the background luciferase activity, and is thus used as a baseline to compare signaling by the various receptor complex combinations. The conditioned medium or cytokine that binds the zyctorlo receptor in the presence of the correct receptor complex, is expected to give a luciferase readout of approximately 5 fold over background or greater.

As an alternative, a similar assay can be performed wherein the Baf3/zcytor11-mpl and Baf3/zcytor11 cell lines are co-transfected as described above and proliferation measured.

EXAMPLE 10

Construct for Generating CEE-tagged IL-TIF

Oligonucleotides were designed to generate a PCR fragment containing the Kozak sequence and the coding region for IL-TIF, without its stop codon. These oligonucleotides were designed with a KpnI site at the 5' end and a BamHI site at the 3' end to facilitate cloning into pHZ200-CEE, our standard vector for mammalian expression of C-terminal Glu-Glu tagged (SEQ ID NO:4) proteins. The pHZ200 vector contains an MT-1 promoter.

PCR reactions were carried out using Turbo Pfu polymerase (Stratagene) to amplify a IL-TIF cDNA fragment. About 20 ng human IL-TIF polynucleotide template (SEQ ID NO:7), and oligonucleotides ZC28590 (SEQ ID NO:9) and ZC28580 (SEQ ID NO:10) were used in the PCR reaction. PCR reaction conditions were as follows: 95° C. for 5 minutes; 30 cycles of 95° C. for 60 seconds, 55° C. for 60 seconds, and 72° C. for 60 seconds; and 72° C. for 10 minutes; followed by a 4° C. hold. PCR products were separated by agarose gel electrophoresis and purified using a QiaQuick™ (Qiagen) gel extraction kit. The isolated, approximately 600 bp, DNA fragment was digested with KpnI and BamHI (Boerhinger-Mannheim), gel purified as above and ligated into pHZ200-CEE that was previously digested with KpnI and BamHI.

About one microliter of the ligation reaction was electroporated into DH10B ElectroMax™ competent cells (GIBCO BRL, Gaithersburg, Md.) according to manufacturer's direction and plated onto LB plates containing 100 μg/ml ampicillin, and incubated overnight. Colonies were picked and screened by PCR using oligonucleotides ZC28590 (SEQ ID NO:9) and ZC28580 (SEQ ID NO:10), with PCR conditions as described above. Clones containing inserts were then sequenced to confirm error-free IL-TIF inserts. Maxipreps of the correct pHZ200-IL-TIF-CEE construct, as verified by sequence analysis, were performed.

EXAMPLE 11

Transfection and Expression of IL-TIF Polypeptides

BHK 570 cells (ATCC No. CRL-10314), were plated at about $1.2\times10^6$ cells/well (6-well plate) in 800 μl of serum free (SF) DMEM media (DMEM, Gibco/BRL High Glucose) (Gibco BRL, Gaithersburg, Md.). The cells were transfected with an expression plasmid containing IL-TIF-CEE described above (Example 10), using Lipofectin™ (Gibco BRL), in serum free (SF) DMEM according to manufacturer's instructions.

The cells were incubated at 37° C. for approximately five hours, then transferred to separate 150 mm MAXI plates in a final volume of 30 ml DMEM/5% fetal bovine serum (FBS) (Hyclone, Logan, Utah). The plates were incubated at 37° C., 5% $CO_2$, overnight and the DNA: Lipofectin™ mixture was replaced with selection media (5% FBS/DMEM with 1 μM methotrexate (MTX)) the next day.

Approximately 10–12 days post-transfection, colonies were mechanically picked to 12-well plates in one ml of 5% FCS/DMEM with 5 μM MTX, then grown to confluence. Positive expressing clonal colonies Conditioned media samples were then tested for expression levels via SDS-PAGE and Western analysis. A high-expressing clone was picked and expanded for ample generation of conditioned media for purification of the IL-TIF-CEE expressed by the cells (Example 12).

EXAMPLE 12

Purification of IL-TIF-CEE Polypeptide from BHK 570 Cells

Unless otherwise noted, all operations were carried out at 4° C. The following procedure was used for purifying IL-TIF polypeptide containing C-terminal GluGlu (EE) tags (SEQ ID NO:4). Conditioned media from BHK cells expressing IL-TIF-CEE (Example 11) was concentrated with an Amicon S10Y3 spiral cartridge on a ProFlux A30. A Protease inhibitor solution was added to the concentrated conditioned media to final concentrations of 2.5 mM ethylenediaminetetraacetic acid (EDTA, Sigma Chemical Co. St. Louis, Mo.), 0.003 mM leupeptin (Boehringer-Mannheim, Indianapolis, Ind.), 0.001 mM pepstatin (Boehringer-Mannheim) and 0.4 mM Pefabloc (Boehringer-Mannheim). Samples were removed for analysis and the bulk volume was frozen at −80° C. until the purification was started. Total target protein concentrations of the concentrated conditioned media were determined via SDS-PAGE and Western blot analysis with the anti-EE HRP conjugated antibody.

About 100 ml column of anti-EE G-Sepharose (prepared as described below) was poured in a Waters AP-5, 5 cm×10 cm glass column. The column was flow packed and equilibrated on a BioCad Sprint (PerSeptive BioSystems, Framingham, Mass.) with phosphate buffered saline (PBS) pH 7.4. The concentrated conditioned media was thawed, 0.2 micron sterile filtered, pH adjusted to 7.4, then loaded on the column overnight with about 1 ml/minute flow rate. The column was washed with 10 column volumes (CVs) of phosphate buffered saline (PBS, pH 7.4), then plug eluted with 200 ml of PBS (pH 6.0) containing 0.5 mg/ml EE peptide (Anaspec, San Jose, Calif.) at 5 ml/minute. The EE peptide used has the sequence EYMPME (SEQ ID NO:4). The column was washed for 10 CVs with PBS, then eluted with 5 CVs of 0.2M glycine, pH 3.0. The pH of the glycine-eluted column was adjusted to 7.0 with 2 CVs of 5×PBS, then equilibrated in PBS (pH 7.4). Five ml fractions were collected over the entire elution chromatography and absorbance at 280 and 215 nM were monitored; the pass through and wash pools were also saved and analyzed. The EE-polypeptide elution peak fractions were analyzed for the target protein via SDS-PAGE Silver staining and Western Blotting with the anti-EE HRP conjugated antibody. The polypeptide elution fractions of interest were pooled and concentrated from 60 ml to 5.0 ml using a 10,000 Dalton molecular weight cutoff membrane spin concentrator (Millipore, Bedford, Mass.) according to the manufacturer's instructions.

To separate IL-TIF-CEE from other co-purifying proteins, the concentrated polypeptide elution pooled fractions were subjected to a POROS HQ-50 (strong anion exchange resin from PerSeptive BioSystems, Framingham, Mass.) at pH 8.0. A 1.0×6.0 cm column was poured and flow packed on a BioCad Sprint. The column was counter ion charged then equibrated in 20 mM TRIS pH 8.0 (Tris (Hydroxymethyl Aminomethane)). The sample was diluted 1:13 (to reduce the ionic strength of PBS) then loaded on the Poros HQ column at 5 ml/minute. The column was washed for 10 CVs with 20 mM Tris pH 8.0 then eluted with a 40 CV gradient of 20 mM Tris/1 M sodium chloride (NaCl) at 10 ml/minute. 1.5 ml fractions were collected over the entire chromatography and absorbance at 280 and 215 nM were monitored. The elution peak fractions were analyzed via SDS-PAGE Silver staining. Fractions of interest were pooled and concentrated to 1.5–2 ml using a 10,000 Dalton molecular weight cutoff membrane spin concentrator (Millipore, Bedford, Mass.) according to the manufacturer's instructions.

To separate IL-TIF-CEE polypeptide from free EE peptide and any contaminating co-purifying proteins, the pooled concentrated fractions were subjected to size exclusion chromatography on a 1.5×90 cm Sephadex S200 (Pharmacia, Piscataway, N.J.) column equilibrated and loaded in PBS at a flow rate of 1.0 ml/min using a BioCad Sprint. 1.5 ml fractions were collected across the entire chromatography and the absorbance at 280 and 215 nM were monitored. The peak fractions were characterized via SDS-PAGE Silver staining, and only the most pure fractions were pooled. This material represented purified IL-TIF-CEE polypeptide.

This purified material was finally subjected to a 4 ml ActiClean Etox (Sterogene) column to remove any remaining endotoxins. The sample was passed over the PBS equilibrated gravity column four times then the column was washed with a single 3 ml volume of PBS, which was pooled with the "cleaned" sample. The material was then 0.2 micron sterile filtered and stored at −80° C. until it was aliquoted.

On Western blotted, Coomassie Blue and Silver stained SDS-PAGE gels, the IL-TIF-CEE polypeptide was one major band. The protein concentration of the purified material was performed by BCA analysis (Pierce, Rockford, Ill.) and the protein was aliquoted, and stored at −80° C. according to standard procedures.

To prepare anti-EE Sepharose, a 100 ml bed volume of protein G-Sepharose (Pharmacia, Piscataway, N.J.) was washed 3 times with 100 ml of PBS containing 0.02% sodium azide using a 500 ml Nalgene 0.45 micron filter unit. The gel was washed with 6.0 volumes of 200 mM triethanolamine, pH 8.2 (TEA, Sigma, St. Louis, Mo.), and an equal volume of EE antibody solution containing 900 mg of antibody was added. After an overnight incubation at 4° C., unbound antibody was removed by washing the resin with 5 volumes of 200 mM TEA as described above. The resin was resuspended in 2 volumes of TEA, transferred to a suitable container, and dimethylpimilimidate-2HCl (Pierce, Rockford, Ill.) dissolved in TEA, was added to a final concentration of 36 mg/ml of protein G-Sepharose gel. The gel was rocked at room temperature for 45 min and the liquid was removed using the filter unit as described above. Nonspecific sites on the gel were then blocked by incubating for 10 min. at room temperature with 5 volumes of 20 mM ethanolamine in 200 mM TEA. The gel was then washed with 5 volumes of PBS containing 0.02% sodium azide and stored in this solution at 4° C.

EXAMPLE 13

In vivo Affects of L-TIF Polypeptide

Mice (female, C57B1, 8 weeks old; Charles River Labs, Kingston, N.Y.) were divided into three groups. An adenovirus expressing an IL-TIF polypeptide (SEQ ID NO:8) was previously made using standard methods. On day 0, parental or IL-TIF adenovirus was administered to the first (n=8) and second (n=8) groups, respectively, via the tail vein, with each mouse receiving a dose of ~$1\times10^{11}$ particles in ~0.1 ml volume. The third group (n=8) received no treatment. On days 12, mice were weighed and blood was drawn from the mice. Samples were analyzed for complete blood count (CBC) and serum chemistry. Statistically significant elevations in neutrophil and platelet counts were detected in the blood samples from the IL-TIF adenovirus administered group relative to the parental adenovirus treated group. Also, lymphocyte and red blood cell counts were significantly reduced from the IL-TIF adenovirus administered group relative to the parental adenovirus treated group. In addition, the IL-TIF adenovirus treated mice decreased in body weight, while parental adenovirus treated mice gained weight. The SAA and globulin level was increased and glucose level was decreased. The adeno-zcyto18 mice displayed wasting syndrome. In summary, zcyto18 causes acute phase response (APR) that reflects the pro-inflammatory activity of TNF-α, IL-1, and gp130 cytokines.

The result suggested that IL-TIF is a pro-inflammatory factor that is involved in the immune and inflammatory response in vivo. The tissue distribution of IL-TIF receptor (zcytor11) indicated that elevated expression of IL-TIF in circulation or specific tissues can lead to certain acute/chronic inflammatory diseases, such as pancreatitis, IBD (Chron's disease, colitis), asthma, ESRD (end stage renal diseases), rheumatoid arthritis, psoriasis, and autoimmune diseases (GVHD, lupus, sepsis).

The results suggested that IL-TIF affects hematopoiesis, i.e., blood cell formation in vivo. As such, IL-TIF could have biological activities effecting different blood stem cells, thus resulting increase or decrease of certain differentiated blood cells in a specific lineage. For instance, IL-TIF appears to reduce lymphocytes, which is likely due to inhibition of the committed progenitor cells that give rise to lymphoid cells. IL-TIF also decreases red blood cells. This finding agrees with the inhibitory effects of IL-TIF on the proliferation and/or growth of myeloid stem cells (Example 13), supporting the notion that IL-TIF could play a role in anemia, infection, inflammation, and/or immune diseases by influencing blood cells involved in these process. Antagonists against IL-TIF, such as antibodies or zcytor11 soluble receptors of the present invention, could be used as therapeutic reagents in these diseases.

Moreover, these experiments using IL-TIF adenovirus in mice suggest that IL-TIF over-expression increases the level of neutrophils and platelets in vivo. It is conceivable that there are other factors (such as cytokines and modifier genes) involved in the responses to IL-TIF in the whole animal system. Nevertheless, these data strongly support the involvement of IL-TIF in hematopoiesis. Thus, IL-TIF and its receptors are suitable reagents/targets for the diagnosis and treatment in variety of disorders, such as inflammation, immune disorders, infection, anemia, hematopoietic and other cancers, and the like.

EXAMPLE 14

Identification of Cells Expressing zcytor11 Using in situ Hybridization

Specific human tissues were isolated and screened for zcytor11 expression by in situ hybridization. Various human tissues prepared, sectioned and subjected to in situ hybridization included appendix, brain, cartilage, colon, intestine, kidney, liver, lung, lymph node, lymphoma, ovary, pancreas, placenta, prostate, skin, spleen, and thymus. The tissues were fixed in 10% buffered formalin and blocked in paraffin using standard techniques. Tissues were sectioned at 4 to 8 microns. Tissues were prepared using a standard protocol ("Development of non-isotopic in situ hybridization" at The Laboratory of Experimental Pathology (LEP), NIEHS, Research Triangle Park, N.C.; web address http://dir.niehs.nih.gov/dirlep/ish.html). Briefly, tissue sections were deparaffinized with HistoClear (National Diagnostics, Atlanta, Ga.) and then dehydrated with ethanol. Next they were digested with Proteinase K (50 μg/ml) (Boehringer Diagnostics, Indianapolis, Ind.) at 37° C. for 2 to 7 minutes. This step was followed by acetylation and re-hydration of the tissues.

One in situ probe was designed against the human zcytor11 sequence (nucleotide 234–1105 in SEQ ID NO:1), and isolated from a plasmid containing SEQ ID NO:11 using standard methods. T7 RNA polymerase was used to generate an antisense probe. The probe was labeled with digoxigenin (Boehringer) using an In Vitro transcription System (Promega, Madison, Wis.) as per manufacturer's instruction.

In situ hybridization was performed with a digoxigenin-labeled zcytor11 probe (above). The probe was added to the slides at a concentration of 1 to 5 pmol/ml for 12 to 16 hours at 60° C. Slides were subsequently washed in 2×SSC and 0.1×SSC at 55° C. The signals were amplified using tyramide signal amplification (TSA) (TSA, in situ indirect kit; NEN) and visualized with Vector Red substrate kit (Vector Lab) as per manufacturer's instructions. The slides were then counter-stained with hematoxylin (Vector Laboratories, Burlingame, Calif.).

Signals were observed in several tissues tested: The lymph node that contains cells in the paracortex of nodules was strongly positive. In lymphoma samples, there is little to no signal in the samples tested. In spleen, positive signals were seen in scattered mononuclear cells at the periphery of follicles were positive. In thymus, positive signals were seen in scattered mononuclear cells in both cortex and medulla was positive. In fetal liver, a strong signal was observed in a mixed population of mononuclear cells in sinusoid spaces. Some circulating mononuclear cells were also positive. Hepatocytes were negative. In the inflamed appendix, mononuclear cells in Peyer's patch and infiltration sites were positive. In intestine, cells in laminar propria and Peyer's patches were strongly positive. Ganglia nerve cells in the muscles were positive. In normal lung, zcytor11 was expressed in alveolar epithelium and mononuclear cells in interstitial tissue and circulation. In the lung carcinoma tissue, a weak signal was observed in carcinoma cells and mononuclear cells in peripheral of carcinoma sites. In ovary carcinoma, epithelium cells were strongly positive. Some interstitial cells, most likely the mononuclear cells, were also positive. There was no signal observed in the normal ovary. In kidney, podocytes and simple epithelial cells in the parietal layer of Bowman's capsules in renal corpuscles were positive. Cuboidal epithelial cells of distal convoluted tubules were also positive. In both normal and pancreatitis pancreas samples, acinar cells and some mononuclear cells in the mesentery were positive. There may be also weak signal in a subset of cells in islets of pancreas. In the early term (8 weeks) placenta, signal was observed in trophoblasts. In skin, strong signal was observed in the keratinocytes and mononuclear cells in the inflamed infiltrates in the superficial dermis. In brain, majority of neurons in temporal lobe were positive, however, the frontal lobe appears to be negative. In articular cartilage, chondrocytes were positive. Other tissues tested including normal ovary, skin melanoma, prostate carcinoma and BPH were negative.

In summary, the in situ data was consistent with expression data described above for the zcytor11. Zcytor11 expression was observed predominately and consistently expressed by a mixed population of mononuclear cells. A subset of epithelium was also positive. These results confirmed the presence of zcytor11 expression in immune cells and point toward a role in inflammation, autoimmune disease, or other immune function, for example, in binding pro-inflammatory cytokines, including but not limited to IL-TIF. Moreover, detection of zcytor11 expression can be used for example as a marker for mononuclear cells in histologic samples.

Zcytor11 is expressed in mononuclear cells, including normal tissues (lymph nodes, spleen, thymus, pancreas, kidney, liver and lung), and abnormal tissues (inflamed appendix, lung carcinoma, ovary carcinoma, pancreatitis, inflamed skin, and prostate carcinoma). It is notable that plasma cells in the lymph node, intestine, and lung carcinoma are positive for zcytor11. Plasma cells are immunologically activated lymphocytes responsible for antibody synthesis. In addition, IL-TIF is expressed in activated T cells, and the expression of zcytor11 is detected only in resting (but not in activated) CD19+ cells (Example 13). Thus, zcytor11 can be used as a marker for or as a target in isolating certain lymphocytes, such as mononuclear leucocytes and limited type of activated leucocytes, such as resting CD19+.

Furthermore, the presence of zcytor11 expression in immune cells such as CD8+ T cell and CD19+ B cells showed that zcytor11 may be involved in the body's immune defensive reactions against foreign invaders: such as microorganisms and cell debris, and could play a role in immune responses during inflammation and cancer formation. The activation of zcytor11 receptor may cause autoimmune and inflammatory diseases such as GVHD, sepsis and lupus.

Moreover, as discussed herein, epithelium form several tissues was positive for zcytor11 expression, such as skin, kidney, gut, hepatocytes (endoderm-derived epithelia), lung alveolar epithelium (endoderm-derived epithelia), and ovary carcinoma epithelium (mesoderm-derived epithelium). The inflammatory response in these tissues may cause acute/chronic inflammatory diseases, such as psoriasis (skin), end-stage renal disease ESRD (kidney), IBD (Chron's disease, colitis) (gut), and asthma/respiratory allergy/chronic bronchitis (lung). The epithelium expression of zcytor11 could be altered in inflammatory responses and/or cancerous states in liver and lung. Thus, ligand for zcytor11, such as IL-TIF, or a receptor-binding fragment thereof, could be used as marker to monitor changes in these tissues as a result of inflammation or cancer. Moreover, analysis of zcytor11 in situ expression showed that normal ovary epithelium is negative for zcytor11 expression, while it is strongly positive in ovary carcinoma epithelium providing further evidence that IL-TIF polypeptides, or a receptor-binding fragment thereof, can be used as a diagnostic marker and/or therapeutic target for the diagnosis and treatment of ovarian cancers, and ovary carcinoma, as described herein.

Zcytor11 was also detected in other tissues, such as acinar cells in pancreas (normal and pancreatitis tissues), trophoblasts in placenta (ectoderm-derived), chondrocytes in cartilage (mesoderm-derived), and ganglia cells in intestine (ectoderm-derived). As such, zcytor11 may be involved in differentiation and/or normal functions of corresponding cells in these organs. As such, potential utilities of zcytor11 include maintenance of normal metabolism and pregnancy, bone formation/homeostasis, and physiological function of intestine, and the like. Moreover, the up-regulation of IL-TIF may potentially cause the inflammatory response in those tissues that lead to certain inflammatory diseases such as pancreatitis, rheumatoid arthritis, IBD (colitis and Chron's disease).

EXAMPLE 15

Human zcytor11 Tissue Distribution in Tissue Panels Using Northern Blot and PCR

A. Human zcytor11 Tissue Distribution in Tissue Panels Using PCR

A panel of cDNAs from human tissues was screened for zcytor11 expression using PCR. The panel was made in-house and contained 94 marathon cDNA and cDNA samples from various normal and cancerous human tissues and cell lines are shown in Table 4 below. Aside from the PCR reaction, the method used was as shown in Example 12. The PCR reactions were set up using oligos ZC14,666 (SEQ ID NO: 11) and ZC14,742 (SEQ ID NO:12), Advantage 2 cDNA polymerase mix (Clontech, Palo Alto, Calif.), and Rediload dye (Research Genetics, Inc., Huntsville, Ala.). The amplification was carried out as follows: 1 cycle at 94° C. for 2 minutes, 40 cycles of 94° C. for 15 seconds, 51° C. for 30 seconds and 72° C. for 30 seconds, followed by 1 cycle at 72° C. for 7 minutes. The correct predicted DNA fragment size was observed in bladder, brain, cervix, colon, fetal brain, fetal heart, fetal kidney, fetal liver, fetal lung, fetal skin, heart, kidney, liver, lung, melanoma, ovary, pancreas, placenta, prostate, rectum, salivary gland, small intestine, testis, thymus, trachea, spinal cord, thyroid, lung tumor, ovarian tumor, rectal tumor, and stomach tumor. Zcytor11 expression was not observed in the other tissues and cell lines tested in this panel.

A commercial 1st strand cDNA panel (Human Blood Fractions MTC Panel, Clontech, Palo Alto, Calif.) was also assayed as above. The panel contained the following samples: mononuclear cells, activated mononuclear cells, resting CD4+ cells, activated CD4+ cells, resting CD8+ cells, activated CD8+ cells, resting CD14+ cells, resting CD19+ cells and activated CD19+ cells. All samples except activated CD8+ and Activated CD19+ showed expression of zcytor11.

TABLE 4

| Tissue | # samples | Tissue | # samples |
|---|---|---|---|
| adrenal gland | 1 | bladder | 1 |
| bone marrow | 3 | brain | 2 |
| cervix | 1 | colon | 1 |
| fetal brain | 3 | fetal heart | 2 |
| fetal kidney | 1 | fetal liver | 2 |
| fetal lung | 1 | fetal skin | 1 |
| heart | 2 | fetal muscle | 1 |
| kidney | 2 | liver | 1 |
| lung | 1 | lymph node | 1 |
| mammary gland | 1 | melanoma | 1 |
| ovary | 1 | pancreas | 1 |
| pituitary | 2 | placenta | 3 |
| prostate | 3 | rectum | 1 |
| salivary gland | 2 | skeletal muscle | 1 |
| small intestine | 1 | spinal cord | 2 |
| spleen | 1 | uterus | 1 |
| stomach | 1 | adipocyte library | 1 |
| testis | 5 | islet | 1 |
| thymus | 1 | prostate SMC | 1 |
| thyroid | 2 | RPMI 1788 | 1 |
| trachea | 1 | WI38 | 1 |
| esophageal tumor | 1 | lung tumor | 1 |
| liver tumor | 1 | ovarian tumor | 1 |
| rectal tumor | 1 | stomach tumor | 1 |
| uterine tumor | 2 | CD3+ library | 1 |
| HaCAT library | 1 | HPV library | 1 |
| HPVS library | 1 | MG63 library | 1 |
| K562 | 1 | | |

B. Tissue Distribution of Zcytor11 in Human Cell Line and Tissue Panels Using RT-PCR A panel of RNAs from human cell lines was screened for zcytor11 expression using RT-PCR. The panels were made in house and contained 84 RNAs from various normal and cancerous human tissues and cell lines as shown in Tables 5–8 below. The RNAs were made from in house or purchased tissues and cell lines using the RNAeasy Midi or Mini Kit (Qiagen, Valencia, Calif.). The panel was set up in a 96-well format with 100 ngs of RNA per sample. The RT-PCR reactions were set up using oligos ZC14,666 (SEQ ID NO:11) and ZC14,742 (SEQ ID NO:12), Rediload dye and SUPERSCRIPT One Step RT-PCR System (Life Technologies, Gaithersburg, Md.). The amplification was carried out as follows: one cycle at 50° for 30 minutes followed by 45 cycles of 94°, 15 seconds; 52°, 30 seconds; 72°, 30 seconds; then ended with a final extension at 72° for 7 minutes. 8 to 10 uls of the PCR reaction product was subjected to standard Agarose gel electrophoresis using a 4% agarose gel. The correct predicted cDNA fragment size was observed in adrenal gland, bladder, breast, bronchus, normal colon, colon cancer, duodenum, endometrium, esophagus, gastic cancer, gastro-esophageal cancer, heart ventricle, iluem, normal kidney, kidney cancer, liver, lung, lymph node, pancreas, parotid, skin, small bowel, stomach, thyroid, and uterus. Cell lines showing expression of zcytor11 were A-431, differentiated CaCO2, DLD-1, HBL-100, HCT-15, HepG2, HepG2+IL6, HuH7, and NHEK #1-4. Zcytor11 expression was not observed in the other tissues and cell lines tested in this panel. The expression pattern of zcytor11 shows expression in specific tissues and tissue-specific tumors. One of skill in the art would recognize that the polynucleotides, polypeptides, antibodies, and binding partners of the present invention can be used as a diagnostic to detect cancer, or cancer tissue in a biopsy, tissue, or histologic sample, particularly in tissues where zcytor11 is expressed. Such diagnostic uses for the molecules of the present invention are known in the art and described herein.

In addition, because the expression pattern of zcytor11, one of IL-TIF's receptors, shows expression in certain specific tissues, binding partners including the natural ligand, IL-TIF, can also be used as a diagnostic to detect specific tissues (normal or abnormal), cancer, or cancer tissue in a biopsy, tissue, or histologic sample, particularly in tissues where IL-TIF receptors are expressed. IL-TIF can also be used to target other tissues wherein its receptors, e.g., zcytor11 and CRF2-4, are expressed. Moreover, such binding partners could be conjugated to chemotherapeutic agents, toxic moieties and the like to target therapy to the site of a tumor or diseased tissue. Such diagnostic and targeted therapy uses are known in the art and described herein.

The expression patterns of zcytor11 (above) indicated target tissues and cell types for the action of IL-TIF, and hence IL-TIF antagonists, such as the soluble zcytor11 receptors of the present invention. The zcytor11 is generally expressed in three physiologic systems: digestive system, female reproductive system, and immune system. Moreover, the expression pattern of the receptor (zcytor11) indicated that an IL-TIF antagonist the soluble zcytor11 receptors of the present invention would have therapeutic application for human disease in two areas: inflammation (e.g., IBD, Chron's disease, pancreatitis) and cancer (e.g., ovary, colon). That is, the polynucleotides, polypeptides and antibodies of the present invention can be used to antagonize the inflammatory, and other cytokine-induced effects of IL-TIF interaction with the cells expressing the zcytor11 receptor.

Moreover, the expression of zcytor11 appeared to be downregulated or absent in an ulcerative colitis tissue, HepG2 liver cell line induced by IL-6, activated CD8+ T-cells and CD19+ B-cells. These RT-PCR experiments demonstrate that CD19+ peripheral blood cells, B lymphocytes, express receptors for IL-TIF, namely zcytoR11. The soluble zcytor11 receptors of the present invention would act as an antagonist to neutralize the effects of IL-TIF on B cells. This would be beneficial in diseases where B cells are the key players: Autoimmune diseases including systemic lupus erythmatosus (SLE), myasthenia gravis, immune complex disease, and B-cell cancers that are exacerbated by IL-TIF. Also autoimmune diseases where B cells contribute to the disease pathology would be targets for zcytor11 soluble receptor therapy: Multiple sclerosis, inflammatory bowel disease (IBD) and rheumatoid arthritis are examples. Soluble zcytor11 receptor therapy would be beneficial to dampen or inhibit B cells producing IgE in atopic diseases including asthma, allergy and atopic dermatitis where the production of IgE contributes to the pathogenesis of disease.

B cell malignancies may exhibit a loss of regulation by cytokines, such as IL-TIF. The administration of the soluble zcytor11 receptors of the present invention following surgical resection or chemotherapy may be useful to treat minimal residual disease in patients with B cell malignancies. The loss of regulation may lead to sustain or increased expression of zcytor11. Thus creating a target for therapeutic monoclonal antibodies targeting zcytor11 comprising receptors, such as those described herein.

TABLE 5

| Tissue | # samples | Tissue | # samples |
|---|---|---|---|
| adrenal gland | 6 | duodenum | 1 |
| bladder | 3 | endometrium | 5 |

TABLE 5-continued

| Tissue | # samples | Tissue | # samples |
|---|---|---|---|
| brain | 2 | cancerous endometrium | 1 |
| brain meningioma | 1 | gastric cancer | 1 |
| breast | 1 | esophagus | 7 |
| cancerous breast | 4 | gastro-esophageal | 1 |
| normal breast adjacent to cancer | 5 | heart aorta | 1 |
| bronchus | 3 | heart left ventricle | 4 |
| colon | 15 | heart right ventricle | 2 |
| cancerous colon | 1 | heart ventricle | 1 |
| normal colon adjacent to cancer | 1 | ileum | 3 |
| ulcerative colitis colon | 1 | kidney | 15 |
| | | cancerous kidney | 1 |

TABLE 6

| Tissue/Cell Line | #samples | Tissue/Cell Line | #samples |
|---|---|---|---|
| 293 | 1 | HBL-100 | 1 |
| C32 | 1 | Hs-294T | 1 |
| HaCat#1 | 1 | Molt4 | 1 |
| HaCat#2 | 1 | RPMI | 1 |
| HaCat#3 | 1 | U-937 | 1 |
| HaCat#4 | 1 | A-375 | 1 |
| WI-38 | 1 | HCT-15 | 1 |
| WI-38 + 2 um ionomycin #1 | 1 | HT-29 | 1 |
| WI-38 + 2 um ionomycin #2 | 1 | MRC-5 | 1 |
| WI-38 + 5 um ionomycin #1 | 1 | RPT-1 | 1 |
| WI-38 + 5 um ionomycin #2 | 1 | RPT-2 | 1 |
| Caco-2, | 1 | WM-115 | 1 |
| Caco-2, differentiated | 1 | A-431 | 1 |
| DLD-1 | 1 | WERI-Rb-1 | 1 |
| HRE | 1 | HEL-92.1.7 | 1 |
| HRCE | 1 | HuH-7 | 1 |
| MCF7 | 1 | MV-4-11 | 1 |
| PC-3 | 1 | U-138 | 1 |
| TF-1 | 1 | CCRF-CEM | 1 |
| 5637 | 1 | Y-79 | 1 |
| 143B | 1 | A-549 | 1 |
| ME-180 | 1 | EL-4 | 1 |
| prostate epithelia | 1 | HeLa 229 | 1 |
| U-2 OS | 1 | HUT 78 | 1 |
| T-47D | 1 | NCI-H69 | 1 |
| Mg-63 | 1 | SaOS2 | 1 |
| Raji | 1 | USMC | 1 |
| U-373 MG | 1 | UASMC | 2 |
| A-172 | 1 | AoSMC | 1 |
| CRL-1964 | 1 | UtSMC | 1 |
| CRL-1964 + butryic acid | 1 | HepG2 | 1 |
| HUVEC | 1 | HepG2-IL6 | 1 |
| SK-Hep-1 | 1 | NHEK#1 | 1 |
| SK-Lu-1 | 1 | NHEK#2 | 1 |
| Sk-MEL-2 | 1 | NHEK#3 | 1 |
| K562 | 1 | NHEK#4 | 1 |
| BeWo | 1 | ARPE-19 | 1 |
| FHS74.Int | 1 | G-361 | 1 |
| HL-60 | 1 | HISM | 1 |
| Malme 3M | 1 | 3AsubE | 1 |
| FHC | 1 | INT407 | 1 |
| HREC | 1 | | |

TABLE 7

| Tissue | # samples | Tissue | # samples |
|---|---|---|---|
| liver | 10 | lung | 13 |
| lymph node | 1 | cancerous lung | 2 |

TABLE 7-continued

| Tissue | # samples | Tissue | # samples |
|---|---|---|---|
| lymphoma | 4 | normal lung adjacent to cancer | 1 |
| mammary adenoma | 1 | muscle | 3 |
| mammary gland | 3 | neuroblastoma | 1 |
| melinorioma | 1 | omentum | 2 |
| osteogenic sarcoma | 2 | ovary | 6 |
| pancreas | 4 | cancerous ovary | 2 |
| skin | 5 | parotid | 7 |
| sarcoma | 2 | salivary gland | 4 |

TABLE 8

| Tissue | # samples | Tissue | # samples |
|---|---|---|---|
| small bowel | 10 | uterus | 11 |
| spleen | 3 | uterine cancer | 1 |
| spleen lymphoma | 1 | thyroid | 9 |
| stomach | 13 | | |
| stomach cancer | 1 | | |

C. Tissue Distribution of Zcytor11 in Human Origene™ Tissue and Human Blood Fractions MTC Panels Using RT-PCR A panel of RNAs from human tissues, Human Origene™ Tissue and Human Blood Fractions MTC Panels (Origene Technologies, Rockville, Md.; and Clontech, Palo Alto, Calif.) was screened for zcytor11 expression using RT-PCR. The panels contained 24 RNAs from various normal human tissues at increasing concentrations as shown in Tables 9–10 below. The RT-PCR reactions were set up using oligos ZC37693 (SEQ ID NO:31) and ZC37449 (SEQ ID NO:32), using the Advantage PCR kit (Clontech). The amplification was carried out as follows: one cycle at 94° C. for 2 min.; 35 cycles of 94° C. for 15 sec., 72° C. for 1.5 min; then 72° C. for 2 min.; followed by a 4° C. hold. 8 to 10 μl of the PCR reaction product was subjected to standard Agarose gel electrophoresis using a 4% agarose gel.

Using the Origene Panel, as shown in Table 9, the correct predicted cDNA fragment size (440 bp) was observed in all tissues except spleen, muscle, placenta, PBL, bone marrow and fetal brain. However, there was high expression specifically in small intestine, colon, kidney, skin, lung, pancreas and liver. The weak expression of zcytor11 was also observed in ovary, uterus, prostate, brain, heart, testis, stomach, and thyroid. Zcytor11 expression was not observed in the other tissues and cell lines tested in this panel. The expression pattern of zcytor11 shows expression in specific tissues. One of skill in the art would recognize that the polynucleotides, polypeptides, antibodies, and binding partners of the present invention can be used as a diagnostic to detect such tissues, cancer, or cancer tissue in a biopsy, tissue, or histologic sample, particularly in tissues where zcytor11 is expressed. Such diagnostic uses for the molecules of the present invention are known in the art and described herein.

Using the Human Blood Fractions MTC Panel, as shown in Table 10, the correct predicted cDNA fragment size (440 bp) was observed in mononuclear cells, resting CD8+ cells, resting CD19+ cells and placenta. Zcytor11 expression was not observed in the other tissues and cell lines tested in this panel, including activated CD8+ and CD19+ cells. The expression pattern of zcytor11 shows expression in specific tissues. One of skill in the art would recognize that the polynucleotides, polypeptides, antibodies, and binding partners of the present invention can be used as a diagnostic to detect such tissues, cancer, or cancer tissue in a biopsy, tissue, or histologic sample, particularly in tissues where zcytor11 is expressed. Such diagnostic uses for the molecules of the present invention are known in the art and described herein.

TABLE 9

| Tissue | 1 pg cDNA | 10 pg cDNA | 100 pg cDNA | 1 ng cDNA |
|---|---|---|---|---|
| Brain | | | | X |
| Heart | | | | X |
| Kidney | | | X | X |
| Spleen | | | | |
| Liver | | | X | X |
| Colon | | | X | X |
| Lung | | | X | X |
| Small Intestine | | X | X | X |
| Muscle | | | | |
| Stomach | | | X | X |
| Testis | X | | X | X |
| Placenta | | | X | |
| Salivary Gland | | | | X |
| Thyroid Gland | | | X | X |
| Adrenal Gland | | | X | X |
| Pancreas | X | X | X | X |
| Ovary | | | | X |
| Uterus | | | | X |
| Prostate | | | | X |
| Skin | | | X | X |
| PBL | | | | |
| Bone Marrow | | | | |
| Fetal Brain | | | | |
| Fetal Liver | | X | X | X |

TABLE 10

| 1 ng cDNA | Expression |
|---|---|
| Mononuclear cells | X |
| Resting CD8+ cells | X |
| Resting CD4+ cells | |
| Resting CD14+ cells | |
| Resting CD19+ cells | X |
| Activated CD19+ cells | |
| Activated mononuclear cells | |
| Activated CD4+ cells | |
| Activated CD8+ cells | |
| Human Placenta | X |
| No template control | |
| Zcytor11 cDNA | X |

D. Tissue Distribution of Zcytor11 in Human Primary Immune Cell and Immune Cell Lines Using RT-PCR A panel of RNAs from primary human immune cell populations and human immune cell lines was screened for zcytor11 expression using RT-PCR. The panels were made in house and contained 24 RNAs from various resting and activated cell populations and cell lines as shown in Table 11 below. All primary immune cell populations were isolated from the blood of several anonymous donors. Various immune cell subsets (CD4+, CD8+, CD14+, CD19+, and CD56+) were then isolated using Microbeads and the Magnetic Cell Separation System from Miltenyi Biotec. RNA was prepared from the CD19+ and CD56+ populations in their resting state using an RNeasy Midiprep™ Kit (Qiagen, Valencia, Calif.) as per manufacturer's instruction. The CD4+, and CD8+ populations were activated using 200 ng/ml plate-bound anti-CD3 antibody and 5 μg/ml soluble anti-CD28 antibody and cells were collected for RNA isolation at 0, 4 and 16 hours. The CD19+ samples were isolated from human tonsil and activated with 0.5 μg/ml Ionomycin and 10 ng/ml PMA. Cells were then collected at 0, 4 hours and 24 hours and RNA isolated. Human CD14+ monocytes were activated with either 0.1 μg/ml LPS or 1.0 μg/ml LPS for 20 hours. Resting and activated cells were then collected and RNA isolated. In addition, RNA was isolated from resting and activated (10.0 μg/ml LPS) human monocyte cell lines HL-60, THP-1 and U937. Also, resting Raji, Ramos, Daudi, and Jurkat RNA's were tested.

The RT-PCR reactions used the Superscript One-Step RT-PCR System with Platinum Taq. Each 25 μl reaction consisted of the following: 12.5 μl of 2×Reaction Buffer, 0.5 μl (20 pmol.μl) ZC14,666 (SEQ ID NO:11), 0.5 μl (20 pmol/μl) ZC14,742 (SEQ ID NO:12), 0.4 μl RT/Taq polymerase mix, 10 μl RNase-free water, 1.0 μl template RNA (100 ng/μl). (Life Technologies, Gaithersburg, Md.). The amplification was carried out as follows: one cycle at 50° for 30 minutes followed by 35 cycles of 94°, 30 seconds; 52°, 30 seconds; 72°, 60 seconds; then ended with a final extension at 72° for 7 minutes. 8 to 10 μl of the PCR reaction product was subjected to standard Agarose gel electrophoresis using a 2% agarose gel. The correct predicted cDNA fragment size was observed in resting CD19+ B cells and much less in the activated CD19+ B cells, resting CD8+ T cells, CD56+ NK cells and activated CD14+ monocytes. Cell lines showing expression of zcytor11 were Jurkat, activated THP-1 and activated HL-60. Zcytor11 expression was not observed in the other tissues and cell lines tested in this panel. These results demonstrate the expression of zcytor11 in several immune cell populations and immune cell lines.

TABLE 11

| Tissue | # samples | Tissue | # samples |
|---|---|---|---|
| CD19+ from resting PBMCs | 1 | CD14+ 0.1 μg/ml LPS | 1 |
| CD19+ resting from tonsil | 1 | CD14+ 1.0 μg/ml LPS | 1 |
| CD19+ from tonsil - 4 hr activation | 1 | Raji | 1 |
| CD19+ from tonsil - 16 hr activation | 1 | Ramos | 1 |
| CD4+ Resting | 1 | Daudi | 1 |
| CD4+ 4 hr Activation | 1 | Jurkat | 1 |
| CD4+ 16 hr Activation | 1 | U937 | 1 |
| CD8+ Resting | 1 | Activated U937 | 1 |
| CD8+ 4 hr Activation | 1 | THP-1 | 1 |
| CD8+ 16 hr Activation | 1 | Activated THP-1 | 1 |
| CD56+ Resting | 1 | HL-60 | 1 |
| CD14+ Resting | 1 | Activated HL-60 | 1 |

EXAMPLE 16

Construction of BaF3 Cells Expressing the CRF2-4 Receptor (BaF3/CRF2-4 Cells) and BaF3 Cells Expressing the CRF2-4 Receptor with the zcytor11 Receptor (BaF3/CRF2-4/zcytor11 Cells)

BaF3 cells expressing the full-length CFR2-4 receptor were constructed, using 30 μg of a CFR2-4 expression vector, described below. The BaF3 cells expressing the CFR2-4 receptor were designated as BaF3/CFR2-4. These cells were used as a control, and were further transfected with full-length zcytor11 receptor (U.S. Pat. No. 5,965,704) and used to construct a screen for IL-TIF activity as described below.

A. Construction of BaF3 Cells Expressing the CRF2-4 Receptor

The full-length cDNA sequence of CRF2-4 (Genbank Accession No. Z17227) was isolated from a Daudi cell line cDNA library, and then cloned into an expression vector pZP7P.

BaF3, an interleukin-3 (IL-3) dependent pre-lymphoid cell line derived from murine bone marrow (Palacios and Steinmetz, *Cell* 41: 727–734, 1985; Mathey-Prevot et al., *Mol. Cell. Biol.* 6: 4133–4135, 1986), was maintained in complete media (RPMI medium (JRH Bioscience Inc., Lenexa, Kans.) supplemented with 10% heat-inactivated fetal calf serum, 2 ng/ml murine IL-3 (mIL-3) (R & D, Minneapolis, Minn.), 2 mM L-glutaMax-1™ (Gibco BRL), 1 mM Sodium Pyruvate (Gibco BRL), and PSN antibiotics (GIBCO BRL)). Prior to electroporation, CRF2-4/pZP7P was prepared and purified using a Qiagen Maxi Prep kit (Qiagen) as per manufacturer's instructions. For electroporation, BaF3 cells were washed once in serum-free RPMI media and then resuspended in serum-free RPMI media at a cell density of $10^7$ cells/ml. One ml of resuspended BaF3 cells was mixed with 30 μg of the CRF2-4/pZP7P plasmid DNA and transferred to separate disposable electroporation chambers (GIBCO BRL). Following a 15-minute incubation at room temperature the cells were given two serial shocks (800 lFad/300 V.; 1180 lFad/300 V.) delivered by an electroporation apparatus (CELL-PORATOR™; GIBCO BRL). After a 5-minute recovery time, the electroporated cells were transferred to 50 ml of complete media and placed in an incubator for 15–24 hours (37° C., 5% $CO_2$). The cells were then spun down and resuspended in 50 ml of complete media containing 2 μg/ml puromycin in a T-162 flask to isolate the puromycin-resistant pool. Pools of the transfected BaF3 cells, hereinafter called BaF3/CRF2-4 cells, were assayed for signaling capability as described below. Moreover these cells were further transfected with zcytor11 receptor as described below.

B. Construction of BaF3 Cells Expressing CRF2-4 and zcytor11 Receptors

BaF3/CRF2-4 cells expressing the full-length zcytor11 receptor were constructed as per Example 5A above, using 30 μg of the zcytor11 expression vector, described in Example 6 above. Following recovery, transfectants were selected using 200 μg/ml zeocin and 2 μg/ml puromycin. The BaF3/CRF2-4 cells expressing the zcytor11 receptor were designated as BaF3/CRF2-4/zcytor11 cells. These cells were used to screen for IL-TIF activity as well as zcytor16 antagonist activity described IN Example 17.

EXAMPLE 17

Screening for CRF2-4Zcytor11-Fc Activity Using BaF3/CRF2-4/zcytor11 Cells in an Alamar Blue Proliferation Assay BaF3/CRF2-4/zcytor11 cells (Example 16) were spun down and washed in PBS 2 times to ensure the removal of the mIL-3, and then spun a third time and resuspended in the complete media, (RPMI 1640, 10% FBS, 1% GlutaMAX, 1% Sodium Pyruvate) described in Example 16 above, but without mIL-3 (hereinafter referred to as "mIL-3 free media"). Cells were then counted in a hemocytometer. Cells were plated in a 96-well format at 5000 cells per well in a volume of 50 µl per well using the mIL-3 free media.

IL-TIF protein was diluted to 200 pg/ml in mIL-3 free media and also in CRF2-4/zcytor11-Fc conditioned media at a concentration of approximately 0.4 ug/ml that was made from transfected BHK cells (Example 7). The CRF2-4/zcytor11-Fc CM was diluted into the mIL-3 free/IL-TIF media by serial 1:2 dilutions down all 8 rows on the 96-well plate, leaving a volume of 50 ul in each well. This was then added to the 50 ul of cells, for a final IL-TIF concentration of 100 pg/ml in all wells, and final CRF2-4/zcytor11-Fc concentrations of approximately 200, 100, 50, 25, 12.5, 6.25, 3.1 and 1.6 ng/ml, and a total assay volume of 100 µl. The assay plates were incubated at 37° C., 5% $CO_2$ for 4 days at which time Alamar Blue (Accumed, Chicago, Ill.) was added at 20 µl/well. Plates were again incubated at 37° C., 5% $CO_2$ for 24 hours. Alamar Blue gives a fluourometric readout based on number of live cells, and is thus a direct measurement of cell proliferation in comparison to a negative control. Plates were read on the Wallac Victor 2 1420 Multilabel Counter (Wallac, Turku, Finland) at wavelengths 530 (Excitation) and 590 (Emmssion).

Results confirmed a dose-dependant inhibition by CRF2-4/zcytor11-Fc of the proliferative effect of IL-TIF on BaF3/CRF2-4/zcytor11 cells. IL-TIF alone stimulated the cells 30-fold over background. CRF2-4/zcytor11-Fc completely inhibited that proliferation at concentrations of 25–200 ng/ml, partially inhibited proliferation at 3.1–12.5 ng/ml, and inhibition was barely detectable at 1.6 ng/ml. The same setup was done with mIL-TIF, and generated similar results.

EXAMPLE 18

Flow Cytometry Analysis of Baf3-Transfectants Expressing zcytor11 Alone CRF2-4 Alone, zcytor11/CRF-4, or zcytor11/pDIRS1

BaF3 cells transfected with zcytor11 alone, CRF2-4 alone, zcytor11/CRF2-4, or zcytor11/pDIRS1 were generated with each respective cytokine receptor, as described (Example 16). Briefly, 30 ug of zcytor11/pZP7Z were transfected into BaF3 cells using electroporation, and the stable transfectants (BaF3/zcytor11) were selected with 200 µg/ml zeocin. Similarly BaF3 cells transfected with CRF2-4/pZP7P (BaF3/CRF2-4) were selected with 2 µg/ml puromycin. Subsequently, 30 ug of CRF2-4/pZP7P were transfected into BaF3/zcytor11 cells using electroporation, and the stable cell line (BaF3/zcytor11/CRF2-4) was selected with 200 µg/ml zeocin and 2 µg/ml puromycin. Similarly, 30 ug of pDIRS1/pZP7P were transfected into BaF3/zcytor11 cells using electroporation, and the stable cell line (BaF3/zcytor11/pDIRS1) was selected with 200 µg/ml zeocin and 2 ug/ml puromycin. The BHK transfectants were generated using the same expression vectors of either zcytor11, CRF2-4, or pDIRS1 for BaF3 transfectants. DNA was transfected into BHK cells using Lipofectamine™ (Gibco BRL, Gaitersburg, Md.) as per manufacturer's instructions, the selection was started 48-hr post-transfection following the same protocol for BaF3 selection.

The biotinylation of human IL-TIF-CEE (Example 12) protein is done as follows: 1.6 ul 10% Tween20, 50 ul 1M boric acid (pH 8.5), and 42 ul of 0.9 mg/ml EZ-link Sulfo-NHS-LC-biotin (Pierce, Rockford, Ill.) dissolved in DMSO were added into 100 ul of 2.2 mg/ml IL-TIF-CEE. After 1 hr incubation at room temperature, the reaction was quenched with 10 ul of 2M glycine for 10 minutes.

To test the binding properties of the IL-TIF ligand to several potential receptor components, BaF3 and BHK cells were transfected with expression plasmids including zcytor11 alone, CRF2-4 alone (Genbank Accession No. Z17227), zcytor11 (SEQ ID NO:1) and CRF2-4, or zcytoR11 and pDIRS1 (WIPO Publication WO99/46379, Schering Corporation, 1999), as described above. Untransfected BaF3 and BHK cells were included as controls. Cells were resuspended in FACS wash buffer (WB: PBS/1% BSA, supplemented with 3% human Ultraserum (Gemini Bio-Products, Calabasas, Calif.)) counted and $1\times10^6$ of each type were aliquoted into 5 ml polystyrene tubes. Cells were washed and pelleted, then incubated for 20 min on ice with 100 µl of WB only, or WB plus 10 µg/ml or 1 µg/ml biotinylated zcyto10 protein. Cells were washed with 1.5 ml WB and pelleted, then incubated in 100 µl of 2.5 µg/ml phycoerthyrin-conjugated streptavidin (PE-SA, PharMingen, San Diego, Calif.) for another 20 min on ice. Cells were washed as before, resuspended in 0.4 ml of WB and analyzed on a FACScan using CellQuest software (Becton Dickinson, Mountain View, Calif.).

The biotin-IL-TIF bound in a dose-dependent fashion to all 3 of the transfected BaF3 cell lines containing zcytor11 (i.e. zcytor11 transfected alone, or in combination with CRF2-4 or DIRS1), but not to the parental line or to the BaF3×CRF2-4 transfectant. The same results were obtained with the corresponding BHK transfectants.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method for inhibiting IL-TIF-induced proliferation of neutrophils or platelets comprising culturing bone marrow or peripheral blood cells with a composition comprising an amount of soluble cytokine receptor comprising SEQ ID NO:3 sufficient to reduce proliferation of the neutrophils or platelets in the bone marrow or peripheral blood cells as compared to bone marrow or peripheral blood cells cultured in the absence of the soluble cytokine receptor.

2. The method of claim 1, wherein the soluble cytokine receptor further comprises a soluble CRF2-4 polypeptide (SEQ ID NO:33).

3. An isolated soluble cytokine receptor polypeptide complex comprising more than one soluble receptor subunit, wherein at least one of the soluble receptor subunits comprises the sequence of amino acid residues shown in SEQ ID NO:3, and wherein a second soluble receptor subunit comprises the soluble CRF2-4 polypeptide (SEQ ID NO:33, and wherein the soluble cytokine receptor polypeptide binds IL-TIF or antagonizes IL-TIF activity.

4. An isolated soluble cytokine receptor polypeptide complex consisting of two soluble receptor subunits, wherein at least one of the soluble receptor subunits consists of the sequence of amino acid residues shown in SEQ ID NO:3, and wherein a second soluble receptor subunit consists of soluble CRF2-4 polypeptide (SEQ ID NO:33), and wherein the soluble cytokine receptor polypeptide binds IL-TIF or antagonizes IL-TIF activity.

5. An isolated polypeptide according to claim 3, wherein the soluble cytokine receptor polypeptide comprises a heterodimeric receptor complex.

6. The isolated polypeptide according to claim 3, wherein the soluble cytokine receptor polypeptide comprises a multimeric receptor complex.

7. An isolated polypeptide according to claim 3, wherein the soluble cytokine receptor polypeptide further comprises an affinity tag, label, chemical moiety, toxin, biotin/avidin label, radionuclide, enzyme, substrate, cofactor, inhibitor, fluorescent marker, chemiluminescent marker, cytotoxic molecule or an immunoglobulin Fc domain.

8. An isolated polypeptide according to claim 4, wherein the soluble cytokine receptor polypeptide comprises a heterodimeric receptor receptor complex.

9. An isolated polypeptide according to claim 4, wherein the soluble cytokine receptor polypeptide further comprises an affinity tag, label, chemical moiety, toxin, biotin/avidin label, radionuclide, enzyme, substrate, cofactor, inhibitor, fluorescent marker, chemiluminescent marker, cytotoxic molecule or an immunoglobulin Fc domain.

* * * * *

SEQUENCE LISTING

```
<160> NUMBER OF SEQ ID NOS: 35

<210> SEQ ID NO 1
<211> LENGTH: 2831
<212> TYPE: DNA
<213> ORGANISM: Homo sapien
<220> FEATURE:
<221> NAME/KEY: CDS
<222> LOCATION: (34)...(1755)
```

-continued

```
<400> SEQUENCE: 1

tagaggccaa gggagggctc tgtgccagcc ccg atg agg acg ctg ctg acc atc       54
                                     Met Arg Thr Leu Leu Thr Ile
                                      1               5

ttg act gtg gga tcc ctg gct gct cac gcc cct gag gac ccc tcg gat       102
Leu Thr Val Gly Ser Leu Ala Ala His Ala Pro Glu Asp Pro Ser Asp
         10                  15                  20

ctg ctc cag cac gtg aaa ttc cag tcc agc aac ttt gaa aac atc ctg       150
Leu Leu Gln His Val Lys Phe Gln Ser Ser Asn Phe Glu Asn Ile Leu
     25                  30                  35

acg tgg gac agc ggg cca gag ggc acc cca gac acg gtc tac agc atc       198
Thr Trp Asp Ser Gly Pro Glu Gly Thr Pro Asp Thr Val Tyr Ser Ile
 40                  45                  50                  55

gag tat aag acg tac gga gag agg gac tgg gtg gca aag aag ggc tgt       246
Glu Tyr Lys Thr Tyr Gly Glu Arg Asp Trp Val Ala Lys Lys Gly Cys
                 60                  65                  70

cag cgg atc acc cgg aag tcc tgc aac ctg acg gtg gag acg ggc aac       294
Gln Arg Ile Thr Arg Lys Ser Cys Asn Leu Thr Val Glu Thr Gly Asn
             75                  80                  85

ctc acg gag ctc tac tat gcc agg gtc acc gct gtc agt gcg gga ggc       342
Leu Thr Glu Leu Tyr Tyr Ala Arg Val Thr Ala Val Ser Ala Gly Gly
         90                  95                 100

cgg tca gcc acc aag atg act gac agg ttc agc tct ctg cag cac act       390
Arg Ser Ala Thr Lys Met Thr Asp Arg Phe Ser Ser Leu Gln His Thr
    105                 110                 115

acc ctc aag cca cct gat gtg acc tgt atc tcc aaa gtg aga tcg att       438
Thr Leu Lys Pro Pro Asp Val Thr Cys Ile Ser Lys Val Arg Ser Ile
120                 125                 130                 135

cag atg att gtt cat cct acc ccc acg cca atc cgt gca ggc gat ggc       486
Gln Met Ile Val His Pro Thr Pro Thr Pro Ile Arg Ala Gly Asp Gly
                140                 145                 150

cac cgg cta acc ctg gaa gac atc ttc cat gac ctg ttc tac cac tta       534
His Arg Leu Thr Leu Glu Asp Ile Phe His Asp Leu Phe Tyr His Leu
            155                 160                 165

gag ctc cag gtc aac cgc acc tac caa atg cac ctt gga ggg aag cag       582
Glu Leu Gln Val Asn Arg Thr Tyr Gln Met His Leu Gly Gly Lys Gln
        170                 175                 180

aga gaa tat gag ttc ttc ggc ctg acc cct gac aca gag ttc ctt ggc       630
Arg Glu Tyr Glu Phe Phe Gly Leu Thr Pro Asp Thr Glu Phe Leu Gly
    185                 190                 195

acc atc atg att tgc gtt ccc acc tgg gcc aag gag agt gcc ccc tac       678
Thr Ile Met Ile Cys Val Pro Thr Trp Ala Lys Glu Ser Ala Pro Tyr
200                 205                 210                 215

atg tgc cga gtg aag aca ctg cca gac cgg aca tgg acc tac tcc ttc       726
Met Cys Arg Val Lys Thr Leu Pro Asp Arg Thr Trp Thr Tyr Ser Phe
                220                 225                 230

tcc gga gcc ttc ctg ttc tcc atg ggc ttc ctc gtc gca gta ctc tgc       774
Ser Gly Ala Phe Leu Phe Ser Met Gly Phe Leu Val Ala Val Leu Cys
            235                 240                 245

tac ctg agc tac aga tat gtc acc aag ccg cct gca cct ccc aac tcc       822
Tyr Leu Ser Tyr Arg Tyr Val Thr Lys Pro Pro Ala Pro Pro Asn Ser
        250                 255                 260

ctg aac gtc cag cga gtc ctg act ttc cag ccg ctg cgc ttc atc cag       870
Leu Asn Val Gln Arg Val Leu Thr Phe Gln Pro Leu Arg Phe Ile Gln
    265                 270                 275

gag cac gtc ctg atc cct gtc ttt gac ctc agc ggc ccc agc agt ctg       918
Glu His Val Leu Ile Pro Val Phe Asp Leu Ser Gly Pro Ser Ser Leu
280                 285                 290                 295
```

-continued

```
gcc cag cct gtc cag tac tcc cag atc agg gtg tct gga ccc agg gag      966
Ala Gln Pro Val Gln Tyr Ser Gln Ile Arg Val Ser Gly Pro Arg Glu
                300                 305                 310

ccc gca gga gct cca cag cgg cat agc ctg tcc gag atc acc tac tta     1014
Pro Ala Gly Ala Pro Gln Arg His Ser Leu Ser Glu Ile Thr Tyr Leu
            315                 320                 325

ggg cag cca gac atc tcc atc ctc cag ccc tcc aac gtg cca cct ccc     1062
Gly Gln Pro Asp Ile Ser Ile Leu Gln Pro Ser Asn Val Pro Pro Pro
        330                 335                 340

cag atc ctc tcc cca ctg tcc tat gcc cca aac gct gcc cct gag gtc     1110
Gln Ile Leu Ser Pro Leu Ser Tyr Ala Pro Asn Ala Ala Pro Glu Val
    345                 350                 355

ggg ccc cca tcc tat gca cct cag gtg acc ccc gaa gct caa ttc cca     1158
Gly Pro Pro Ser Tyr Ala Pro Gln Val Thr Pro Glu Ala Gln Phe Pro
360                 365                 370                 375

ttc tac gcc cca cag gcc atc tct aag gtc cag cct tcc tcc tat gcc     1206
Phe Tyr Ala Pro Gln Ala Ile Ser Lys Val Gln Pro Ser Ser Tyr Ala
                380                 385                 390

cct caa gcc act ccg gac agc tgg cct ccc tcc tat ggg gta tgc atg     1254
Pro Gln Ala Thr Pro Asp Ser Trp Pro Pro Ser Tyr Gly Val Cys Met
            395                 400                 405

gaa ggt tct ggc aaa gac tcc ccc act ggg aca ctt tct agt cct aaa     1302
Glu Gly Ser Gly Lys Asp Ser Pro Thr Gly Thr Leu Ser Ser Pro Lys
        410                 415                 420

cac ctt agg cct aaa ggt cag ctt cag aaa gag cca cca gct gga agc     1350
His Leu Arg Pro Lys Gly Gln Leu Gln Lys Glu Pro Pro Ala Gly Ser
    425                 430                 435

tgc atg tta ggt ggc ctt tct ctg cag gag gtg acc tcc ttg gct atg     1398
Cys Met Leu Gly Gly Leu Ser Leu Gln Glu Val Thr Ser Leu Ala Met
440                 445                 450                 455

gag gaa tcc caa gaa gca aaa tca ttg cac cag ccc ctg ggg att tgc     1446
Glu Glu Ser Gln Glu Ala Lys Ser Leu His Gln Pro Leu Gly Ile Cys
                460                 465                 470

aca gac aga aca tct gac cca aat gtg cta cac agt ggg gag gaa ggg     1494
Thr Asp Arg Thr Ser Asp Pro Asn Val Leu His Ser Gly Glu Glu Gly
            475                 480                 485

aca cca cag tac cta aag ggc cag ctc ccc ctc ctc tcc tca gtc cag     1542
Thr Pro Gln Tyr Leu Lys Gly Gln Leu Pro Leu Leu Ser Ser Val Gln
        490                 495                 500

atc gag ggc cac ccc atg tcc ctc cct ttg caa cct cct tcc ggt cca     1590
Ile Glu Gly His Pro Met Ser Leu Pro Leu Gln Pro Pro Ser Gly Pro
    505                 510                 515

tgt tcc ccc tcg gac caa ggt cca agt ccc tgg ggc ctg ctg gag tcc     1638
Cys Ser Pro Ser Asp Gln Gly Pro Ser Pro Trp Gly Leu Leu Glu Ser
520                 525                 530                 535

ctt gtg tgt ccc aag gat gaa gcc aag agc cca gcc cct gag acc tca     1686
Leu Val Cys Pro Lys Asp Glu Ala Lys Ser Pro Ala Pro Glu Thr Ser
                540                 545                 550

gac ctg gag cag ccc aca gaa ctg gat tct ctt ttc aga ggc ctg gcc     1734
Asp Leu Glu Gln Pro Thr Glu Leu Asp Ser Leu Phe Arg Gly Leu Ala
            555                 560                 565

ctg act gtg cag tgg gag tcc tgaggggaat gggaaaggct tggtgcttcc        1785
Leu Thr Val Gln Trp Glu Ser
        570

tccctgtccc tacccagtgt cacatccttg gctgtcaatc ccatgcctgc ccatgccaca   1845

cactctgcga tctggcctca gacgggtgcc cttgagagaa gcagagggag tggcatgcag   1905

ggcccctgcc atgggtgcgc tcctcaccgg aacaaagcag catgataagg actgcagcgg   1965

gggagctctg gggagcagct tgtgtagaca agcgcgtgct cgctgagccc tgcaaggcag   2025
```

-continued

```
aaatgacagt gcaaggagga aatgcaggga aactcccgag gtccagagcc ccacctccta   2085

acaccatgga ttcaaagtgc tcagggaatt tgcctctcct tgccccattc ctggccagtt   2145

tcacaatcta gctcgacaga gcatgaggcc cctgcctctt ctgtcattgt tcaaaggtgg   2205

gaagagagcc tggaaaagaa ccaggcctgg aaaagaacca gaaggaggct gggcagaacc   2265

agaacaacct gcacttctgc caaggccagg gccagcagga cggcaggact ctagggaggg   2325

gtgtggcctg cagctcattc ccagccaggg caactgcctg acgttgcacg atttcagctt   2385

cattcctctg atagaacaaa gcgaaatgca ggtccaccag ggagggagac acacaagcct   2445

tttctgcagg caggagtttc agaccctatc ctgagaatgg ggtttgaaag gaaggtgagg   2505

gctgtggccc ctggacgggt acaataacac actgtactga tgtcacaact ttgcaagctc   2565

tgccttgggt tcagcccatc tgggctcaaa ttccagcctc accactcaca agctgtgtga   2625

cttcaaacaa atgaaatcag tgcccagaac ctcggtttcc tcatctgtaa tgtggggatc   2685

ataacaccta cctcatggag ttgtggtgaa gatgaaatga agtcatgtct ttaaagtgct   2745

taatagtgcc tggtacatgg gcagtgccca ataaacggta gctatttaaa aaaaaaaaaa   2805

aaaaaaaaaa atagcggccg cctcga                                        2831


<210> SEQ ID NO 2
<211> LENGTH: 574
<212> TYPE: PRT
<213> ORGANISM: Homo sapien

<400> SEQUENCE: 2

Met Arg Thr Leu Leu Thr Ile Leu Thr Val Gly Ser Leu Ala Ala His
1               5                   10                  15

Ala Pro Glu Asp Pro Ser Asp Leu Leu Gln His Val Lys Phe Gln Ser
            20                  25                  30

Ser Asn Phe Glu Asn Ile Leu Thr Trp Asp Ser Gly Pro Glu Gly Thr
        35                  40                  45

Pro Asp Thr Val Tyr Ser Ile Glu Tyr Lys Thr Tyr Gly Glu Arg Asp
    50                  55                  60

Trp Val Ala Lys Lys Gly Cys Gln Arg Ile Thr Arg Lys Ser Cys Asn
65                  70                  75                  80

Leu Thr Val Glu Thr Gly Asn Leu Thr Glu Leu Tyr Tyr Ala Arg Val
                85                  90                  95

Thr Ala Val Ser Ala Gly Gly Arg Ser Ala Thr Lys Met Thr Asp Arg
            100                 105                 110

Phe Ser Ser Leu Gln His Thr Thr Leu Lys Pro Pro Asp Val Thr Cys
        115                 120                 125

Ile Ser Lys Val Arg Ser Ile Gln Met Ile Val His Pro Thr Pro Thr
    130                 135                 140

Pro Ile Arg Ala Gly Asp Gly His Arg Leu Thr Leu Glu Asp Ile Phe
145                 150                 155                 160

His Asp Leu Phe Tyr His Leu Glu Leu Gln Val Asn Arg Thr Tyr Gln
                165                 170                 175

Met His Leu Gly Gly Lys Gln Arg Glu Tyr Glu Phe Phe Gly Leu Thr
            180                 185                 190

Pro Asp Thr Glu Phe Leu Gly Thr Ile Met Ile Cys Val Pro Thr Trp
        195                 200                 205

Ala Lys Glu Ser Ala Pro Tyr Met Cys Arg Val Lys Thr Leu Pro Asp
    210                 215                 220
```

-continued

```
Arg Thr Trp Thr Tyr Ser Phe Ser Gly Ala Phe Leu Phe Ser Met Gly
225                 230                 235                 240

Phe Leu Val Ala Val Leu Cys Tyr Leu Ser Tyr Arg Tyr Val Thr Lys
                245                 250                 255

Pro Pro Ala Pro Pro Asn Ser Leu Asn Val Gln Arg Val Leu Thr Phe
            260                 265                 270

Gln Pro Leu Arg Phe Ile Gln Glu His Val Leu Ile Pro Val Phe Asp
        275                 280                 285

Leu Ser Gly Pro Ser Ser Leu Ala Gln Pro Val Gln Tyr Ser Gln Ile
    290                 295                 300

Arg Val Ser Gly Pro Arg Glu Pro Ala Gly Ala Pro Gln Arg His Ser
305                 310                 315                 320

Leu Ser Glu Ile Thr Tyr Leu Gly Gln Pro Asp Ile Ser Ile Leu Gln
                325                 330                 335

Pro Ser Asn Val Pro Pro Pro Gln Ile Leu Ser Pro Leu Ser Tyr Ala
            340                 345                 350

Pro Asn Ala Ala Pro Glu Val Gly Pro Pro Ser Tyr Ala Pro Gln Val
        355                 360                 365

Thr Pro Glu Ala Gln Phe Pro Phe Tyr Ala Pro Gln Ala Ile Ser Lys
    370                 375                 380

Val Gln Pro Ser Ser Tyr Ala Pro Gln Ala Thr Pro Asp Ser Trp Pro
385                 390                 395                 400

Pro Ser Tyr Gly Val Cys Met Glu Gly Ser Gly Lys Asp Ser Pro Thr
                405                 410                 415

Gly Thr Leu Ser Ser Pro Lys His Leu Arg Pro Lys Gly Gln Leu Gln
            420                 425                 430

Lys Glu Pro Pro Ala Gly Ser Cys Met Leu Gly Gly Leu Ser Leu Gln
        435                 440                 445

Glu Val Thr Ser Leu Ala Met Glu Glu Ser Gln Glu Ala Lys Ser Leu
    450                 455                 460

His Gln Pro Leu Gly Ile Cys Thr Asp Arg Thr Ser Asp Pro Asn Val
465                 470                 475                 480

Leu His Ser Gly Glu Glu Gly Thr Pro Gln Tyr Leu Lys Gly Gln Leu
                485                 490                 495

Pro Leu Leu Ser Ser Val Gln Ile Glu Gly His Pro Met Ser Leu Pro
            500                 505                 510

Leu Gln Pro Pro Ser Gly Pro Cys Ser Pro Ser Asp Gln Gly Pro Ser
        515                 520                 525

Pro Trp Gly Leu Leu Glu Ser Leu Val Cys Pro Lys Asp Glu Ala Lys
    530                 535                 540

Ser Pro Ala Pro Glu Thr Ser Asp Leu Glu Gln Pro Thr Glu Leu Asp
545                 550                 555                 560

Ser Leu Phe Arg Gly Leu Ala Leu Thr Val Gln Trp Glu Ser
                565                 570


<210> SEQ ID NO 3
<211> LENGTH: 211
<212> TYPE: PRT
<213> ORGANISM: Homo sapiens

<400> SEQUENCE: 3

Pro Glu Asp Pro Ser Asp Leu Leu Gln His Val Lys Phe Gln Ser Ser
 1               5                  10                  15

Asn Phe Glu Asn Ile Leu Thr Trp Asp Ser Gly Pro Glu Gly Thr Pro
            20                  25                  30
```

-continued

```
Asp Thr Val Tyr Ser Ile Glu Tyr Lys Thr Tyr Gly Glu Arg Asp Trp
        35                  40                  45

Val Ala Lys Lys Gly Cys Gln Arg Ile Thr Arg Lys Ser Cys Asn Leu
    50                  55                  60

Thr Val Glu Thr Gly Asn Leu Thr Glu Leu Tyr Tyr Ala Arg Val Thr
65                  70                  75                  80

Ala Val Ser Ala Gly Gly Arg Ser Ala Thr Lys Met Thr Asp Arg Phe
                85                  90                  95

Ser Ser Leu Gln His Thr Thr Leu Lys Pro Pro Asp Val Thr Cys Ile
            100                 105                 110

Ser Lys Val Arg Ser Ile Gln Met Ile Val His Pro Thr Pro Thr Pro
        115                 120                 125

Ile Arg Ala Gly Asp Gly His Arg Leu Thr Leu Glu Asp Ile Phe His
    130                 135                 140

Asp Leu Phe Tyr His Leu Glu Leu Gln Val Asn Arg Thr Tyr Gln Met
145                 150                 155                 160

His Leu Gly Gly Lys Gln Arg Glu Tyr Glu Phe Phe Gly Leu Thr Pro
                165                 170                 175

Asp Thr Glu Phe Leu Gly Thr Ile Met Ile Cys Val Pro Thr Trp Ala
            180                 185                 190

Lys Glu Ser Ala Pro Tyr Met Cys Arg Val Lys Thr Leu Pro Asp Arg
        195                 200                 205

Thr Trp Thr
    210


<210> SEQ ID NO 4
<211> LENGTH: 6
<212> TYPE: PRT
<213> ORGANISM: Artificial Sequence
<220> FEATURE:
<223> OTHER INFORMATION: Glu-Glu peptide tag

<400> SEQUENCE: 4

Glu Tyr Met Pro Met Glu
 1               5


<210> SEQ ID NO 5
<211> LENGTH: 8
<212> TYPE: PRT
<213> ORGANISM: Artificial Sequence
<220> FEATURE:
<223> OTHER INFORMATION: Flag-tag peptide

<400> SEQUENCE: 5

Asp Tyr Lys Asp Asp Asp Asp Lys
 1               5


<210> SEQ ID NO 6
<211> LENGTH: 699
<212> TYPE: DNA
<213> ORGANISM: Homo sapiens

<400> SEQUENCE: 6

gagcccagat cttcagacaa aactcacaca tgcccaccgt gcccagcacc tgaagccgag      60

ggggcaccgt cagtcttcct cttcccccca aaacccaagg acaccctcat gatctcccgg     120

acccctgagg tcacatgcgt ggtggtggac gtgagccacg aagaccctga ggtcaagttc     180

aactggtacg tggacggcgt ggaggtgcat aatgccaaga caaagccgcg ggaggagcag     240

tacaacagca cgtaccgtgt ggtcagcgtc ctcaccgtcc tgcaccagga ctggctgaat     300
```

-continued

```
ggcaaggagt acaagtgcaa ggtctccaac aaagccctcc catcctccat cgagaaaacc    360

atctccaaag ccaaagggca gccccgagaa ccacaggtgt acaccctgcc cccatcccgg    420

gatgagctga ccaagaacca ggtcagcctg acctgcctgg tcaaaggctt ctatcccagc    480

gacatcgccg tggagtggga gagcaatggg cagccggaga acaactacaa gaccacgcct    540

cccgtgctgg actccgacgg ctccttcttc ctctacagca agctcaccgt ggacaagagc    600

aggtggcagc aggggaacgt cttctcatgc tccgtgatgc atgaggctct gcacaaccac    660

tacacgcaga agagcctctc cctgtctccg ggtaaataa                           699


<210> SEQ ID NO 7
<211> LENGTH: 1116
<212> TYPE: DNA
<213> ORGANISM: homo sapiens
<220> FEATURE:
<221> NAME/KEY: CDS
<222> LOCATION: (21)...(557)

<400> SEQUENCE: 7

tcgagttaga attgtctgca atg gcc gcc ctg cag aaa tct gtg agc tct ttc     53
                      Met Ala Ala Leu Gln Lys Ser Val Ser Ser Phe
                        1               5                  10

ctt atg ggg acc ctg gcc acc agc tgc ctc ctt ctc ttg gcc ctc ttg      101
Leu Met Gly Thr Leu Ala Thr Ser Cys Leu Leu Leu Leu Ala Leu Leu
            15                  20                  25

gta cag gga gga gca gct gcg ccc atc agc tcc cac tgc agg ctt gac      149
Val Gln Gly Gly Ala Ala Ala Pro Ile Ser Ser His Cys Arg Leu Asp
        30                  35                  40

aag tcc aac ttc cag cag ccc tat atc acc aac cgc acc ttc atg ctg      197
Lys Ser Asn Phe Gln Gln Pro Tyr Ile Thr Asn Arg Thr Phe Met Leu
    45                  50                  55

gct aag gag gct agc ttg gct gat aac aac aca gac gtt cgt ctc att      245
Ala Lys Glu Ala Ser Leu Ala Asp Asn Asn Thr Asp Val Arg Leu Ile
 60                  65                  70                  75

ggg gag aaa ctg ttc cac gga gtc agt atg agt gag cgc tgc tat ctg      293
Gly Glu Lys Leu Phe His Gly Val Ser Met Ser Glu Arg Cys Tyr Leu
                80                  85                  90

atg aag cag gtg ctg aac ttc acc ctt gaa gaa gtg ctg ttc cct caa      341
Met Lys Gln Val Leu Asn Phe Thr Leu Glu Glu Val Leu Phe Pro Gln
            95                 100                 105

tct gat agg ttc cag cct tat atg cag gag gtg gtg ccc ttc ctg gcc      389
Ser Asp Arg Phe Gln Pro Tyr Met Gln Glu Val Val Pro Phe Leu Ala
       110                 115                 120

agg ctc agc aac agg cta agc aca tgt cat att gaa ggt gat gac ctg      437
Arg Leu Ser Asn Arg Leu Ser Thr Cys His Ile Glu Gly Asp Asp Leu
    125                 130                 135

cat atc cag agg aat gtg caa aag ctg aag gac aca gtg aaa aag ctt      485
His Ile Gln Arg Asn Val Gln Lys Leu Lys Asp Thr Val Lys Lys Leu
140                 145                 150                 155

gga gag agt gga gag atc aaa gca att gga gaa ctg gat ttg ctg ttt      533
Gly Glu Ser Gly Glu Ile Lys Ala Ile Gly Glu Leu Asp Leu Leu Phe
                160                 165                 170

atg tct ctg aga aat gcc tgc att tgaccagagc aaagctgaaa aatgaataac     587
Met Ser Leu Arg Asn Ala Cys Ile
            175

taaccccctt tccctgctag aaataacaat tagatgcccc aaagcgattt tttttaacca    647

aaaggaagat gggaagccaa actccatcat gatgggtgga ttccaaatga acccctgcgt    707

tagttacaaa ggaaaccaat gccacttttg tttataagac cagaaggtag actttctaag    767
```

-continued catagatatt tattgataac atttcattgt aactggtgtt ctatacacag aaaacaattt 827 attttttaaa taattgtctt tttccataaa aaagattact ttccattcct ttaggggaaa 887 aaacccctaa atagcttcat gtttccataa tcagtacttt atatttataa atgtatttat 947 tattattata agactgcatt ttatttatat cattttatta atatggattt atttatagaa 1007 acatcattcg atattgctac ttgagtgtaa ggctaatatt gatatttatg acaataatta 1067 tagagctata acatgtttat ttgacctcaa taaacacttg gatatccta 1116

<210> SEQ ID NO 8
<211> LENGTH: 179
<212> TYPE: PRT
<213> ORGANISM: homo sapiens

<400> SEQUENCE: 8

```
Met Ala Ala Leu Gln Lys Ser Val Ser Ser Phe Leu Met Gly Thr Leu
 1               5                  10                  15

Ala Thr Ser Cys Leu Leu Leu Leu Ala Leu Leu Val Gln Gly Gly Ala
            20                  25                  30

Ala Ala Pro Ile Ser Ser His Cys Arg Leu Asp Lys Ser Asn Phe Gln
        35                  40                  45

Gln Pro Tyr Ile Thr Asn Arg Thr Phe Met Leu Ala Lys Glu Ala Ser
    50                  55                  60

Leu Ala Asp Asn Asn Thr Asp Val Arg Leu Ile Gly Glu Lys Leu Phe
65                  70                  75                  80

His Gly Val Ser Met Ser Glu Arg Cys Tyr Leu Met Lys Gln Val Leu
                85                  90                  95

Asn Phe Thr Leu Glu Glu Val Leu Phe Pro Gln Ser Asp Arg Phe Gln
            100                 105                 110

Pro Tyr Met Gln Glu Val Val Pro Phe Leu Ala Arg Leu Ser Asn Arg
        115                 120                 125

Leu Ser Thr Cys His Ile Glu Gly Asp Asp Leu His Ile Gln Arg Asn
    130                 135                 140

Val Gln Lys Leu Lys Asp Thr Val Lys Lys Leu Gly Glu Ser Gly Glu
145                 150                 155                 160

Ile Lys Ala Ile Gly Glu Leu Asp Leu Leu Phe Met Ser Leu Arg Asn
                165                 170                 175
Ala Cys Ile
```

<210> SEQ ID NO 9
<211> LENGTH: 36
<212> TYPE: DNA
<213> ORGANISM: Artificial Sequence
<220> FEATURE:
<223> OTHER INFORMATION: Oligonucleotide prime ZC28590

<400> SEQUENCE: 9
ttgggtacct ctgcaatggc cgccctgcag aaatct 36

<210> SEQ ID NO 10
<211> LENGTH: 33
<212> TYPE: DNA
<213> ORGANISM: Artificial Sequence
<220> FEATURE:
<223> OTHER INFORMATION: Oligonucleotide prime ZC28580

<400> SEQUENCE: 10
ttgggatcca atgcaggcat ttctcagaga cat 33

-continued

<210> SEQ ID NO 11
<211> LENGTH: 18
<212> TYPE: DNA
<213> ORGANISM: Artificial Sequence
<220> FEATURE:
<223> OTHER INFORMATION: Oligonucleotide prime ZC14666

<400> SEQUENCE: 11
agccaccaag atgactga 18

<210> SEQ ID NO 12
<211> LENGTH: 22
<212> TYPE: DNA
<213> ORGANISM: Artificial Sequence
<220> FEATURE:
<223> OTHER INFORMATION: Oligonucleotide prime ZC14742

<400> SEQUENCE: 12
tgcatttggt aggtgcggtt ga 22

<210> SEQ ID NO 13
<211> LENGTH: 6
<212> TYPE: PRT
<213> ORGANISM: Artificial Sequence
<220> FEATURE:
<223> OTHER INFORMATION: His tag

<400> SEQUENCE: 13

His His His His His His
1 5

<210> SEQ ID NO 14
<211> LENGTH: 63
<212> TYPE: DNA
<213> ORGANISM: Artificial Sequence
<220> FEATURE:
<223> OTHER INFORMATION: Oligonucleotide primer ZC29239

<400> SEQUENCE: 14
gaggccggat ccggttcggg ttcgggttcg gagcccagat catcagacaa aactcacaca 60
tgc 63

<210> SEQ ID NO 15
<211> LENGTH: 65
<212> TYPE: DNA
<213> ORGANISM: Artificial Sequence
<220> FEATURE:
<223> OTHER INFORMATION: Oligonucleotide primer ZC29232

<400> SEQUENCE: 15
cgactgactc gagtcagtga tggtgatggt gatggccacc tgatccttta cccggagaca 60
gggag 65

<210> SEQ ID NO 16
<211> LENGTH: 37
<212> TYPE: DNA
<213> ORGANISM: Artificial Sequence
<220> FEATURE:
<223> OTHER INFORMATION: Oligonucleotide primer ZC39319

<400> SEQUENCE: 16
atcggaattc gcagaagcca tggcgtggag ccttggg 37

-continued

```
<210> SEQ ID NO 17
<211> LENGTH: 28
<212> TYPE: DNA
<213> ORGANISM: Artificial Sequence
<220> FEATURE:
<223> OTHER INFORMATION: Oligonucleotide primer ZC39325

<400> SEQUENCE: 17

cagtggatcc ggaggggacc gtttcgtc                                      28


<210> SEQ ID NO 18
<211> LENGTH: 660
<212> TYPE: DNA
<213> ORGANISM: Homo sapiens
<220> FEATURE:
<221> NAME/KEY: CDS
<222> LOCATION: (1)...(660)

<400> SEQUENCE: 18

atg gcg tgg agt ctt ggg agc tgg ctg ggt ggc tgc ctg ctg gtg tca      48
Met Ala Trp Ser Leu Gly Ser Trp Leu Gly Gly Cys Leu Leu Val Ser
 1               5                  10                  15

gca ttg gga atg gta cca cct ccc gaa aat gtc aga atg aat tct gtt      96
Ala Leu Gly Met Val Pro Pro Pro Glu Asn Val Arg Met Asn Ser Val
            20                  25                  30

aat ttc aag aac att cta cag tgg gag tca cct gct ttt gcc aaa ggg     144
Asn Phe Lys Asn Ile Leu Gln Trp Glu Ser Pro Ala Phe Ala Lys Gly
        35                  40                  45

aac ctg act ttc aca gct cag tac cta agt tat agg ata ttc caa gat     192
Asn Leu Thr Phe Thr Ala Gln Tyr Leu Ser Tyr Arg Ile Phe Gln Asp
    50                  55                  60

aaa tgc atg aat act acc ttg acg gaa tgt gat ttc tca agt ctt tcc     240
Lys Cys Met Asn Thr Thr Leu Thr Glu Cys Asp Phe Ser Ser Leu Ser
 65                  70                  75                  80

aag tat ggt gac cac acc ttg aga gtc agg gct gaa ttt gca gat gag     288
Lys Tyr Gly Asp His Thr Leu Arg Val Arg Ala Glu Phe Ala Asp Glu
                85                  90                  95

cat tca gac tgg gta aac atc acc ttc tgt cct gtg gat gac acc att     336
His Ser Asp Trp Val Asn Ile Thr Phe Cys Pro Val Asp Asp Thr Ile
            100                 105                 110

att gga ccc cct gga atg caa gta gaa gta ctt gat gat tct tta cat     384
Ile Gly Pro Pro Gly Met Gln Val Glu Val Leu Asp Asp Ser Leu His
        115                 120                 125

atg cgt ttc tta gcc cct aaa att gag aat gaa tac gaa act tgg act     432
Met Arg Phe Leu Ala Pro Lys Ile Glu Asn Glu Tyr Glu Thr Trp Thr
    130                 135                 140

atg aag aat gtg tat aac tca tgg act tat aat gtg caa tac tgg aaa     480
Met Lys Asn Val Tyr Asn Ser Trp Thr Tyr Asn Val Gln Tyr Trp Lys
145                 150                 155                 160

aac ggt act gat gaa aag ttt caa att act ccc cag tat gac ttt gag     528
Asn Gly Thr Asp Glu Lys Phe Gln Ile Thr Pro Gln Tyr Asp Phe Glu
                165                 170                 175

gtc ctc aga aac ctg gag cca tgg aca act tat tgt gtt caa gtt cga     576
Val Leu Arg Asn Leu Glu Pro Trp Thr Thr Tyr Cys Val Gln Val Arg
            180                 185                 190

ggg ttt ctt cct gat cgg aac aaa gct ggg gaa tgg agt gag cct gtc     624
Gly Phe Leu Pro Asp Arg Asn Lys Ala Gly Glu Trp Ser Glu Pro Val
        195                 200                 205

tgt gag caa aca acc cat gac gaa acg gtc ccc tcc                     660
Cys Glu Gln Thr Thr His Asp Glu Thr Val Pro Ser
    210                 215                 220
```

-continued

<210> SEQ ID NO 19
<211> LENGTH: 220
<212> TYPE: PRT
<213> ORGANISM: Homo sapiens

<400> SEQUENCE: 19

```
Met Ala Trp Ser Leu Gly Ser Trp Leu Gly Gly Cys Leu Leu Val Ser
 1               5                  10                  15

Ala Leu Gly Met Val Pro Pro Pro Glu Asn Val Arg Met Asn Ser Val
            20                  25                  30

Asn Phe Lys Asn Ile Leu Gln Trp Glu Ser Pro Ala Phe Ala Lys Gly
        35                  40                  45

Asn Leu Thr Phe Thr Ala Gln Tyr Leu Ser Tyr Arg Ile Phe Gln Asp
    50                  55                  60

Lys Cys Met Asn Thr Thr Leu Thr Glu Cys Asp Phe Ser Ser Leu Ser
65                  70                  75                  80

Lys Tyr Gly Asp His Thr Leu Arg Val Arg Ala Glu Phe Ala Asp Glu
                85                  90                  95

His Ser Asp Trp Val Asn Ile Thr Phe Cys Pro Val Asp Asp Thr Ile
            100                 105                 110

Ile Gly Pro Pro Gly Met Gln Val Glu Val Leu Asp Asp Ser Leu His
        115                 120                 125

Met Arg Phe Leu Ala Pro Lys Ile Glu Asn Glu Tyr Glu Thr Trp Thr
    130                 135                 140

Met Lys Asn Val Tyr Asn Ser Trp Thr Tyr Asn Val Gln Tyr Trp Lys
145                 150                 155                 160

Asn Gly Thr Asp Glu Lys Phe Gln Ile Thr Pro Gln Tyr Asp Phe Glu
                165                 170                 175

Val Leu Arg Asn Leu Glu Pro Trp Thr Thr Tyr Cys Val Gln Val Arg
            180                 185                 190

Gly Phe Leu Pro Asp Arg Asn Lys Ala Gly Glu Trp Ser Glu Pro Val
        195                 200                 205

Cys Glu Gln Thr Thr His Asp Glu Thr Val Pro Ser
    210                 215                 220
```

<210> SEQ ID NO 20
<211> LENGTH: 18
<212> TYPE: DNA
<213> ORGANISM: Artificial Sequence
<220> FEATURE:
<223> OTHER INFORMATION: Oligonucleotide primer ZC38931

<400> SEQUENCE: 20

```
acaaagccgc gggaggag                                                    18
```

<210> SEQ ID NO 21
<211> LENGTH: 82
<212> TYPE: DNA
<213> ORGANISM: Artificial Sequence
<220> FEATURE:
<223> OTHER INFORMATION: Oligonucleotide primer ZC39042

<400> SEQUENCE: 21

```
ctgactcgag tcagtgatgg tgatggtgat ggccacctga tccggaacca cgcggaacca      60

gtttacccgg agacagggag ag                                               82
```

-continued

```
<210> SEQ ID NO 22
<211> LENGTH: 1428
<212> TYPE: DNA
<213> ORGANISM: Artificial Sequence
<220> FEATURE:
<221> NAME/KEY: CDS
<222> LOCATION: (1)...(1428)
<223> OTHER INFORMATION: CRF2-4 extracellular cytokine binding domain
      fused to IgGg1 with a 6-HIS tag

<400> SEQUENCE: 22

atg gcg tgg agt ctt ggg agc tgg ctg ggt ggc tgc ctg ctg gtg tca       48
Met Ala Trp Ser Leu Gly Ser Trp Leu Gly Gly Cys Leu Leu Val Ser
 1               5                  10                  15

gca ttg gga atg gta cca cct ccc gaa aat gtc aga atg aat tct gtt       96
Ala Leu Gly Met Val Pro Pro Pro Glu Asn Val Arg Met Asn Ser Val
            20                  25                  30

aat ttc aag aac att cta cag tgg gag tca cct gct ttt gcc aaa ggg      144
Asn Phe Lys Asn Ile Leu Gln Trp Glu Ser Pro Ala Phe Ala Lys Gly
        35                  40                  45

aac ctg act ttc aca gct cag tac cta agt tat agg ata ttc caa gat      192
Asn Leu Thr Phe Thr Ala Gln Tyr Leu Ser Tyr Arg Ile Phe Gln Asp
    50                  55                  60

aaa tgc atg aat act acc ttg acg gaa tgt gat ttc tca agt ctt tcc      240
Lys Cys Met Asn Thr Thr Leu Thr Glu Cys Asp Phe Ser Ser Leu Ser
 65                  70                  75                  80

aag tat ggt gac cac acc ttg aga gtc agg gct gaa ttt gca gat gag      288
Lys Tyr Gly Asp His Thr Leu Arg Val Arg Ala Glu Phe Ala Asp Glu
                 85                  90                  95

cat tca gac tgg gta aac atc acc ttc tgt cct gtg gat gac acc att      336
His Ser Asp Trp Val Asn Ile Thr Phe Cys Pro Val Asp Asp Thr Ile
            100                 105                 110

att gga ccc cct gga atg caa gta gaa gta ctt gat gat tct tta cat      384
Ile Gly Pro Pro Gly Met Gln Val Glu Val Leu Asp Asp Ser Leu His
        115                 120                 125

atg cgt ttc tta gcc cct aaa att gag aat gaa tac gaa act tgg act      432
Met Arg Phe Leu Ala Pro Lys Ile Glu Asn Glu Tyr Glu Thr Trp Thr
    130                 135                 140

atg aag aat gtg tat aac tca tgg act tat aat gtg caa tac tgg aaa      480
Met Lys Asn Val Tyr Asn Ser Trp Thr Tyr Asn Val Gln Tyr Trp Lys
145                 150                 155                 160

aac ggt act gat gaa aag ttt caa att act ccc cag tat gac ttt gag      528
Asn Gly Thr Asp Glu Lys Phe Gln Ile Thr Pro Gln Tyr Asp Phe Glu
                165                 170                 175

gtc ctc aga aac ctg gag cca tgg aca act tat tgt gtt caa gtt cga      576
Val Leu Arg Asn Leu Glu Pro Trp Thr Thr Tyr Cys Val Gln Val Arg
            180                 185                 190

ggg ttt ctt cct gat cgg aac aaa gct ggg gaa tgg agt gag cct gtc      624
Gly Phe Leu Pro Asp Arg Asn Lys Ala Gly Glu Trp Ser Glu Pro Val
        195                 200                 205

tgt gag caa aca acc cat gac gaa acg gtc ccc tcc gga tcc ggt tcg      672
Cys Glu Gln Thr Thr His Asp Glu Thr Val Pro Ser Gly Ser Gly Ser
    210                 215                 220

ggt tcg ggt tcg gag ccc aga tca tca gac aaa act cac aca tgc cca      720
Gly Ser Gly Ser Glu Pro Arg Ser Ser Asp Lys Thr His Thr Cys Pro
225                 230                 235                 240

ccg tgc cca gca cct gaa gcc gag ggg gca ccg tca gtc ttc ctc ttc      768
Pro Cys Pro Ala Pro Glu Ala Glu Gly Ala Pro Ser Val Phe Leu Phe
                245                 250                 255

ccc cca aaa ccc aag gac acc ctc atg atc tcc cgg acc cct gag gtc      816
Pro Pro Lys Pro Lys Asp Thr Leu Met Ile Ser Arg Thr Pro Glu Val
            260                 265                 270
```

-continued

```
aca tgc gtg gtg gtg gac gtg agc cac gaa gac cct gag gtc aag ttc      864
Thr Cys Val Val Val Asp Val Ser His Glu Asp Pro Glu Val Lys Phe
        275                 280                 285

aac tgg tac gtg gac ggc gtg gag gtg cat aat gcc aag aca aag ccg      912
Asn Trp Tyr Val Asp Gly Val Glu Val His Asn Ala Lys Thr Lys Pro
    290                 295                 300

cgg gag gag cag tac aac agc acg tac cgt gtg gtc agc gtc ctc acc      960
Arg Glu Glu Gln Tyr Asn Ser Thr Tyr Arg Val Val Ser Val Leu Thr
305                 310                 315                 320

gtc ctg cac cag gac tgg ctg aat ggc aag gag tac aag tgc aag gtc     1008
Val Leu His Gln Asp Trp Leu Asn Gly Lys Glu Tyr Lys Cys Lys Val
                325                 330                 335

tcc aac aaa gcc ctc cca tcc tcc atc gag aaa acc atc tcc aaa gcc     1056
Ser Asn Lys Ala Leu Pro Ser Ser Ile Glu Lys Thr Ile Ser Lys Ala
            340                 345                 350

aaa ggg cag ccc cga gaa cca cag gtg tac acc ctg ccc cca tcc cgg     1104
Lys Gly Gln Pro Arg Glu Pro Gln Val Tyr Thr Leu Pro Pro Ser Arg
        355                 360                 365

gat gag ctg acc aag aac cag gtc agc ctg acc tgc ctg gtc aaa ggc     1152
Asp Glu Leu Thr Lys Asn Gln Val Ser Leu Thr Cys Leu Val Lys Gly
    370                 375                 380

ttc tat ccc agc gac atc gcc gtg gag tgg gag agc aat ggg cag ccg     1200
Phe Tyr Pro Ser Asp Ile Ala Val Glu Trp Glu Ser Asn Gly Gln Pro
385                 390                 395                 400

gag aac aac tac aag acc acg cct ccc gtg ctg gac tcc gac ggc tcc     1248
Glu Asn Asn Tyr Lys Thr Thr Pro Pro Val Leu Asp Ser Asp Gly Ser
                405                 410                 415

ttc ttc ctc tac agc aag ctc acc gtg gac aag agc agg tgg cag cag     1296
Phe Phe Leu Tyr Ser Lys Leu Thr Val Asp Lys Ser Arg Trp Gln Gln
            420                 425                 430

ggg aac gtc ttc tca tgc tcc gtg atg cat gag gct ctg cac aac cac     1344
Gly Asn Val Phe Ser Cys Ser Val Met His Glu Ala Leu His Asn His
        435                 440                 445

tac acg cag aag agc ctc tcc ctg tct ccg ggt aaa ctg gtt ccg cgt     1392
Tyr Thr Gln Lys Ser Leu Ser Leu Ser Pro Gly Lys Leu Val Pro Arg
    450                 455                 460

ggt tcc gga tca ggt ggc cat cac cat cac cat cac                     1428
Gly Ser Gly Ser Gly Gly His His His His His His
465                 470                 475


<210> SEQ ID NO 23
<211> LENGTH: 476
<212> TYPE: PRT
<213> ORGANISM: Homo sapiens

<400> SEQUENCE: 23

Met Ala Trp Ser Leu Gly Ser Trp Leu Gly Gly Cys Leu Leu Val Ser
 1               5                  10                  15

Ala Leu Gly Met Val Pro Pro Pro Glu Asn Val Arg Met Asn Ser Val
            20                  25                  30

Asn Phe Lys Asn Ile Leu Gln Trp Glu Ser Pro Ala Phe Ala Lys Gly
        35                  40                  45

Asn Leu Thr Phe Thr Ala Gln Tyr Leu Ser Tyr Arg Ile Phe Gln Asp
    50                  55                  60

Lys Cys Met Asn Thr Thr Leu Thr Glu Cys Asp Phe Ser Ser Leu Ser
65                  70                  75                  80

Lys Tyr Gly Asp His Thr Leu Arg Val Arg Ala Glu Phe Ala Asp Glu
                85                  90                  95
```

-continued

```
His Ser Asp Trp Val Asn Ile Thr Phe Cys Pro Val Asp Asp Thr Ile
            100                 105                 110

Ile Gly Pro Pro Gly Met Gln Val Glu Val Leu Asp Asp Ser Leu His
        115                 120                 125

Met Arg Phe Leu Ala Pro Lys Ile Glu Asn Glu Tyr Glu Thr Trp Thr
    130                 135                 140

Met Lys Asn Val Tyr Asn Ser Trp Thr Tyr Asn Val Gln Tyr Trp Lys
145                 150                 155                 160

Asn Gly Thr Asp Glu Lys Phe Gln Ile Thr Pro Gln Tyr Asp Phe Glu
                165                 170                 175

Val Leu Arg Asn Leu Glu Pro Trp Thr Thr Tyr Cys Val Gln Val Arg
            180                 185                 190

Gly Phe Leu Pro Asp Arg Asn Lys Ala Gly Glu Trp Ser Glu Pro Val
        195                 200                 205

Cys Glu Gln Thr Thr His Asp Glu Thr Val Pro Ser Gly Ser Gly Ser
    210                 215                 220

Gly Ser Gly Ser Glu Pro Arg Ser Ser Asp Lys Thr His Thr Cys Pro
225                 230                 235                 240

Pro Cys Pro Ala Pro Glu Ala Glu Gly Ala Pro Ser Val Phe Leu Phe
                245                 250                 255

Pro Pro Lys Pro Lys Asp Thr Leu Met Ile Ser Arg Thr Pro Glu Val
            260                 265                 270

Thr Cys Val Val Val Asp Val Ser His Glu Asp Pro Glu Val Lys Phe
        275                 280                 285

Asn Trp Tyr Val Asp Gly Val Glu Val His Asn Ala Lys Thr Lys Pro
    290                 295                 300

Arg Glu Glu Gln Tyr Asn Ser Thr Tyr Arg Val Val Ser Val Leu Thr
305                 310                 315                 320

Val Leu His Gln Asp Trp Leu Asn Gly Lys Glu Tyr Lys Cys Lys Val
                325                 330                 335

Ser Asn Lys Ala Leu Pro Ser Ser Ile Glu Lys Thr Ile Ser Lys Ala
            340                 345                 350

Lys Gly Gln Pro Arg Glu Pro Gln Val Tyr Thr Leu Pro Pro Ser Arg
        355                 360                 365

Asp Glu Leu Thr Lys Asn Gln Val Ser Leu Thr Cys Leu Val Lys Gly
    370                 375                 380

Phe Tyr Pro Ser Asp Ile Ala Val Glu Trp Glu Ser Asn Gly Gln Pro
385                 390                 395                 400

Glu Asn Asn Tyr Lys Thr Thr Pro Pro Val Leu Asp Ser Asp Gly Ser
                405                 410                 415

Phe Phe Leu Tyr Ser Lys Leu Thr Val Asp Lys Ser Arg Trp Gln Gln
            420                 425                 430

Gly Asn Val Phe Ser Cys Ser Val Met His Glu Ala Leu His Asn His
        435                 440                 445

Tyr Thr Gln Lys Ser Leu Ser Leu Ser Pro Gly Lys Leu Val Pro Arg
    450                 455                 460

Gly Ser Gly Ser Gly Gly His His His His His His
465                 470                 475
```

<210> SEQ ID NO 24
<211> LENGTH: 63
<212> TYPE: DNA
<213> ORGANISM: Artificial Sequence
<220> FEATURE:
<223> OTHER INFORMATION: Oligonucleotide primer ZC29328

-continued

<400> SEQUENCE: 24

```
tcagagggat ccggttcggg ttcgggttcg gagcccagat catcagacaa aactcacaca     60

tgc                                                                   63
```

<210> SEQ ID NO 25
<211> LENGTH: 65
<212> TYPE: DNA
<213> ORGANISM: Artificial Sequence
<220> FEATURE:
<223> OTHER INFORMATION: Oligonucleotide primer ZC29231

<400> SEQUENCE: 25

```
cgactgactc gagctactcc ataggcatat actcgccacc tgatccttta cccggagaca     60

gggag                                                                 65
```

<210> SEQ ID NO 26
<211> LENGTH: 70
<212> TYPE: DNA
<213> ORGANISM: Artificial Sequence
<220> FEATURE:
<223> OTHER INFORMATION: Oligonucleotide primer ZC39335

<400> SEQUENCE: 26

```
atcggaattc gcagaagcca tgaggacgct gctgaccatc ttgactgtgg ggtccctggc     60

tgctcacgcc                                                            70
```

<210> SEQ ID NO 27
<211> LENGTH: 26
<212> TYPE: DNA
<213> ORGANISM: Artificial Sequence
<220> FEATURE:
<223> OTHER INFORMATION: Oligonucleotide primer ZC28981

<400> SEQUENCE: 27

```
tttgggctcc ctgagctctg gtggaa                                          26
```

<210> SEQ ID NO 28
<211> LENGTH: 80
<212> TYPE: DNA
<213> ORGANISM: Artificial Sequence
<220> FEATURE:
<223> OTHER INFORMATION: Oligonucleotide primer ZC39043

<400> SEQUENCE: 28

```
ctgactcgag ctactccata ggcatatact cgccacctga tccggaacca cgcggaacca     60

gtttacccgg agacagggag                                                 80
```

<210> SEQ ID NO 29
<211> LENGTH: 1452
<212> TYPE: DNA
<213> ORGANISM: Artificial Sequence
<220> FEATURE:
<223> OTHER INFORMATION: hzcytor11 extracellular cytokine binding domain
      fused to IgGg1 with a Glu-Glu tag
<220> FEATURE:
<221> NAME/KEY: CDS
<222> LOCATION: (1)...(1452)

<400> SEQUENCE: 29

```
atg agg acg ctg ctg acc atc ttg act gtg gga tcc ctg gct gct cac       48
Met Arg Thr Leu Leu Thr Ile Leu Thr Val Gly Ser Leu Ala Ala His
 1               5                  10                  15
```

-continued

```
gcc cct gag gac ccc tcg gat ctg ctc cag cac gtg aaa ttc cag tcc       96
Ala Pro Glu Asp Pro Ser Asp Leu Leu Gln His Val Lys Phe Gln Ser
             20                  25                  30

agc aac ttt gaa aac atc ctg acg tgg gac agc ggg cca gag ggc acc      144
Ser Asn Phe Glu Asn Ile Leu Thr Trp Asp Ser Gly Pro Glu Gly Thr
         35                  40                  45

cca gac acg gtc tac agc atc gag tat aag acg tac gga gag agg gac      192
Pro Asp Thr Val Tyr Ser Ile Glu Tyr Lys Thr Tyr Gly Glu Arg Asp
     50                  55                  60

tgg gtg gca aag aag ggc tgt cag cgg atc acc cgg aag tcc tgc aac      240
Trp Val Ala Lys Lys Gly Cys Gln Arg Ile Thr Arg Lys Ser Cys Asn
 65                  70                  75                  80

ctg acg gtg gag acg ggc aac ctc acg gag ctc tac tat gcc agg gtc      288
Leu Thr Val Glu Thr Gly Asn Leu Thr Glu Leu Tyr Tyr Ala Arg Val
                 85                  90                  95

acc gct gtc agt gcg gga ggc cgg tca gcc acc aag atg act gac agg      336
Thr Ala Val Ser Ala Gly Gly Arg Ser Ala Thr Lys Met Thr Asp Arg
            100                 105                 110

ttc agc tct ctg cag cac act acc ctc aag cca cct gat gtg acc tgt      384
Phe Ser Ser Leu Gln His Thr Thr Leu Lys Pro Pro Asp Val Thr Cys
        115                 120                 125

atc tcc aaa gtg aga tcg att cag atg att gtt cat cct acc ccc acg      432
Ile Ser Lys Val Arg Ser Ile Gln Met Ile Val His Pro Thr Pro Thr
    130                 135                 140

cca atc cgt gca ggc gat ggc cac cgg cta acc ctg gaa gac atc ttc      480
Pro Ile Arg Ala Gly Asp Gly His Arg Leu Thr Leu Glu Asp Ile Phe
145                 150                 155                 160

cat gac ctg ttc tac cac tta gag ctc cag gtc aac cgc acc tac caa      528
His Asp Leu Phe Tyr His Leu Glu Leu Gln Val Asn Arg Thr Tyr Gln
                165                 170                 175

atg cac ctt gga ggg aag cag aga gaa tat gag ttc ttc ggc ctg acc      576
Met His Leu Gly Gly Lys Gln Arg Glu Tyr Glu Phe Phe Gly Leu Thr
            180                 185                 190

cct gac aca gag ttc ctt ggc acc atc atg att tgc gtt ccc acc tgg      624
Pro Asp Thr Glu Phe Leu Gly Thr Ile Met Ile Cys Val Pro Thr Trp
        195                 200                 205

gcc aag gag agt gcc ccc tac atg tgc cga gtg aag aca ctg cca gac      672
Ala Lys Glu Ser Ala Pro Tyr Met Cys Arg Val Lys Thr Leu Pro Asp
    210                 215                 220

cgg aca tgg acc gga tcc ggt tcg ggt tcg ggt tcg gag ccc aga tca      720
Arg Thr Trp Thr Gly Ser Gly Ser Gly Ser Gly Ser Glu Pro Arg Ser
225                 230                 235                 240

tca gac aaa act cac aca tgc cca ccg tgc cca gca cct gaa gcc gag      768
Ser Asp Lys Thr His Thr Cys Pro Pro Cys Pro Ala Pro Glu Ala Glu
                245                 250                 255

ggg gca ccg tca gtc ttc ctc ttc ccc cca aaa ccc aag gac acc ctc      816
Gly Ala Pro Ser Val Phe Leu Phe Pro Pro Lys Pro Lys Asp Thr Leu
            260                 265                 270

atg atc tcc cgg acc cct gag gtc aca tgc gtg gtg gtg gac gtg agc      864
Met Ile Ser Arg Thr Pro Glu Val Thr Cys Val Val Val Asp Val Ser
        275                 280                 285

cac gaa gac cct gag gtc aag ttc aac tgg tac gtg gac ggc gtg gag      912
His Glu Asp Pro Glu Val Lys Phe Asn Trp Tyr Val Asp Gly Val Glu
    290                 295                 300

gtg cat aat gcc aag aca aag ccg cgg gag gag cag tac aac agc acg      960
Val His Asn Ala Lys Thr Lys Pro Arg Glu Glu Gln Tyr Asn Ser Thr
305                 310                 315                 320

tac cgt gtg gtc agc gtc ctc acc gtc ctg cac cag gac tgg ctg aat     1008
Tyr Arg Val Val Ser Val Leu Thr Val Leu His Gln Asp Trp Leu Asn
                325                 330                 335
```

-continued

```
ggc aag gag tac aag tgc aag gtc tcc aac aaa gcc ctc cca tcc tcc      1056
Gly Lys Glu Tyr Lys Cys Lys Val Ser Asn Lys Ala Leu Pro Ser Ser
            340                 345                 350

atc gag aaa acc atc tcc aaa gcc aaa ggg cag ccc cga gaa cca cag      1104
Ile Glu Lys Thr Ile Ser Lys Ala Lys Gly Gln Pro Arg Glu Pro Gln
        355                 360                 365

gtg tac acc ctg ccc cca tcc cgg gat gag ctg acc aag aac cag gtc      1152
Val Tyr Thr Leu Pro Pro Ser Arg Asp Glu Leu Thr Lys Asn Gln Val
    370                 375                 380

agc ctg acc tgc ctg gtc aaa ggc ttc tat ccc agc gac atc gcc gtg      1200
Ser Leu Thr Cys Leu Val Lys Gly Phe Tyr Pro Ser Asp Ile Ala Val
385                 390                 395                 400

gag tgg gag agc aat ggg cag ccg gag aac aac tac aag acc acg cct      1248
Glu Trp Glu Ser Asn Gly Gln Pro Glu Asn Asn Tyr Lys Thr Thr Pro
                405                 410                 415

ccc gtg ctg gac tcc gac ggc tcc ttc ttc ctc tac agc aag ctc acc      1296
Pro Val Leu Asp Ser Asp Gly Ser Phe Phe Leu Tyr Ser Lys Leu Thr
            420                 425                 430

gtg gac aag agc agg tgg cag cag ggg aac gtc ttc tca tgc tcc gtg      1344
Val Asp Lys Ser Arg Trp Gln Gln Gly Asn Val Phe Ser Cys Ser Val
        435                 440                 445

atg cat gag gct ctg cac aac cac tac acg cag aag agc ctc tcc ctg      1392
Met His Glu Ala Leu His Asn His Tyr Thr Gln Lys Ser Leu Ser Leu
    450                 455                 460

tct ccg ggt aaa ctg gtt ccg cgt ggt tcc gga tca ggt ggc gag tat      1440
Ser Pro Gly Lys Leu Val Pro Arg Gly Ser Gly Ser Gly Gly Glu Tyr
465                 470                 475                 480

atg cct atg gag                                                      1452
Met Pro Met Glu


<210> SEQ ID NO 30
<211> LENGTH: 484
<212> TYPE: PRT
<213> ORGANISM: Artificial Sequence
<220> FEATURE:
<223> OTHER INFORMATION: hzcytor11 extracellular cytokine binding domain
      fused to IgGg1 with a Glu-Glu tag

<400> SEQUENCE: 30

Met Arg Thr Leu Leu Thr Ile Leu Thr Val Gly Ser Leu Ala Ala His
 1               5                  10                  15

Ala Pro Glu Asp Pro Ser Asp Leu Leu Gln His Val Lys Phe Gln Ser
            20                  25                  30

Ser Asn Phe Glu Asn Ile Leu Thr Trp Asp Ser Gly Pro Glu Gly Thr
        35                  40                  45

Pro Asp Thr Val Tyr Ser Ile Glu Tyr Lys Thr Tyr Gly Glu Arg Asp
    50                  55                  60

Trp Val Ala Lys Lys Gly Cys Gln Arg Ile Thr Arg Lys Ser Cys Asn
65                  70                  75                  80

Leu Thr Val Glu Thr Gly Asn Leu Thr Glu Leu Tyr Tyr Ala Arg Val
                85                  90                  95

Thr Ala Val Ser Ala Gly Gly Arg Ser Ala Thr Lys Met Thr Asp Arg
            100                 105                 110

Phe Ser Ser Leu Gln His Thr Thr Leu Lys Pro Pro Asp Val Thr Cys
        115                 120                 125

Ile Ser Lys Val Arg Ser Ile Gln Met Ile Val His Pro Thr Pro Thr
    130                 135                 140

Pro Ile Arg Ala Gly Asp Gly His Arg Leu Thr Leu Glu Asp Ile Phe
145                 150                 155                 160
```

-continued

```
His Asp Leu Phe Tyr His Leu Glu Leu Gln Val Asn Arg Thr Tyr Gln
                165                 170                 175

Met His Leu Gly Gly Lys Gln Arg Glu Tyr Glu Phe Phe Gly Leu Thr
            180                 185                 190

Pro Asp Thr Glu Phe Leu Gly Thr Ile Met Ile Cys Val Pro Thr Trp
        195                 200                 205

Ala Lys Glu Ser Ala Pro Tyr Met Cys Arg Val Lys Thr Leu Pro Asp
    210                 215                 220

Arg Thr Trp Thr Gly Ser Gly Ser Gly Ser Gly Ser Glu Pro Arg Ser
225                 230                 235                 240

Ser Asp Lys Thr His Thr Cys Pro Pro Cys Pro Ala Pro Glu Ala Glu
                245                 250                 255

Gly Ala Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ser Ser
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Arg Asp Glu Leu Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
    450                 455                 460

Ser Pro Gly Lys Leu Val Pro Arg Gly Ser Gly Ser Gly Gly Glu Tyr
465                 470                 475                 480
Met Pro Met Glu
```

<210> SEQ ID NO 31
<211> LENGTH: 22
<212> TYPE: DNA
<213> ORGANISM: Artificial Sequence
<220> FEATURE:
<223> OTHER INFORMATION: Oligonucleotide primer ZC37693

<400> SEQUENCE: 31
ccccagacac ggtctacagc at 22

<210> SEQ ID NO 32
<211> LENGTH: 23
<212> TYPE: DNA
<213> ORGANISM: Artificial Sequence

```
<220> FEATURE:
<223> OTHER INFORMATION: Oligonucleotide primer ZC37449

<400> SEQUENCE: 32

gggtcaggcc gaagaactca tat                                              23


<210> SEQ ID NO 33
<211> LENGTH: 199
<212> TYPE: PRT
<213> ORGANISM: Homo sapiens

<400> SEQUENCE: 33

Met Val Pro Pro Pro Glu Asn Val Arg Met Asn Ser Val Asn Phe Lys
 1               5                  10                  15

Asn Ile Leu Gln Trp Glu Ser Pro Ala Phe Ala Lys Gly Asn Leu Thr
            20                  25                  30

Phe Thr Ala Gln Tyr Leu Ser Tyr Arg Ile Phe Gln Asp Lys Cys Met
        35                  40                  45

Asn Thr Thr Leu Thr Glu Cys Asp Phe Ser Ser Leu Ser Lys Tyr Gly
    50                  55                  60

Asp His Thr Leu Arg Val Arg Ala Glu Phe Ala Asp Glu His Ser Asp
65                  70                  75                  80

Trp Val Asn Ile Thr Phe Cys Pro Val Asp Asp Thr Ile Ile Gly Pro
                85                  90                  95

Pro Gly Met Gln Val Glu Val Leu Ala Asp Ser Leu His Met Arg Phe
            100                 105                 110

Leu Ala Pro Lys Ile Glu Asn Glu Tyr Glu Thr Trp Thr Met Lys Asn
        115                 120                 125

Val Tyr Asn Ser Trp Thr Tyr Asn Val Gln Tyr Trp Lys Asn Gly Thr
    130                 135                 140

Asp Glu Lys Phe Gln Ile Thr Pro Gln Tyr Asp Phe Glu Val Leu Arg
145                 150                 155                 160

Asn Leu Glu Pro Trp Thr Thr Tyr Cys Val Gln Val Arg Gly Phe Leu
                165                 170                 175

Pro Asp Arg Asn Lys Ala Gly Glu Trp Ser Glu Pro Val Cys Glu Gln
            180                 185                 190

Thr Thr His Asp Glu Thr Val
        195


<210> SEQ ID NO 34
<211> LENGTH: 211
<212> TYPE: PRT
<213> ORGANISM: Homo sapiens

<400> SEQUENCE: 34

Ser Asp Ala His Gly Thr Glu Leu Pro Ser Pro Pro Ser Val Trp Phe
 1               5                  10                  15

Glu Ala Glu Phe Phe His His Ile Leu His Trp Thr Pro Ile Pro Asn
            20                  25                  30

Gln Ser Glu Ser Thr Cys Tyr Glu Val Ala Leu Leu Arg Tyr Gly Ile
        35                  40                  45

Glu Ser Trp Asn Ser Ile Ser Asn Cys Ser Gln Thr Leu Ser Tyr Asp
    50                  55                  60

Leu Thr Ala Val Thr Leu Asp Leu Tyr His Ser Asn Gly Tyr Arg Ala
65                  70                  75                  80
```

-continued

```
Arg Val Arg Ala Val Asp Gly Ser Arg His Ser Asn Trp Thr Val Thr
                85                  90                  95

Asn Thr Arg Phe Ser Val Asp Glu Val Thr Leu Thr Val Gly Ser Val
            100                 105                 110

Asn Leu Glu Ile His Asn Gly Phe Ile Leu Gly Lys Ile Gln Leu Pro
        115                 120                 125

Arg Pro Lys Met Ala Pro Ala Asn Asp Thr Tyr Glu Ser Ile Phe Ser
    130                 135                 140

His Phe Arg Glu Tyr Glu Ile Ala Ile Arg Lys Val Pro Gly Asn Phe
145                 150                 155                 160

Thr Phe Thr His Lys Lys Val Lys His Glu Asn Phe Ser Leu Leu Thr
                165                 170                 175

Ser Gly Glu Val Gly Glu Phe Cys Val Gln Val Lys Pro Ser Val Ala
            180                 185                 190

Ser Arg Ser Asn Lys Gly Met Trp Ser Lys Glu Glu Cys Ile Ser Leu
        195                 200                 205

Thr Arg Gln
    210


<210> SEQ ID NO 35
<211> LENGTH: 201
<212> TYPE: PRT
<213> ORGANISM: Homo sapiens

<400> SEQUENCE: 35

Asp Glu Val Ala Ile Leu Pro Ala Pro Gln Asn Leu Ser Val Leu Ser
 1               5                  10                  15

Thr Asn Met Lys His Leu Leu Met Trp Ser Pro Val Ile Ala Pro Gly
            20                  25                  30

Glu Thr Val Tyr Tyr Ser Val Glu Tyr Gln Gly Glu Tyr Glu Ser Leu
        35                  40                  45

Tyr Thr Ser His Ile Trp Ile Pro Ser Ser Trp Cys Ser Leu Thr Glu
    50                  55                  60

Gly Pro Glu Cys Asp Val Thr Asp Asp Ile Thr Ala Thr Val Pro Tyr
65                  70                  75                  80

Asn Leu Arg Val Arg Ala Thr Leu Gly Ser Gln Thr Ser Ala Trp Ser
                85                  90                  95

Ile Leu Lys His Pro Phe Asn Arg Asn Ser Thr Ile Leu Thr Arg Pro
            100                 105                 110

Gly Met Glu Ile Thr Lys Asp Gly Phe His Leu Val Ile Glu Leu Glu
        115                 120                 125

Asp Leu Gly Pro Gln Phe Glu Phe Leu Val Ala Tyr Trp Arg Arg Glu
    130                 135                 140

Pro Gly Ala Glu Glu His Val Lys Met Val Arg Ser Gly Gly Ile Pro
145                 150                 155                 160

Val His Leu Glu Thr Met Glu Pro Gly Ala Ala Tyr Cys Val Lys Ala
                165                 170                 175

Gln Thr Phe Val Lys Ala Ile Gly Arg Tyr Ser Ala Phe Ser Gln Thr
            180                 185                 190

Glu Cys Val Glu Val Gln Gly Glu Ala
        195                 200
```